US007090349B2

(12) United States Patent
Perrott et al.

(10) Patent No.: US 7,090,349 B2
(45) Date of Patent: *Aug. 15, 2006

(54) SINGLE VISION LENSES

(75) Inventors: Colin Maurice Perrott, Mount Barker (AU); Kevin Douglas O'Connor, Goodwood (AU); Simon John Edwards, St. Peters (AU); Eric F. Barkan, Novato, CA (US); David H. Sklar, San Francisco, CA (US)

(73) Assignee: Sola International Holdings Ltd., Lonsdale (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/103,434

(22) Filed: Apr. 12, 2005

(65) Prior Publication Data

US 2005/0179859 A1 Aug. 18, 2005

Related U.S. Application Data

(62) Division of application No. 10/052,372, filed on Jan. 23, 2002, now Pat. No. 6,902,271, which is a division of application No. 09/142,869, filed as application No. PCT/AU97/00188 on Mar. 21, 1997, now Pat. No. 6,361,166.

(30) Foreign Application Priority Data

Mar. 21, 1996 (AU) .................................... PN 8806
Dec. 11, 1996 (AU) .................................... PO 4137

(51) Int. Cl.
*G02C 7/02* (2006.01)
*G02C 7/10* (2006.01)

(52) U.S. Cl. ........................ 351/177; 351/41; 351/159; 351/169

(58) Field of Classification Search ................ 351/159, 351/177, 41, 44, 163, 169
See application file for complete search history.

(56) References Cited

U.S. PATENT DOCUMENTS

| 1,697,030 A | 1/1929 | Tillyer |
| 1,741,536 A | 12/1929 | Rayton |

(Continued)

FOREIGN PATENT DOCUMENTS

AU          39432/68          1/1970

(Continued)

OTHER PUBLICATIONS

M. Jalie; The Principles of Ophthalmic Lenses; 1988, pp. 402-404, 425-446, Fourth Ed.; The Association of British Dispensing Opticians, London.

*Primary Examiner*—Scott J. Sugarman
(74) *Attorney, Agent, or Firm*—Buchanan Ingersoll PC

(57) ABSTRACT

Optical lens element with a prescription zone, suitable for use in wraparound or protective type eyewear. The element may also include a peripheral vision zone, with no prismatic jump between the zones. Design methods for the prescription zone include temporally rotating a prescription section about a vertical axis through the optical center thereof, and/or decentring the optical axis of said prescription section relative to the geometric axis thereof, and providing partial surface correction for astigmatic and/or mean power errors. For prescription powers in the range −6.0 to +6.0 diopters with 0 to 3 cyl, the optical lens element may be designed such that its front surface can be mounted in a frame of constant curvature of at least 5.0 diopters, with its back surface providing good clearance from temples and eyelashes. Applications include ophthalmic sunglass lenses.

5 Claims, 29 Drawing Sheets

Mean Vergence Power

Optical Astigmatism

U.S. PATENT DOCUMENTS

| | | |
|---|---|---|
| 1,918,999 A | 7/1933 | Wells |
| 1,942,400 A | 1/1934 | Glancy |
| 3,689,136 A | 9/1972 | Atamian |
| 3,691,565 A | 9/1972 | Galonek |
| 3,705,760 A | 12/1972 | Langendorfer, et al. |
| 4,187,505 A | 2/1980 | Morley et al. |
| 4,271,538 A | 6/1981 | Montesi et al. |
| 4,577,942 A | 3/1986 | Frieder et al. |
| 4,610,036 A | 9/1986 | LaPrairie |
| 4,645,317 A | 2/1987 | Frieder et al. |
| 4,741,611 A | 5/1988 | Burns |
| 4,778,266 A | 10/1988 | Maitenaz |
| 4,779,972 A | 10/1988 | Gottlieb |
| 5,056,906 A | 10/1991 | Akiyoshi |
| 5,094,520 A | 3/1992 | Reshef et al. |
| 5,110,199 A | 5/1992 | Ishida |
| 5,123,724 A | 6/1992 | Salk |
| 5,187,505 A | 2/1993 | Spector |
| 5,321,443 A | 6/1994 | Huber et al. |
| 5,416,537 A | 5/1995 | Sadler |
| 5,426,473 A | 6/1995 | Riehm |
| 5,483,303 A | 1/1996 | Hirschman |
| 5,526,068 A | 6/1996 | Markovitz |
| 5,604,547 A | 2/1997 | Davis et al. |
| 5,617,153 A | 4/1997 | Allen et al. |
| 5,644,374 A | 7/1997 | Mukaiyama et al. |
| 5,648,832 A | 7/1997 | Houston et al. |
| 5,650,838 A | 7/1997 | Roffman et al. |
| 5,689,323 A | 11/1997 | Houston et al. |
| 5,719,655 A | 2/1998 | Peschel et al. |
| 5,825,455 A | 10/1998 | Fecteau et al. |
| 6,010,218 A | 1/2000 | Houston et al. |
| 6,036,315 A | 3/2000 | Copeland |
| 6,129,435 A | 10/2000 | Reichow et al. |
| 6,142,624 A | 11/2000 | Morris et al. |
| 6,698,884 B1 * | 3/2004 | Perrott et al. ............... 351/169 |

FOREIGN PATENT DOCUMENTS

| | | |
|---|---|---|
| EP | 0 573 948 | 12/1993 |
| EP | 640523 | 3/1995 |
| FR | 2542462 | 9/1984 |
| FR | 2688322 | 9/1993 |
| GB | 680400 | 10/1952 |
| GB | 1509583 | 5/1978 |
| GB | 2 237 893 | 5/1991 |
| GB | 2281635 | 3/1995 |
| JP | 5-273502 | 10/1993 |
| JP | 6-123854 | 5/1994 |
| JP | 61-252525 | 11/1996 |
| WO | 91/17468 | 11/1991 |
| WO | 97/03579 | 2/1997 |
| WO | 97/21138 | 6/1997 |
| WO | 97/22894 | 6/1997 |
| WO | 97/35224 | 9/1997 |
| WO | 97/38343 | 10/1997 |
| WO | 97/41483 | 11/1997 |

\* cited by examiner

Optical Astigmatism
D=0.05D

Mean Vergence Power

SINGLE VISION LENSES

The present invention relates to sunglass lenses, in particular sunglass lenses with refractive power.

It is known in the prior art to manufacture non-corrective eyeglasses such as sunglasses or protective eyeglasses having wrap-around segments designed to shield the eye from incident light, wind, and foreign objects in the temporal vision field of the wearer.

Visible light and light in the UV region may enter the eye from angles as high as 100° from the line of sight.

It has not been possible, however, in prior art sunglasses or protective eyeglasses, to provide spectacle lenses with refractive power. The radii of curvature required to provide an ophthalmic lens defining a prescription zone is such that the spectacles would produce a bug-eyed appearance, which would be cosmetically unacceptable.

Whilst attempts have been made in the prior art to provide a wrap-around sun shield over otherwise generally standard prescription eyeglasses, such products are generally cosmetically unacceptable and suffer from significant optical distortions.

It is accordingly an object of the present invention to overcome, or at least alleviate, one or more of the difficulties and deficiencies related to the prior art.

Accordingly, in a first aspect, there is provided an optical lens element including a front and back surface capable of forming a prescription (Rx) zone; and a peripheral temporal zone.

Applicants have discovered that it is possible to provide a sufficient area of the lens to function as a prescription zone and yet still to provide a lens which provides a shield in the area of the temples. This is achieved by having a peripheral temporal zone.

By the term "optical lens element" as used herein, we mean an optical or ophthalmic lens, semi-finished lens or lens formed from a pair of lens wafers which may be utilised in the formation of an optical lens product.

The ophthalmic lens element may be a lens of negative or positive refractive power. Where the ophthalmic lens element includes an ophthalmic lens wafer, the peripheral temporal zone may be provided by the front wafer.

The optical lens element according to the present invention may be adapted for mounting in a frame of the wrap-around or shield type.

The peripheral temporal zone may be at least in part of generally toric shape. The peripheral temporal zone may be at least in part generally piano.

The peripheral temporal zone may itself form an extension of the prescription zone or may be a non-prescription zone.

In an alternative or additional aspect, the peripheral temporal zone may be modified to permit light control within the zone.

The lens element may be rotated temporally about a vertical axis through the optical centre thereof or the optical axis may be decentred relative to the geometric axis, or the lens element may be both rotated and decentred.

It will be understood that the peripheral temporal zone, for a typical sunglass lens element of the wrap-around type, may for example extend for approximately 10 to 25 mm.

In a further aspect of the present invention, there is provided an optical lens element providing prescription (Rx) correction generally in the range −6.0 D to +6.0 D with 0 to +3 cyl wherein the front surface is capable of being mounted in a frame of constant design curve irrespective of the Rx, such frame curves being 5.0 D and above; and the back surface provides good clearance from temples or eye lashes.

The ophthalmic lens element may form part of a series of lens elements, e.g. of the type described in International Patent Application PCT/EP97/00105, the entire disclosure of which is incorporated herein by reference.

Preferably the front surface is capable of being mounted in a frame of constant design curve of between 8.0 D and 9.0 D.

More preferably the front surface of the lens element has a high curve extending from nasal to temporal limits, but the vertical curve is 6.0 D or below.

It will be understood that such vertical curves permit the final prescription lenses, preferably edged lenses, to be adapted to the shape of the wearer's face and so locate closely in a form of the wrap-around type (so-called "toric" design).

Alternatively the optical lens elements may be adapted for mounting in a frame of the shield type. Accordingly in a still further aspect of the present invention there is provided a unitary optical lens including a pair of optical lens elements, each lens element providing prescription (Rx) correction generally in the range −6.0 D to +6.0 D with 0 to +3 cyl wherein the front surface is capable of being mounted in a frame of constant design curve irrespective of the Rx, such frame curves being 5.0 D and above; and the back surface provides good clearance from temples or eye lashes.

Accordingly in a particularly preferred embodiment the present invention provides a spectacle frame, or a unitary lens, including a pair of optical lens elements, which lens elements provide true Rx correction in a prescription (Rx) zone for a wearer up to 50° off axis, preferably 80° off axis, and terminating in a peripheral temporal zone, that provides clear perception of objects in the peripheral area of human vision and avoids prismatic jump from the prescription zone to the peripheral temporal zone.

The optical lens element according to the present invention may, when mounted, in a spectacle frame, be rotated temporally about a vertical axis through the optical centre thereof.

Accordingly in a further aspect of the present invention, there is provided an optical lens element adapted for mounting in a frame of the wrap-around or shield type, such that the lens element is rotated temporally about a vertical axis through, the optical centre thereof, the lens element including a front and back surface capable of forming a prescription (Rx) zone; and optionally a peripheral temporal zone;

the front and/or back surface bearing a surface correction to at least partially adjust for errors including astigmatic and power errors.

In this embodiment, whilst the optical axis continues to intersect the line of sight of the wearer, a number of optical effects and errors are thus introduced as discussed below. However, by suitable selection of the combination of front and/or back surface, the optical errors may be reduced or eliminated.

Accordingly, in a still further aspect of the present invention there is provided an optical lens element adapted for mounting in a frame of the wrap-around or shield type, the lens element including a front and back surface capable of forming a prescription (Rx) zone; and optionally a peripheral temporal zone wherein the optical axis is decentred relative to the geometric axis of the lens element to provide for prismatic correction, the front and/or back surface bearing a surface correction to at least partially adjust for errors including astigmatic and power errors.

Applicants have discovered that it is possible to produce an optical lens element, preferably a sunglass lens element, which includes a prescription (Rx) zone and which is decentred to provide a prismatic correction.

Preferably the front and/or back surface of the optical lens element further includes a surface correction to at least partially adjust for prismatic errors introduced by lens tilt.

Illustrative optical effects and errors may be summarised as follows:

The effects are described by consideration of the effects seen by the wearer along the line of sight that intersects the optical axis of the lens element:

Astigmatic Error

There is an induced astigmatic error such that the astigmatism, a, is proportional to the power of the lens, P, and proportional to the square of the rotation angle of the lens.

Power Errors

When the lens is used in a wrap-around form the mean through power of the lens changes. The mean power error, dP, is proportional to the astigmatic error, a, and proportional to a constant, k, that is related to the index of the lens. Hence in a minus Rx the mean power becomes more negative and in a plus Rx the mean power becomes more positive.

Prismatic Effects

Due to the rotation of the lens and the oblique angle of the optical axis, lens prism is introduced.

Off-Axis Prismatic Disparity

Off-axis prismatic disparity will result from unequal distortions in the temporal and nasal fields, resulting in poor binocular vision.

Other important observations:

The lens element described may result in increased off-axis power and astigmatic errors due to the selection of a base (front) curve that is designed to fit standard wrap frames, rather than for best optical performance.

These errors may result in un-accommodatable power errors.

One or more of the following corrections may be introduced to reduce the errors described:

Mean Power Error Correction

The front and/or back surface curvature may be adjusted to account for the change in mean power resulting from rotation of the lens, the degree of correction depending upon a balance of wearer tolerable on-axis power error and reduction of un-accommodatable off-axis power errors.

Hence a full power correction for the introduced shift in through power to correct on-axis errors may be applied or a partial correction when off-axis power error is considered.

Astigmatic Error Correction

The front and/or back surface may at least in part be toric in nature to correct for astigmatic error resulting from the lens rotation discussed earlier. The degree of correction may fully correct for the astigmatism introduced due to rotation of the lens or may be partially corrected depending upon the application. A partial correction may be applied to achieve a tolerable on-axis astigmatic error so as to reduce the off-axis astigmatic errors.

Prismatic Correction

The optical centre may be shifted horizontally to compensate for prism induced by the lens rotation. This may be achieved by applying prescribed prism during surfacing or shifting of the lens element in a horizontal direction.

Additional Considerations

These corrections include, but are not limited to, pantoscopic lens tilt, variation in lens frame types, cosmetic requirements and average pupil-centre to lens distances depending on frame and lens form types.

Off-axis Prismatic Disparity

To correct for off-axis prismatic disparity the lens may include an aspheric surface on either the front or back surfaces, or both.

Aspherisation of Surfaces

Aspherisation of either the front or back surfaces may be utilised to correct for off-axis errors including errors introduced due to tilt and/or the selection of the base curves. Such off-axis error may include power and astigmatic error and prismatic disparity.

It will be understood, however, that whilst it is relatively simple to correct for any particular optical error, it is necessary to balance the correction to achieve acceptable overall performance of the lens.

Illustrative error corrections which may be undertaken for a typical rotation of approximately 20° about the vertical axis, for a range of plus (+) and (−) lens elements of varying power, are given in the following Table.

| Sphere | | | Eyeside Curve Corrections | |
|---|---|---|---|---|
| Rx Power | Mean Power Error | Astig Error | Vertical Meridian | Horizontal Meridian |
| −3.00 D | −0.33 D | −0.42 D × 90° | 0.12 D flatter | 0.54 D flatter |
| −6.00 D | −0.66 D | −0.84 D × 90° | 0.24 D flatter | 1.08 D flatter |
| +3.00 D | +0.33 D | −0.42 D × 0° | 0.12 D steeper | 0.54 D steeper |
| +6.00 D | +0.66 D | −0.84 D × 0° | 0.24 D steeper | 1.08 D steeper |

It is to be noted that the eyeside surface power corrections given assume that the above errors are fully corrected to recover the sphere Rx specified at the optical centre. Lesser corrections may be undertaken, if required, to achieve acceptable overall performance of the lens.

Accordingly in a preferred aspect the optical lens element includes a front and/or back surface having a surface curvature adjusted to partially compensate for central mean through power error; and a second surface correction to at least partially balance off-axis and on-axis astigmatic errors.

In a still further preferred aspect, the second surface correction may include a toric component on the front and/or back surface to at least partially correct for astigmatic error.

Lens correction included in the optical lens element of the present invention may be grouped as two types:

those corrections that result from the lens rotation about the optical axis, or astigmatic and power error correction, and those corrections required by the wearer's prescription, or prescription correction.

The front surface may, in a preferred aspect, include a base curvature appropriate for high base curve lenses, e.g. for wrap around use. The nature of the front surface may mainly be dictated by cosmetic requirements.

Desirably, the front and/or back surface(s) of the optical lens element includes a spherical or toric component to provide the desired prescription (Rx) in the prescription zone.

More preferably the front and/or back surface includes a toric component and bears a surface correction to at least partially adjust for on-axis astigmatic and mean power errors. Such on-axis errors may result from the temporal rotation of the lens when mounted in a wrap-around or shield type frame.

Alternatively, or in addition, the front and/or back surface includes an aspheric component selected to at least partially adjust for off-axis astigmatic and mean power errors as well as prismatic disparity.

Preferably the front surface includes such an aspheric component. Such off-axis errors may result in part from the temporal rotation of the lens when mounted in a wrap-around or shield type frame and in part from the selection of a base curvature appropriate for high base curve lenses.

In a further preferred aspect, in order to provide the peripheral temporal zone the front and/or back surface, preferably the front surface, is an aspheric surface that includes appropriate aspheric coefficients to define a peripheral temporal zone.

Alternatively, the peripheral temporal zone may be provided by having an extension of the curvature of the front and/or back surface, the opposite surface being modified to complement the extended surface.

Accordingly the optical lens element includes a front surface including a spherical or toric component designed to provide the desired prescription (Rx) in the prescription zone, and bearing a surface correction to at least partially adjust for errors including astigmatic and mean power errors, in combination with the back surface, and including appropriate coefficients to define a peripheral temporal zone; and a transition section therebetween designed to smoothly blend the prescription zone and peripheral temporal zone a back surface modified to complement the front surface.

Preferably the front surface in the peripheral temporal zone is generally spherical. More preferably the back surface is also generally spherical and of equal curvature to the peripheral temporal zone, thus providing a generally piano extension.

The back surface may preferably include a base curvature such that the patient's required prescription power, Rx, is achieved. The back surface may be further modified to complement the front surface selected.

The back surface of the ophthalmic lens element according to the present invention may accordingly, in a preferred aspect, include a toric surface selected to achieve the prescribed optical power and the prescribed lens cylinder correction, In a preferred aspect, the toric back surface may further include a surface correction to compensate for mean power and astigmatic errors introduced by lens wrap.

In a still further preferred aspect, the toric surface may be an aspheric surface. The aspheric toric surface may include an adjustment to correct off-axis astigmatic and/or mean power errors.

Accordingly, in a preferred aspect the optical lens element includes a spherical front surface that includes a base curvature appropriate for high base curve lenses, and a toric back surface of appropriate curvature to provide the prescribed optical lens power and prescribed lens cylinder requirement and including an adjustment for astigmatic and mean power errors to compensate for lens wrap.

In an alternative embodiment, the optical lens element includes a toric front surface that includes a base curvature appropriate for high base curve lenses, and a toric adjustment for astigmatic error correction to compensate for lens wrap, and a toric back surface of appropriate curvature to provide the prescribed optical lens power and prescribed lens cylinder.

In a further alternative embodiment, the optical lens element includes an aspheric front surface that includes a base curvature appropriate for high base curve lenses and appropriate aspheric coefficients to correct for off-axis power and/or astigmatism errors; and a toric back surface of appropriate curvature to provide the prescribed optical lens power and prescribed lens cylinder requirement that includes adjustments for astigmatic error correction to compensate for lens wrap.

In a still further alternative embodiment, the optical lens element includes an aspheric toric front surface that includes a base curvature appropriate for high base curve lenses, and a toric adjustment for astigmatic error correction to compensate for lens wrap, and a toric back surface of appropriate curvature to provide the prescribed optical lens power and prescribed lens cylinder.

The asphericity on the front surface may function to provide appropriate aspheric coefficients to correct for off-axis power and/or astigmatic errors.

The optical lens element accordingly may include a spherical front surface that includes a base curvature appropriate for high base curve lenses, and an aspheric toric back surface with appropriate aspheric coefficients to correct for off-axis power and/or astigmatism errors and a toric adjustment for astigmatic and mean power error correction to compensate for lens wrap, prescribed optical lens power and prescribed lens cylinder.

Alternatively the optical lens element includes a toric front surface that includes a base curvature appropriate for high base curve lenses, and a toric adjustment for astigmatic and mean power error correction to compensate for lens wrap, and an aspheric toric back surface which includes appropriate aspheric coefficients to correct for off-axis power and astigmatism errors, prescribed optical lens power and prescribed lens cylinder.

In a further alternative embodiment, the optical lens element includes an aspheric front surface that includes a base curvature appropriate for high base curve lenses and appropriate aspheric coefficients to correct for off-axis power and/or astigmatism errors, and an aspheric toric back surface with appropriate aspheric coefficients to correct for off axis power and/or astigmatism errors and a toric adjustment for astigmatic error correction to compensate for lens wrap, prescribed optical lens power and prescribed lens cylinder.

In a still further alternative embodiment, the optical lens element includes an aspheric toric front surface that includes a base curvature appropriate for high base curve lenses, a toric adjustment for astigmatic error correction to compensate for lens wrap, and includes appropriate aspheric coefficients to correct for off-axis power and/or astigmatism errors, and an aspheric toric back surface with appropriate aspheric coefficients to correct for astigmatic and mean power errors, prescribed optical lens power and prescribed lens cylinder.

In a particularly preferred embodiment, the optical lens element includes an aspheric front surface that includes a base curvature appropriate for high base curve lenses and appropriate aspheric co-efficients to define a peripheral temporal zone; and a back surface of appropriate curvature to provide the prescribed optical lens power and prescribed lens cylinder and including adjustments for astigmatic and mean power error correction to compensate for lens wrap.

In this embodiment, the power, cylinder and error corrections may all be undertaken on the back surface, thus minimising the difficulties in designing the wrap-around type front surface.

Preferably the aspheric front surface may exhibit line symmetry about the horizontal geometric axis thereof. The aspheric front surface may alternatively or in addition exhibit line symmetry about the vertical geometric axis thereof. Such line symmetry further simplifies the design of the front lens surface whilst improving the aesthetic appearance thereof.

Preferably the aspheric surface includes a correction in the horizontal direction. More preferably the back surface includes a base curvature such that the patient's required prescription power, Rx, in the prescription zone is achieved; the back surface being further modified to complement the front surface selected.

The aspheric front surface may be of generally conic shape.

In a preferred aspect of the present invention the ophthalmic lens element may be formed as a laminate of a back and front lens element.

Accordingly, in a preferred aspect of the present invention there is provided a laminate optical article adapted for mounting in a frame of the wrap-around or shield type, including a front lens element;

a complementary back lens element, the front and back surfaces of the laminate optical article being capable of forming a prescription (Rx) zone;

the front and/or back surface bearing a correction to at least partially adjust for errors including astigmatic and mean power errors; the front and/or back lens element optionally including a peripheral temporal zone.

As discussed above, the laminate article may be rotated temporally about a vertical axis through the optical centre thereof, or the optical axis may be decentred relative to the geometric axis, or the lens element may be both rotated and decentred.

Accordingly, in a preferred embodiment of this aspect of the present invention there is provided a laminate optical article adapted for mounting in a frame of the wrap-around or shield type, such that the lens element is rotated temporally about a vertical axis through the optical centre thereof, including a front lens element;

a complementary back lens element, the front and back surfaces of the laminate optical article being capable of forming a prescription (Rx) zone; the front and/or back surface bearing a correction to at least partially adjust for errors including astigmatic errors; the front and/or back lens element optionally including a peripheral temporal zone.

In a preferred embodiment, the front lens element may be generally piano.

The corresponding back lens element may include a lens element of positive or negative power.

If desired, there may be a distribution of distance power and cylinder between the front and back lens element.

Alternatively, the back lens element may be relatively thick, the laminate optical article forming a semi-finished lens.

In an alternative or additional aspect, the lens element may be modified to permit light control within the peripheral temporal zone. Desirably the peripheral temporal zone may be modified so that no images are created in temporal vision.

The peripheral temporal zone of the optical lens element according to the present invention may be constructed to maximise cosmetic appearance. Ideally, the peripheral temporal zone should show little or no optical difference from the remainder of the front surface of the ophthalmic lens element. For example, where the prescription Rx surface of the ophthalmic lens is a minus Rx lens, the temporal extension may exhibit a zero refractive power or positive refractive power. The temporal extension may be tapered in cross-section to maximise cosmetic acceptability.

Accordingly, in a preferred aspect the curvature of the front surface is modified in the peripheral temporal zone to substantially correspond to the curvature of the back surface thereof.

It will be understood that the peripheral temporal zone thus formed is a substantially piano extension.

The peripheral temporal zone may be treated with any suitable coatings to maximise the cosmetic appearance of the front surface thereof.

For example, the peripheral temporal zone may be designed such that there is a rapid transition from the interface between the temporal zone and the surface of refractive power such that vision will be out of focus to the wearer within the temporal extension. For example, for a minus Rx lens, the minimum degree to which the nominal power of the temporal segment should be positive relative to the distance Rx is in the range of approximately 1 to 1.25 Dioptres.

It will be understood that for a minus Rx lens, it is possible for only the front surface of the lens to bear the temporal zone. The back surface of the lens may be of conventional spherical or toric form whilst the angular reach of the temporal extension increases as the base curve of the lens is made steeper. For lenses where the base curve is relatively modest, for example 4 or 6 Dioptres, the temporal reach may be reduced compared to lenses of higher base curve. This is useful if the primary purpose of the lens design is to provide appealing cosmetics by eliminating the conventional edge on a minus Rx lens.

In an alternative aspect, where the front surface of the ophthalmic lens forms a plus Rx lens, the peripheral temporal zone may vary from the positive lens to approximately piano (for example a cylindrical lens). The ophthalmic lens of such construction may be suitable for prescriptions near piano if the temporal extension is likewise piano or slightly negative in refractive power. If the temporal extension retains some positive power as for a high plus Rx lens, this power may be at least 1 to 1.5 Dioptres less than the plus value of the Rx.

In a preferred embodiment, the front and rear surface of the optical lens element may together define a lens of minus power.

The front surface of the lens element in this embodiment may be of generally circular cross-section.

The rear surface of the lens element may be of generally conic cross-section.

The front surface to be of generally conic cross-section in the peripheral temporal zone, thus providing a generally piano temporal cross-section.

As stated above, the lens element may be modified to permit light control within the peripheral temporal zone. The reflected colour of a sunglass lens is primarily a function of the dyes at the front surface of the lens. A mirror coating may be applied to the back surface of the lens so that the combination of front and back surface reflections achieves specular intensity (mirror) and the sense of lens colour (tint). Alternatively, or in addition, a different tint coating or layer may be provided at the rear surface of the lens. This may alter both the intensity and spectral character of transmitted and reflected rays interacting with the over-tinted region of the lens.

In a further option, the front or rear surface (preferably the rear) may be frosted so that reflected and transmitted light is diffuse. That is, images are not formed by light which enters the lens. The frosted part of the lens is visually opaque (translucent) to a wearer. To someone else, the lens will reflect the tinted colour from its front surface against a dull shadow from the frosted part of the rear surface. Preferably the rear surface may include a localised mirror coating from which the reflection is a matte finish.

The peripheral temporal zone may be treated in a number of ways so that it will not create images in peripheral vision, irrespective of the optical design. The most direct methods simply prevent a perceptible intensity of focused light from passing through by blocking it with any one or a combination of:

Back Surface Gradient Mirror
Back Surface Gradient (Black) Tint
Back Surface Mist The mirror coating may be introduced utilising conventional techniques, for example vacuum deposition of metal film on a finished lens. A chemical solution of a pristine metallic layer may be deposited on part of a casting mould and subsequently a lens is cast against that mould. A metal mirror thus formed may transmit insufficient light to form any troublesome images and reflecting a soft matte finish in copper, nickel or whatever the chosen metal.

Alternatively, or in addition, the temporal extension may include one or more of the following:

Reflection Holographic Film: mirrored polymer sheet, e.g. approximately 0.5 mm thick giving brightly coloured, changing reflected colour patterns
Light Control Film: for example polycarbonate film, e.g. 0.8 mm thick limiting light transmission to a narrow angular band
Reflective Film: for example Mylar film 0.025 mm thick, 10% transmission/90% reflection
Liquid Crystal Film: for example polymeric sheet 0.20 mm thick changing colour across the full spectrum with changing temperature.

The ophthalmic lens may be formulated from any suitable material. A polymeric material may be used. The polymeric material may be of any suitable type. The polymeric material may include a thermoplastic or thermoset material. A material of the diallyl glycol carbonate type may be used.

The polymeric article may be formed from cross-linkable polymeric casting compositions, for example as described in applicants U.S. Pat. No. 4,912,155, U.S. patent application Ser. No. 07/781,392, Australian Patent Applications 50581/93 and 50582/93, and European Patent Specification 453159A2, the entire disclosures of which are incorporated herein by reference.

Such cross-linkable polymeric casting compositions may include a diacrylate or dimethacrylate monomer (such as polyoxyalkylene glycol diacrylate or dimethacrylate or a bisphenol fluorene diacrylate or dimethacrylate) and a polymerisable comonomer, e.g. methacrylates, acrylates, vinyls, vinyl ethers, allyls, aromatic olefins, ethers, polythiols and the like.

For example, in Australian Patent Application 8121687, the entire disclosure of which is incorporated herein by reference, applicant describes a cross-linkable coating composition including at least polyoxyalkylene glycol diacrylate or dimethacrylate and at least one poly functional unsaturated cross-linking agent.

Further, in Australian Patent Application 75160/91, the entire disclosure of which is incorporated herein by reference, applicant describes a polyoxyalkylene glycol diacrylate or dimethacrylate; a monomer including a recurring unit derived from at least one radical-polymerisable bisphenol monomer capable of forming a homopolymer having a high refractive index of more than 1.55; and a urethane monomer having 2 to 6 terminal groups selected from a group comprising acrylic and methacrylic groups.

Such polymeric formulations are UV cured or cured by a combination of UV and thermal treatment. The range of optical lenses sold under the trade designations "Spectralite" by Applicants have been found to be suitable.

The polymeric material may include a dye, preferably a photochromic dye, which may, for example, be added to the monomer formulation used to produce the polymeric material. The variation in depth of colour may be minimised by incorporating a pigment or dye into one or more layers of the optical article.

The ophthalmic lens element according to the present invention may further include standard additional coatings to the front or back surface including electrochromic coatings.

The front lens surface may include an anti-reflective (AR) coating, for example of the type described in U.S. Pat. No. 5,704,692 to applicants, the entire disclosure of which is incorporated herein by reference.

The front lens surface may include an abrasion resistant coating. e.g. of the type described in U.S. Pat. No. 4,954,591 to applicants, the entire disclosure of which is incorporated herein by reference.

In a particularly preferred form, the laminate ophthalmic article may include an inner layer providing desired optical properties of the type described in International Patent Application PCT/AU96/00805 to applicants, the entire disclosure of which is incorporated herein by reference.

The front and back surfaces may further include one or more additions conventionally used in casting compositions such as inhibitors, dyes including thermochromic and photochromic dyes, e.g. as described above, polarising agents, UV stabilisers and materials capable of modifying refractive index.

In a further preferred aspect of the present invention the optical lens element may be modified to accentuate facial form in the nasal region.

Accordingly the optical lens element may include a region of reduced or opposite curvature defining a nasal accentuating region.

In a more preferred form, the lens element may reach forward toward the nasal bridge and backward toward the temples.

In a still further aspect of the present invention there is provided spectacles including a spectacle frame of the wrap-around type adapted to receive a pair of optical lenses such that each lens is rotated temporally about a vertical axis through the optical centre thereof, and a pair of optical lens elements, each lens element including
 a front and/or back surface capable of forming a prescription (Rx) surface; and optionally
 a peripheral temporal zone;
 the front and/or back surface bearing a surface correction to at least partially adjust for errors including astigmatic errors.

The front and back surfaces of the optical lens elements may be of the types described above. The optical lens element may be decentred.

The spectacle frame according to this aspect of the present invention may be of any suitable type. The spectacle frame may permit adjustment of the inter-pupillary distance for example via attachment of a lens to the frame supports. Frames of the rimless and temple bar type may be used.

The ophthalmic lenses mounted within the frame may be formed from a semi-finished lens or front and back lens wafer as described above. The ophthalmic lenses may bear a prescription surface of minus or plus power.

In a further aspect of the present invention, there is provided a method of designing an optical lens element adapted for mounting in a frame of the wrap-around or shield type, which method includes
 providing
 a mathematical or numerical representation of a surface of an optical lens element including a section designed to provide the desired prescription (Rx) in the prescription zone; and optionally adding thereto a mathematical or numerical representation of a peripheral temporal zone to define a complete lens surface;
 rotating and/or decentring the representation of the lens surface to permit mounting in a suitable frame; and
 modifying the representation of the lens surface to at least partially adjust for errors including astigmatic and mean power errors.

In a preferred aspect, the method may include
 providing a mathematical or numerical representation of an aspheric front surface of an optical lens element including a section designed to provide the desired prescription (Rx) in the prescription zone and having appropriate aspheric coefficients to define a peripheral temporal zone;
 rotating and/or decentring the representation of the lens surface to permit mounting in a suitable frame;
 subsequently providing a mathematical or numerical representation of a prescription (Rx) back surface; and
 modifying the representation of the back surface of the lens element to at least partially adjust for prismatic and/or astigmatic errors.

Preferably the method includes
 providing
 a mathematical or numerical representation of a surface of an optical lens element including a section designed to provide the desired prescription (Rx) in the prescription zone; and adding thereto a first mathematical or numerical representation of a peripheral temporal zone thereto; and
 a second mathematical or numerical representation of a transition section designed to smoothly blend the prescription section and peripheral temporal zone to define a complete lens surface;
 rotating and/or decentring the representation of the lens surface to permit mounting in a suitable frame; and
 modifying the representation of the lens surface to at least partially adjust for errors including astigmatic and mean power errors.

In a particularly preferred form the aspheric front surface is an atoric front surface. The atoric front surface may exhibit line symmetry along the horizontal and/or vertical axis.

In a further preferred form the back surface is a toric back surface.

In a preferred form the aspheric front surface may include an additional correction in the horizontal direction to adjust for errors due to rotation.

Normal representation of the cross-section of a spherical or aspheric lens surface may be via the coordinates $$\text{sag} = A_2 R^2 + A_4 R^4 + A_6 R^6 + A_8 R^8$$

where R is the radius measured from the optical axis and $A_2$, $A_4$, $A_6$ and $A_8$ are coefficients that define power and asphericity. It is assumed that the lens is rotationally symmetric about the optical axis.

Thus $$R^2 = x^2 + z^2$$

where the x axis is normal to the optical axis (y) in the direction towards the temples and the z axis is vertical with respect to a wearer's face.

The use of asphericity in conventional lens design is to produce small deviations from spherical form and the components of power are defined by the surface curvatures $$T = [d^2 y/dr^2]/[1 + (dy/dr)^2]^{3/2} \qquad \text{tangential}$$

$$S = (dy/dr)/r \, [1 + (dy/dr)^2]^{1/2} \qquad \text{sagittal}$$

where the sag is denoted by y.

Surface power of the lens is therefore defined by the two derivatives $$dy/dr = 2A_2 R + 4A_4 R^3 + 6A_6 R^5 + 8A_8 R^7, \text{ and}$$

$$d^2 y/dr^2 = 2A_2 + 12A_4 R^2 + 30A_6 R^4 + 56A_8 R^6.$$

Torus Periphery

It is convenient to set up a torus geometry by regarding the total SAG as that due to the basic lens design curve plus a component "DSAG" which comes from a temporal curvature extending beyond some radius Ro and which is defined by a similar set of coefficients operating on the radial dimension (R–Ro). In this case $$\text{sag} = \text{SAG} \quad R \leq Ro,$$

wherein R is the radius measured from the optical axis and $A_2$, $A_4$, $A_6$ and $A_8$ are coefficients that define power and asphericity. It is assumed that the lens is rotationally symmetric about the optical axis.

$$\text{sag} = \text{SAG} + \text{DSAG} \quad R \geq Ro.$$

wherein $R_0$ defines the periphery of the temporal region; and $$DSAG = B_2(R-Ro)^2 + B_4(R-Ro)^4 + B_6(R-Ro)^6 + B_8(R-Ro)^8$$

wherein $B_2$, $B_4$, $B_6$ and $B_8$ are coefficients that define power and asphericity.

The first and second derivatives of sag are then the sums of the individual derivatives $$dy/dr \rightarrow dy_1/dr)_{r=R} + dy_2/dr)_{r=R-R0},$$

$$d^2y/dr^2 \rightarrow d^2y_1/dr^2)_{r=R} + d^2y_2/dr^2)_{r=R-RO},$$

where by definition both y and dy/dr are continuous at R=Ro, but the second differential is discontinuous.

In this model, then, the sagittal surface curvature is continuous and the tangential surface curvature is not unless the following condition applies $$B_2 = 0$$

Generalised Torus Formulation

If we generalise the expressions so that $$sag = SAG + \alpha(DSAG)^N \text{ for } R \geq Ro,$$

where $\alpha$ and $N \geq 1$ are numerical parameters, we gain greater freedom to model the surface and gain better control over surface power changes at the onset of toric curvature. The first and second derivatives are continuous at R=Ro if either of the following conditions applies $$2 > N \geq 1 \text{ and } B_2 = O, \text{ or}$$

$$N \geq 2 \text{ for all values of } B_2.$$

Conveniently, we have found a generalised representation that provides continuity of surface curvature in both sagittal and tangential directions. That is, we can model the toric form without discontinuities in surface power. Given such forms, we are able to place one surface behind another of similar generating equation to provide a lens with strong curvatures but without discontinuities in refractive power through the lens.

When the curves produced by the above models with N=1 and N=2 are calculated and plotted, it is evident that the torus sheet blends asymptotically to the central optic zone, provided the condition on $B_2$ is observed. The model departs very gradually from the design sphere, blending the optics of the two design zones.

Further Generalisation of Torus Formulation

It will be understood that the surfaces of a lens element are surfaces of rotation swept by any of the expressions above for sag with respect to a chosen axis of revolution. In the mathematical development above, we have specified rotational symmetry about the optical axis. This generates a lens form with the same mean surface power at horizontal and vertical meridians, having a peripheral temporal zone around the entire perimeter of the lens element.

Before such a lens element can be mounted proximate the face in a wrap around frame or shield, the temporal extension is cut away except at the locations corresponding to the temples of the wrap around eyewear.

In an alternative embodiment, the appropriate surface alteration may be formed from the SAG curves as defined above by rotating the sag curve about an axis parallel to the x axis within the plane of the horizontal meridian. The curved portions intended to provide the temporal extension of such lenses are then located towards the ends of the horizontal meridian, whilst the vertical curves may retain conventional spherical or aspheric lens form.

The expression for the sag on the surface of a lens element formed in this manner is $$sag = \sum_{n=1}^{4} (A_{2n}x^{2n} + C_{2n}Z^{2n}) \text{ for } x \leq x_0$$

$$\sum_{n=1}^{4} (A_{2n}x^{2n} + C_{2n}Z^{2n}) + \alpha \left\{ \sum_{n=1}^{4} B_{2n}(x-x_0)^{2n} \right\}^N \text{ for } x \geq x_0$$

If the parameters $A_{2n}$ and $C_{2n}$ are set equal, the optic zone has the same surface power in vertical and horizontal meridians.

If the parameters $C_{2n}$ correspond to curves of lower power than the $A_{2n}$ parameters specify, the surface power of the optic zone will be lower in the vertical meridian. Lens elements formed in this way assist in achieving conformance of the wrap around eyewear to the face. A high base curve of the order of B or 9 Dioptres way be used to wrap laterally to the temples. However a lower curve, for example approximately 2 to 5 Dioptres matches the vertical shape of the face and allows the lenses to be placed closer to the eyes without indenting on the brows or cheeks.

The use of such more conventional base curves to define the vertical meridian also alleviates the need to apply off axis astigmatism and power corrections in this meridian.

The present invention will now be more fully described with reference to the accompanying figures and examples. It should be understood, however, that the description following is illustrative only and should not be taken in any way as a restriction on the generality of the invention described above.

In the drawings:

FIG. 1 illustrates light paths through a lens surface bearing a sunglass tint.

FIG. 2s a stylised illustration of an ophthalmic lens (right hand lens) of minus Rx power.

Figure 1:
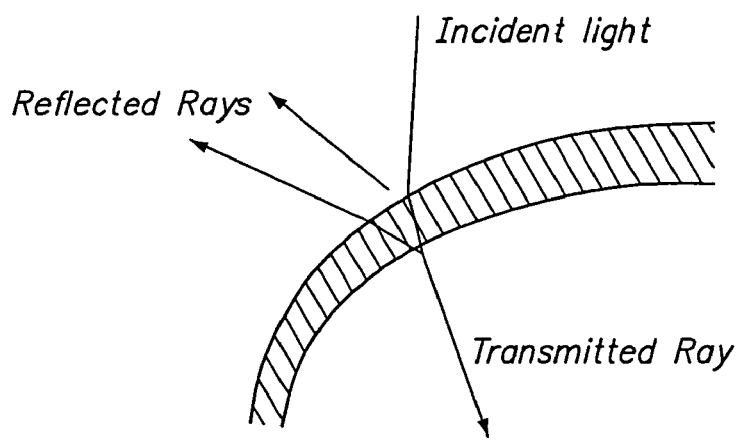
Figure 2:
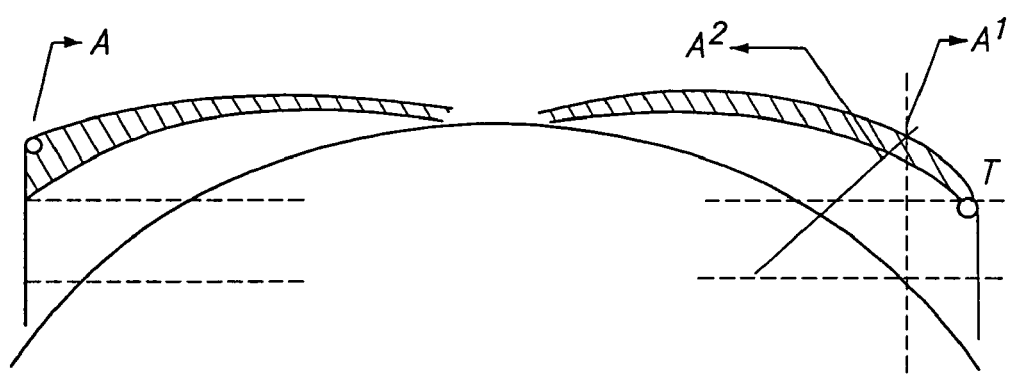
Figure 3:
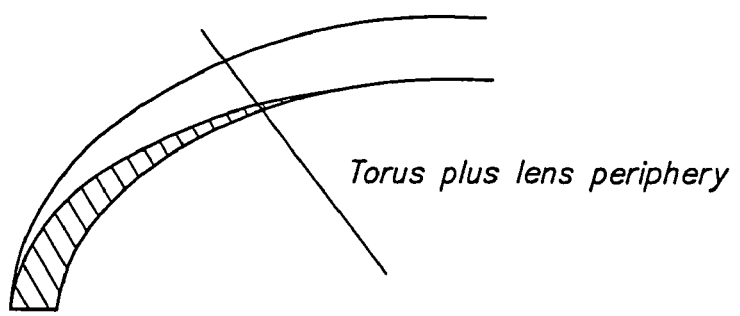
FIG. 3 is a stylised illustration of the peripheral temporal zone of an ophthalmic lens bearing a positive Rx surface.

FIG. 7(*a*) is a semi-finished optical blank: finished optical surface (1), unfinished rear surface (1'), axis of rotation symmetry (3), desired optical axis (4). In this example, the blank diameter is 76 mm, the front surface curve is 8 Dioptres and the angle between the axes (3) and (4) is 20°. The thickness of the blank may be 15 mm or so, depending on design needs.

FIG. 7(*b*) is a second optical surface (2) rotationally symmetric about the optical axis (4) created on the front of the optical blank by grinding and polishing. The difference in power of (1) and (2) is the final Rx power of the lens. In this example, (2) is 4 Dioptres.

FIG. 7(*c*) is a final Rx lens of power −4 Dioptres with a central optical zone of width ±35° around the optical axis (4). Curve (5) is identical dioptric power to (1) centred on axis (4). The temporal limit of the piano skirt (upper part of the drawing) of this lens is 88° from the line of forward sight for a rear vertex distance of 28 mm.

Figure 8A:
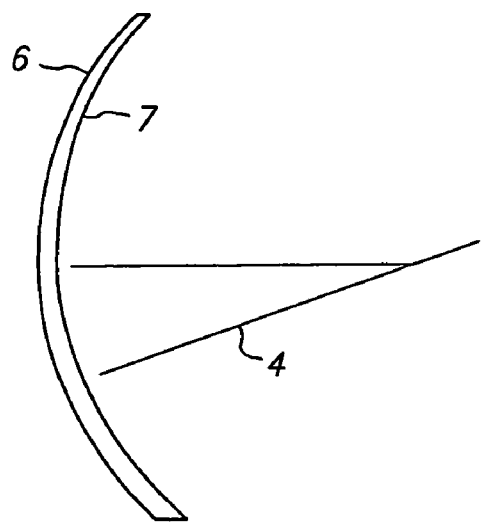

FIG. 8(a) is a true piano lens of 9 Dioptre base curve. Curves (6) and (7) are both 9 Dioptres centred on the optical axis (4). Note the apparent "base-in" prism of the lens when considered in terms of the displaced geometric axis. The nasal (lower) part of the lens is thicker.

Figure 8B:
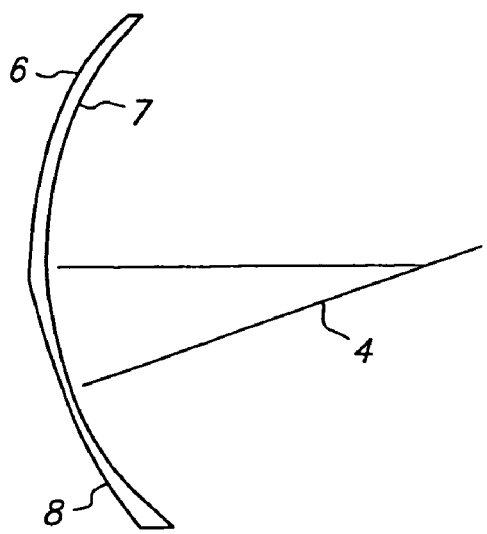

FIG. 8(b) is a final Rx lens of power −4 Dioptres created by curve (8) of 5 Dioptres centred on the optical axis (4).

Figure 9A:
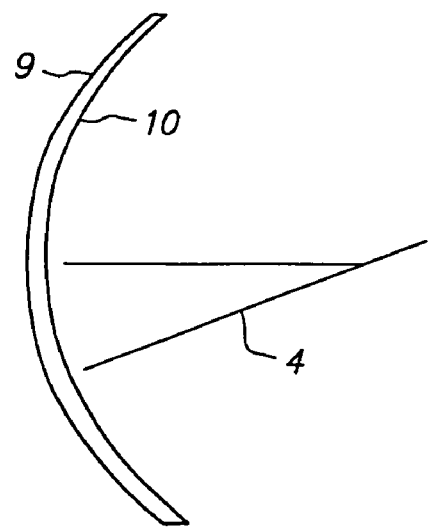

FIG. 9(a) is a true piano lens of 10 Dioptre base curve. Curves (9) and (10) are both 10 Dioptres centred on the optical axis (4). Note the apparent "base-in" prism of the lens when considered in terms of the displaced geometric axis. The nasal (lower) part of the lens is thicker.

Figure 9B:
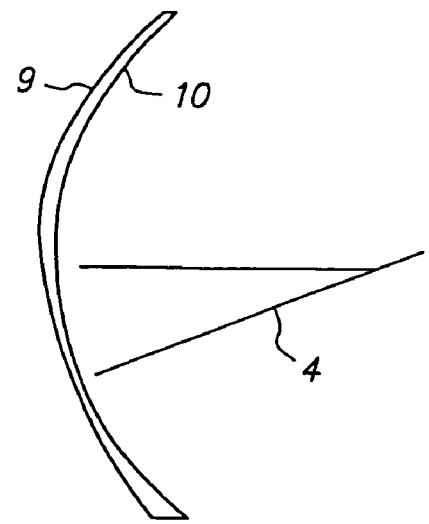

FIG. 9(b) is a final Rx lens of power −4 Dioptres created by curve (11) of 6 Dioptres centred on the optical axis (4). The optic zone width is ±45° for a rear vertex distance of 28 mm, with the temporal limit of the piano skirt of the lens being 95°.

Figure 10A:
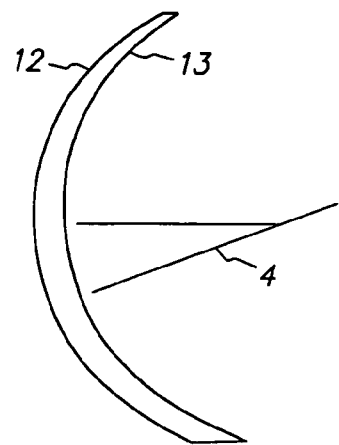

FIG. 10(a) is a true piano lens of 12 Dioptre base curve. Curves (12) and (13) are both 12 Dioptres centred on the optical axis (4). Note the apparent "base-in" prism of the lens when considered in terms of the displaced geometric axis. The nasal (lower) part of the lens is thicker.

Figure 7A:
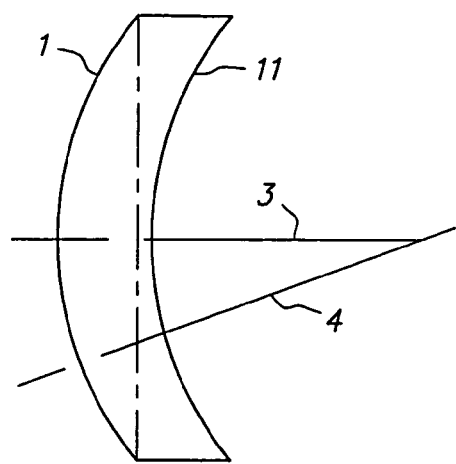
Figure 7B:
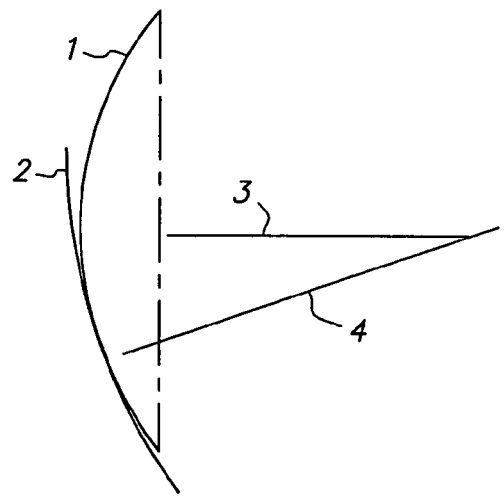
Figure 10B:
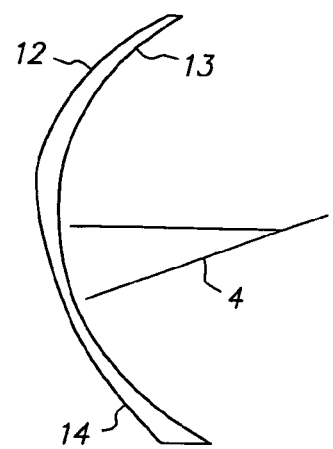

FIG. 10(b) is a final Rx lens of power −4 Dioptres created from the blank in FIG. 7(a); curve (14) is 8 Dioptres centred on the optical axis (4). The optic zone width is ±45° for a rear vertex distance of 28 mm, with the temporal limit of the piano skirt of the lens being 98°.

Figure 7C:
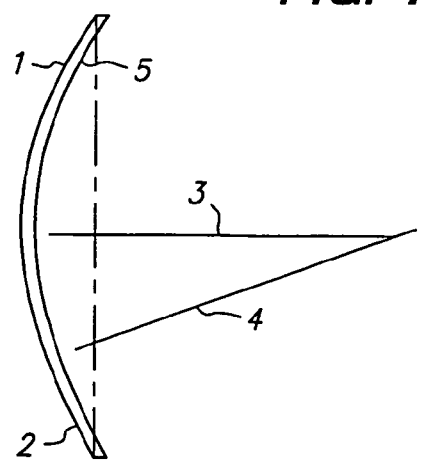
Figure 11A:
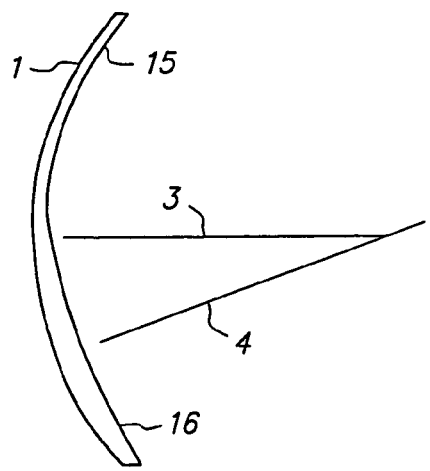

FIG. 11(a) is a final Rx lens of power +4 Dioptres produced from the semi-finished blank moulded against a back mould surface of similar form to the front of the lens shown in FIG. 7(c): curve (15) is −8.2 Dioptres centred on axis (4) to limit the final lens thickness, curve (16) is 4 Dioptres centred on axis (4). The optic zone is ±35° about the optical axis (4) and the pseudo piano temporal skirt (upper part of drawing) extends 87° from the forward line of sight for a rear vertex distance of 28 mm.

Figure 11B:
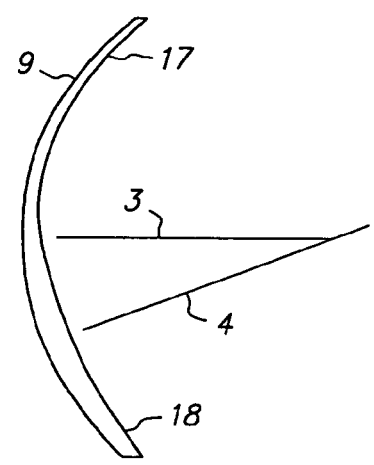

FIG. 11(b) is a final Rx lens of power +4 Dioptres: curve (17) is 10.2 Dioptres centred on axis (4) to limit the final lens thickness, curve (18) is 6 Dioptres centred on axis (4). The optic zone is ±40° about the optical axis (4) and the pseudo piano temporal skirt (upper part of drawing) extends 95° from the forward line of sight for a rear vertex distance of 28 mm.

Figure 11C:
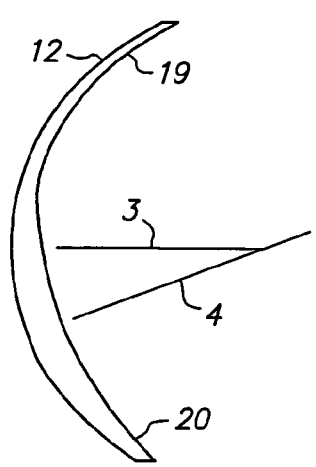

FIG. 11(c) is a final Rx lens of power +4 Dioptres: curve (19) is 12.25 Dioptres centred on axis (4) to limit the final lens thickness, curve (20 is 8 Dioptres centred on axis (4). The optic zone is ±48° about the optical axis (4) and the pseudo piano temporal skirt (upper part of drawing) extends 98° from forward line of sight for a rear vertex distance of 28 mm FIG. 12(a) is a schematic illustration of a pair of minus lens elements according to the present invention of −3.0D through power rotated about their vertical optical axes by 20°.

Figure 12A:
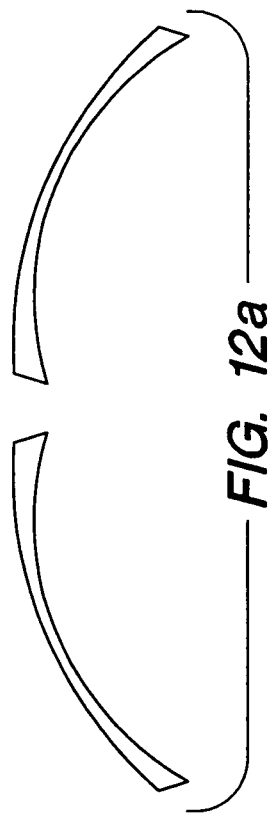
Figure 12C:
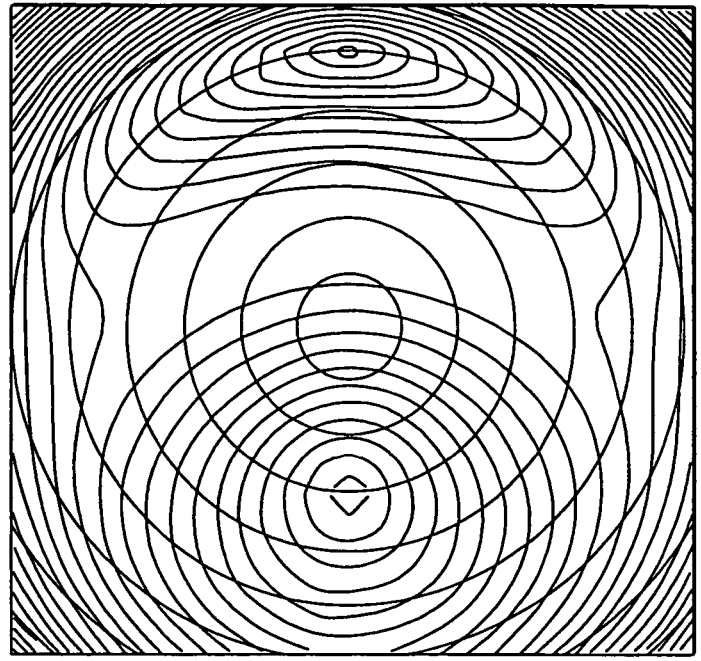
Figure 12B:
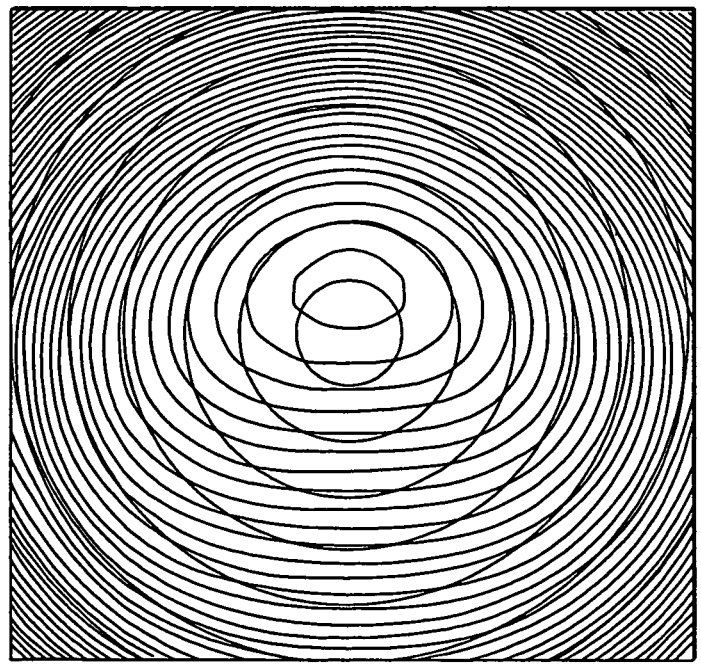
Figure 12E:
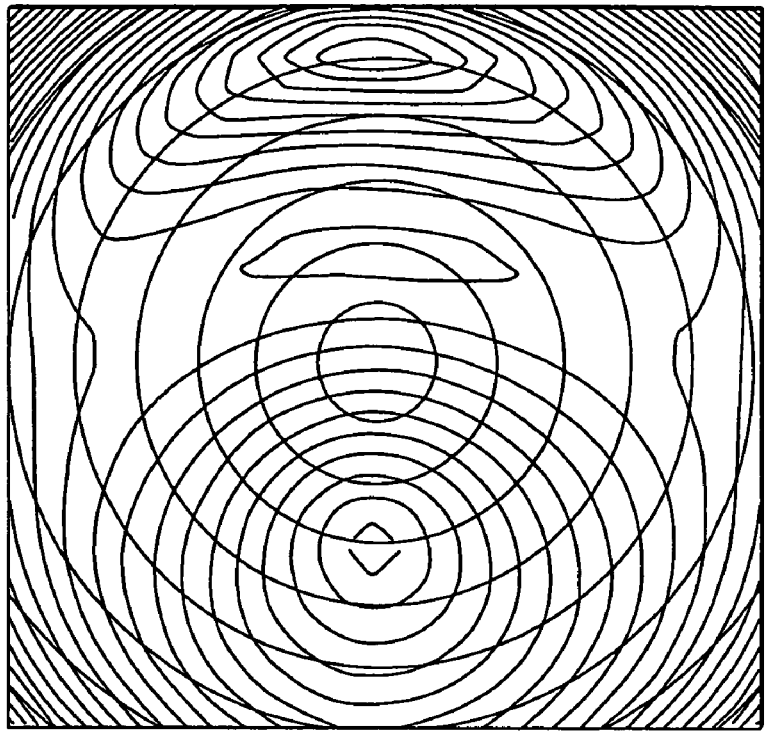

FIGS. 12(b) and (c) show the resulting mean surface power and astigmatism contours after the rotation of the lenses in FIG. 12(a).

Figure 12D:
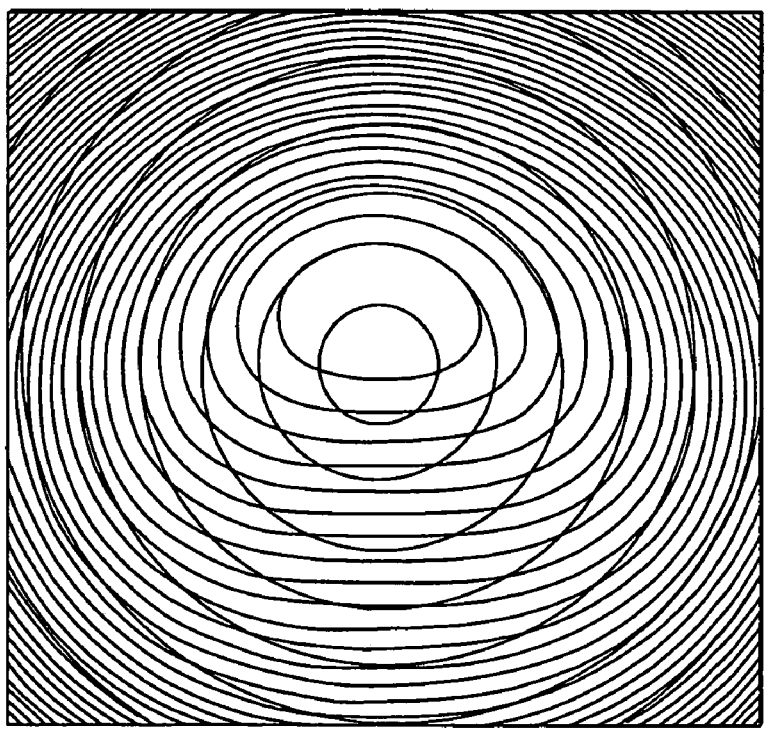
Figure 12G:
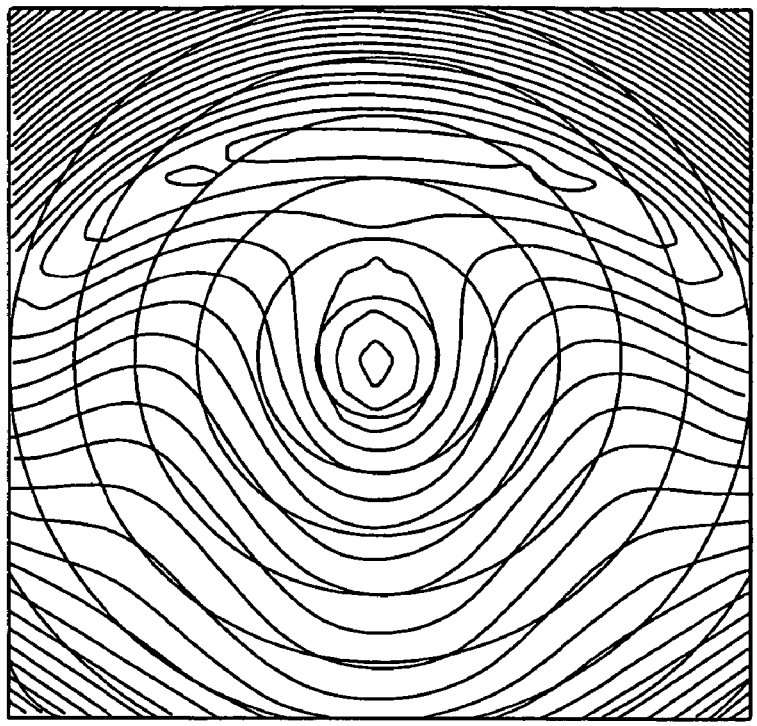

FIGS. 12(d) and (e) illustrate the resulting mean power and astigmatism contours after subjecting the back surfaces of the lenses of FIG. 12(a) to a full correction of the required mean through power.

Figure 12F:
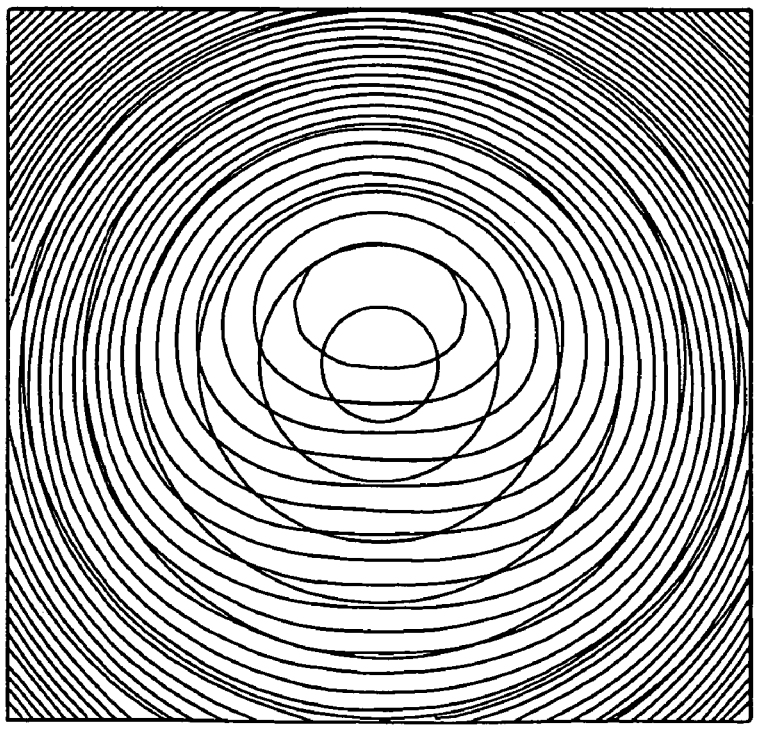
Figure 12I:
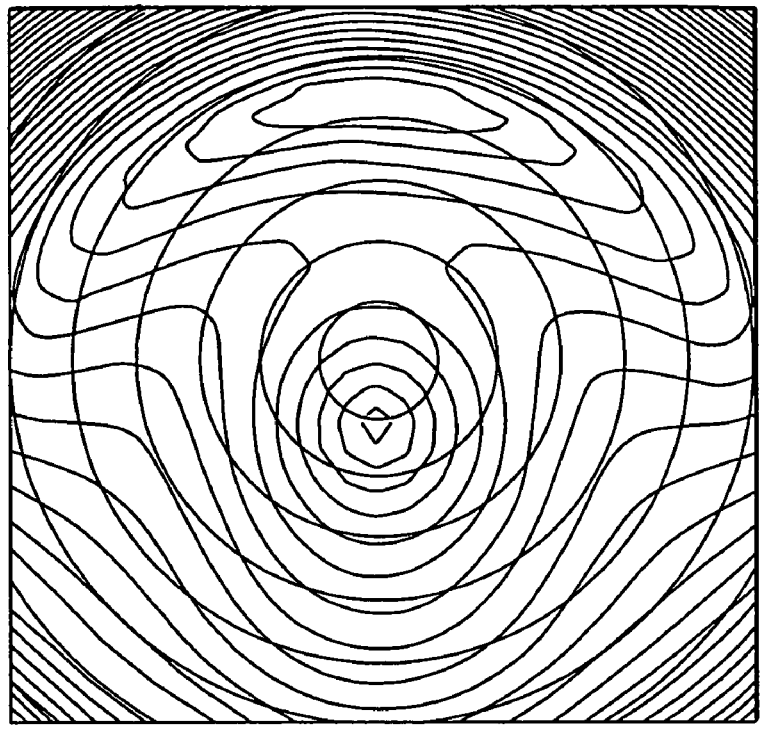

FIGS. 12(f) and (g) illustrate the resulting mean power and astigmatism contours after subjecting the back surfaces of the lenses of FIG. 12(a) to a further full toric back surface correction.

Figure 12H:
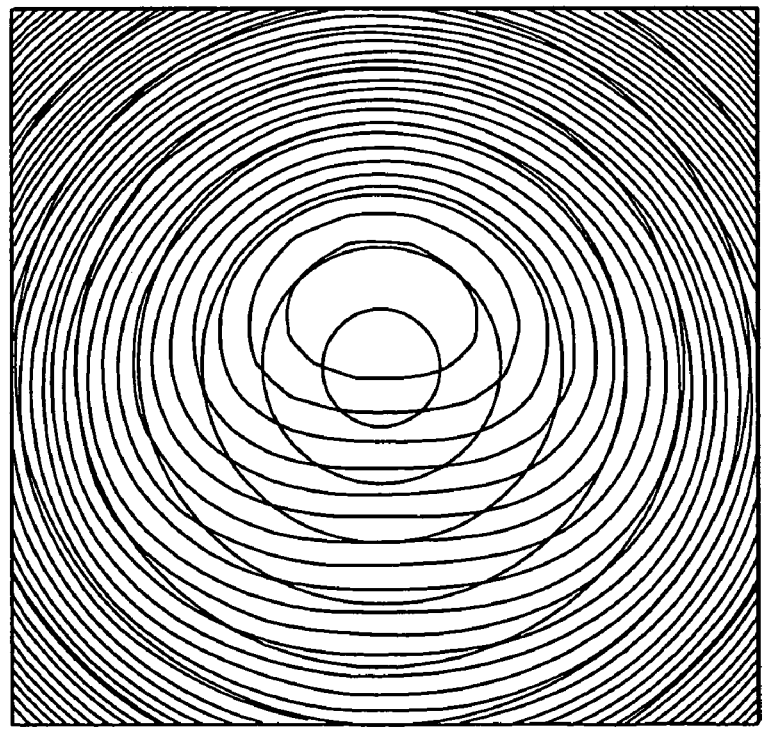
Figure 12K:
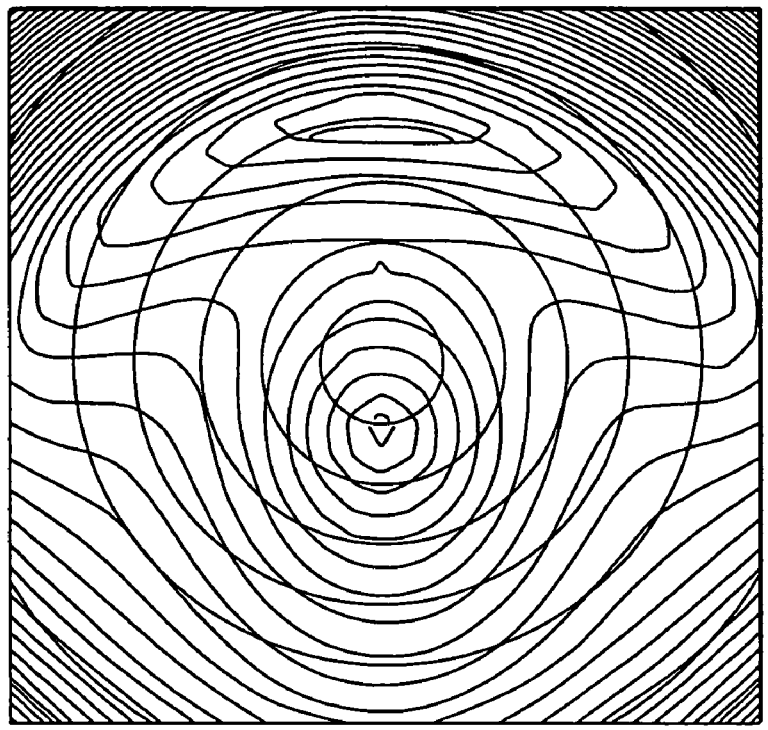

FIGS. 12(h) and (i) illustrate the resulting mean power and astigmatism contours after subjecting the back surfaces of the lenses of FIG. 12(a) to a further partial toric back correction.

Figure 12J:
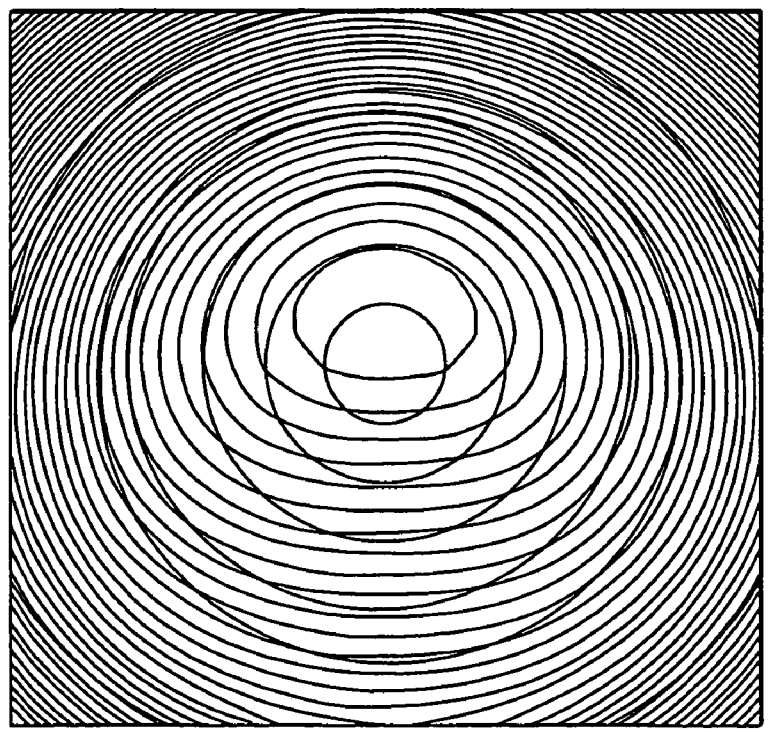

FIGS. 12(j) and (k) illustrate the resulting mean power and astigmatism contours after subjecting the back surfaces of the lenses of FIG. 12(a) to a partial mean power and partial toric back correction.

Figure 13A:
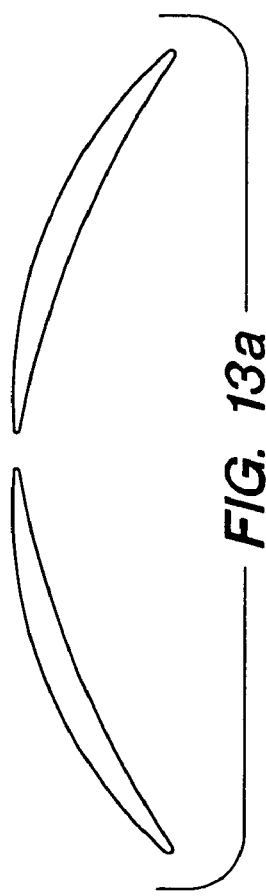
Figure 13C:
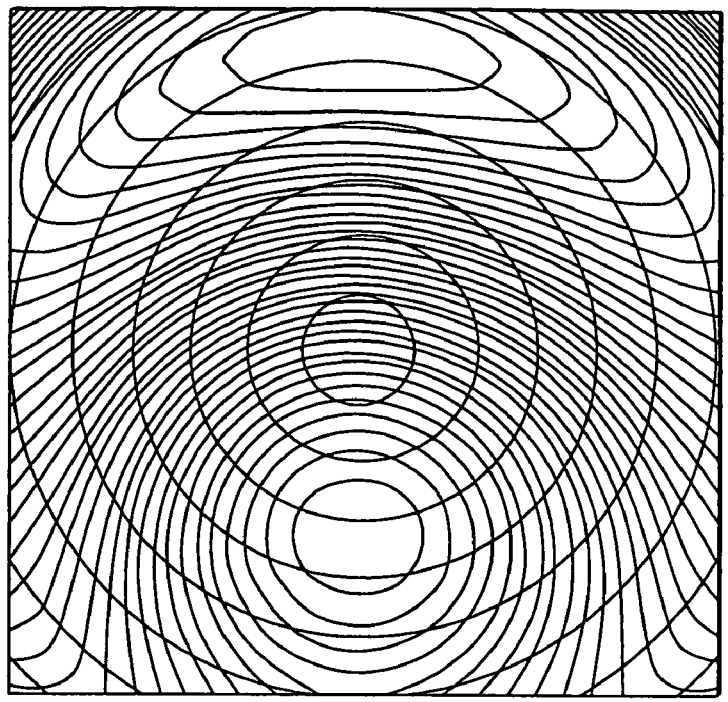

FIG. 13(a) is a schematic illustration of a pair of piano lens elements according to the present invention of 3.0D through power rotated about their vertical optical axes by 20°.

Figure 13B:
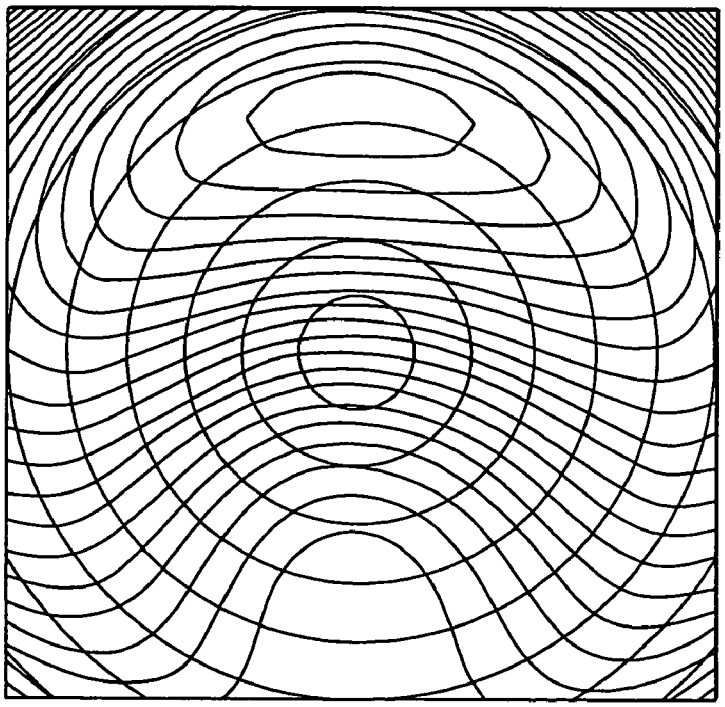
Figure 13E:
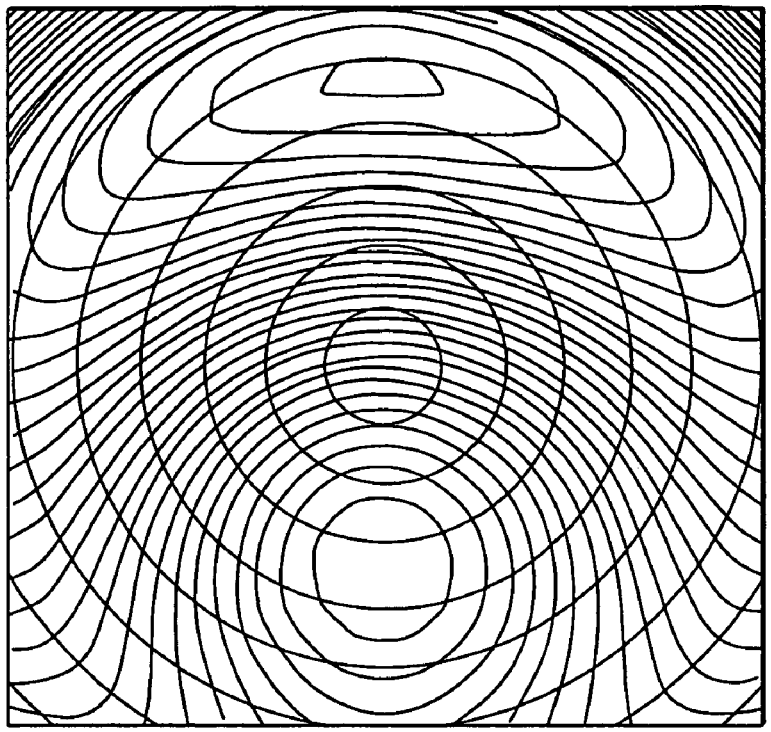

FIGS. 13(b) and (c) show the resulting mean surface power and astigmatism contours after the rotation of the lenses in FIG. 12(a).

Figure 13D:
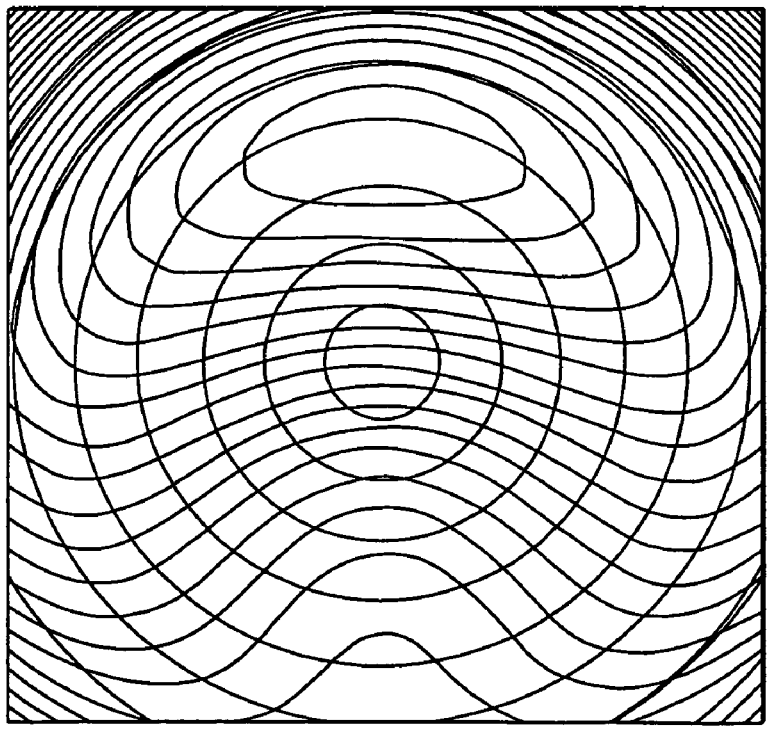
Figure 13G:
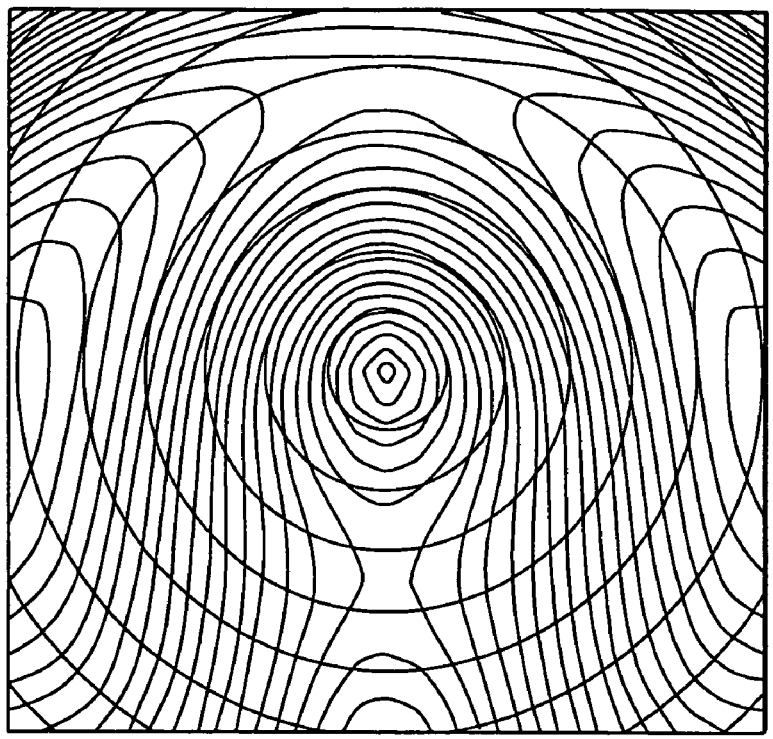

FIGS. 13(d) and (e) illustrate the resulting mean power and astigmatism contours after subjecting the back surfaces of the lenses of FIG. 12(a) to a full correction of the required mean through power.

Figure 13F:
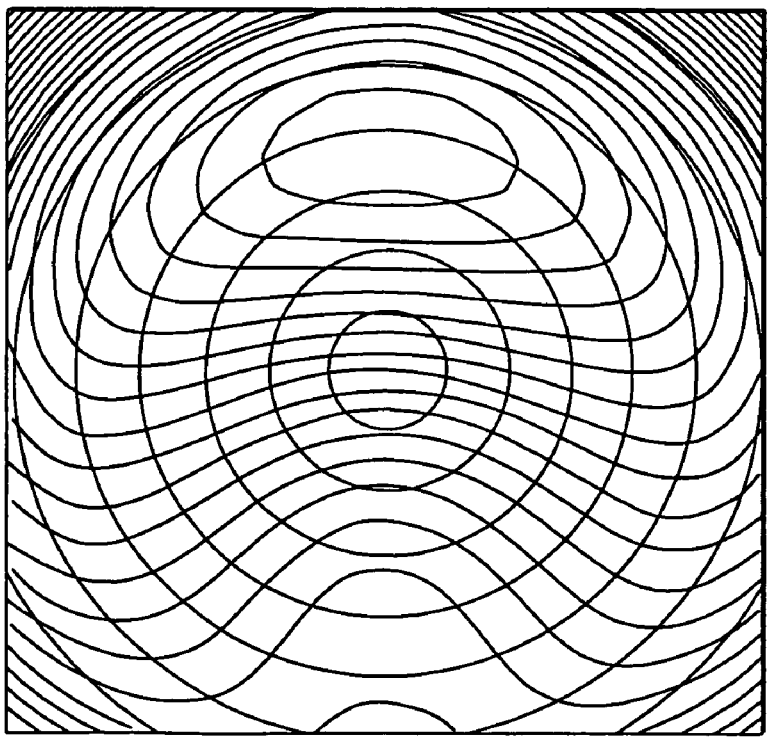
Figure 13I:
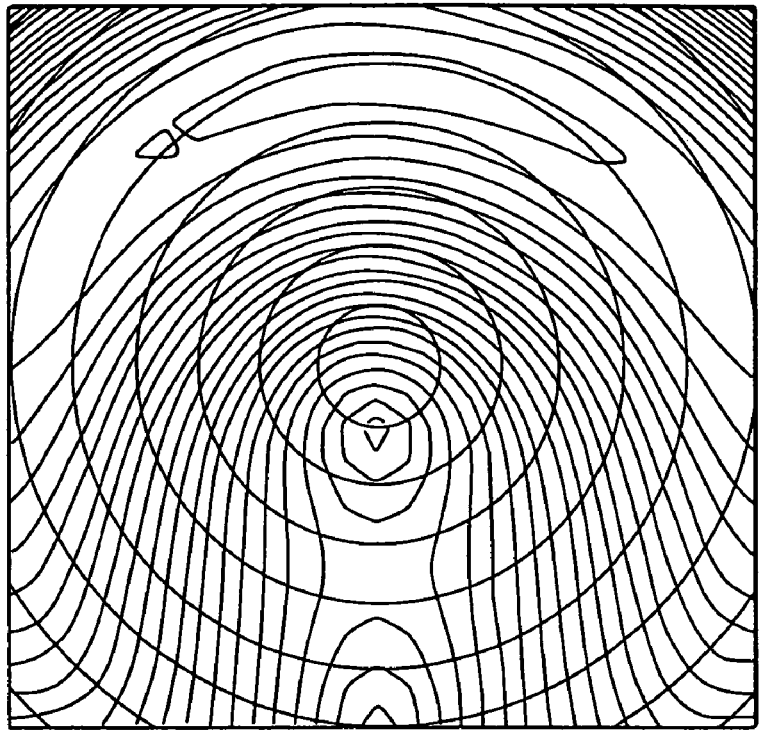

FIGS. 13(f) and (g) illustrate the resulting mean power and astigmatism contours after subjecting the back surfaces of the lenses of FIG. 12(a) to a further full toric front surface correction.

Figure 13H:
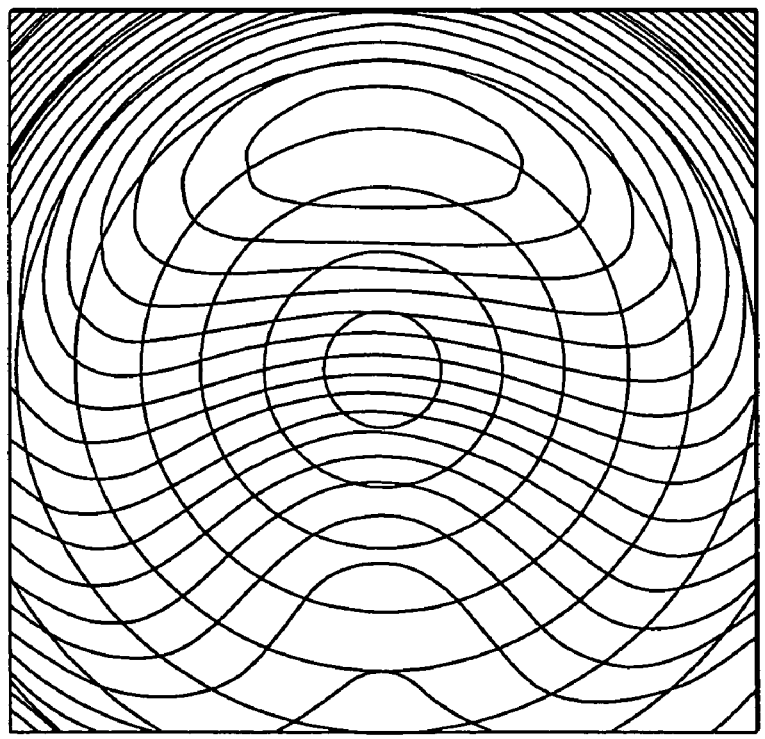

FIGS. 13(h) and (i) illustrate the resulting mean power and astigmatism contours after subjecting the back surfaces of the lenses of FIG. 12(a) to a further partial toric front correction.

Figure 14A:
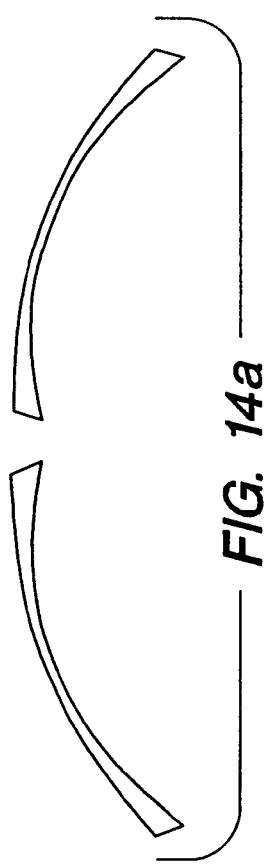

FIG. 14(a) is a schematic illustration of a pair of aspheric minus lens elements according to the present invention of −3.0D through power rotated about their vertical optical axes by 20°.

Figure 14C:
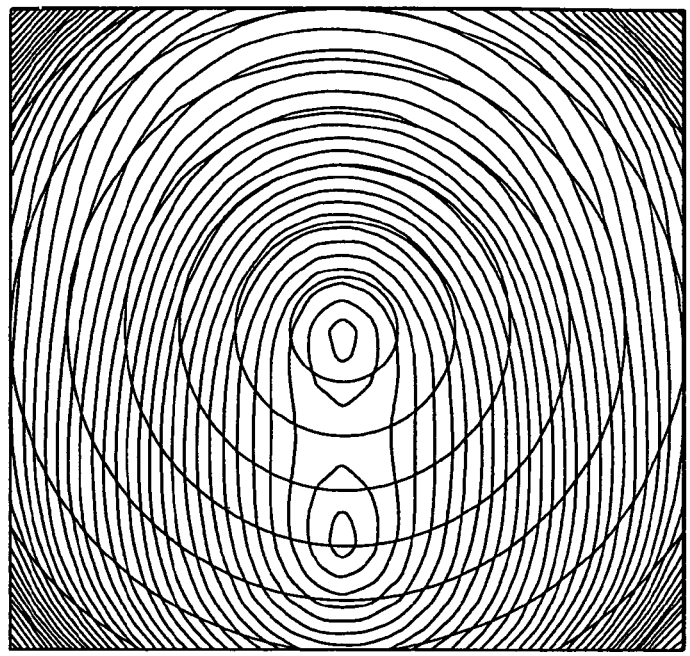
Figure 14B:
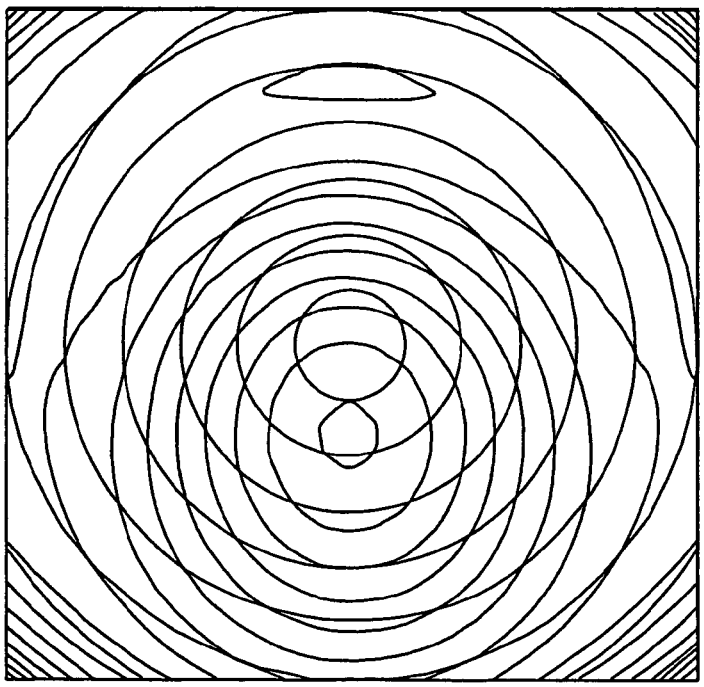

FIGS. 14(b) and (c) show the resulting mean surface power and astigmatism contours after subjecting the lens elements to aspherisation of the front surface and a full toric back surface correction.

Figure 15:
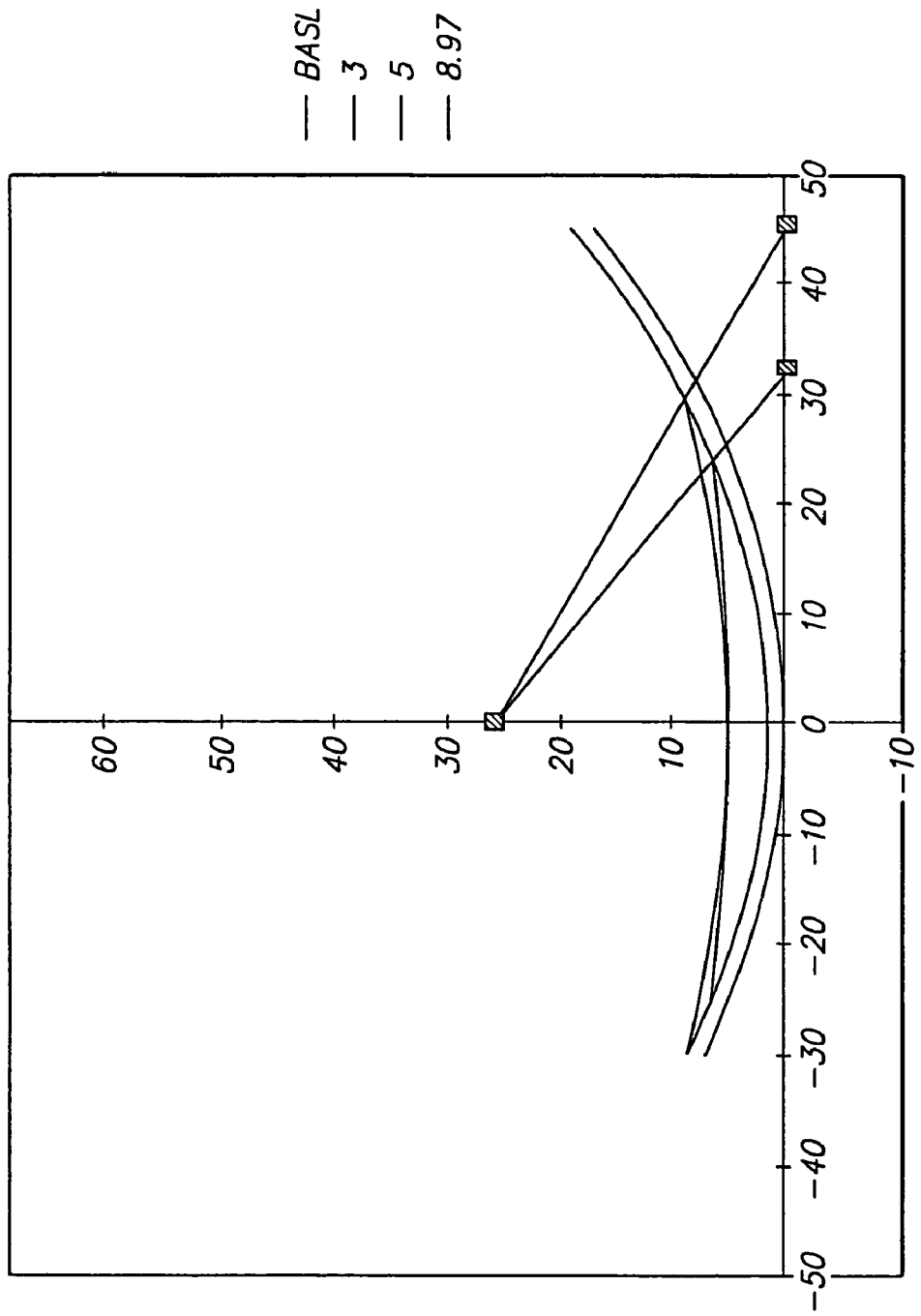
Figure 16:
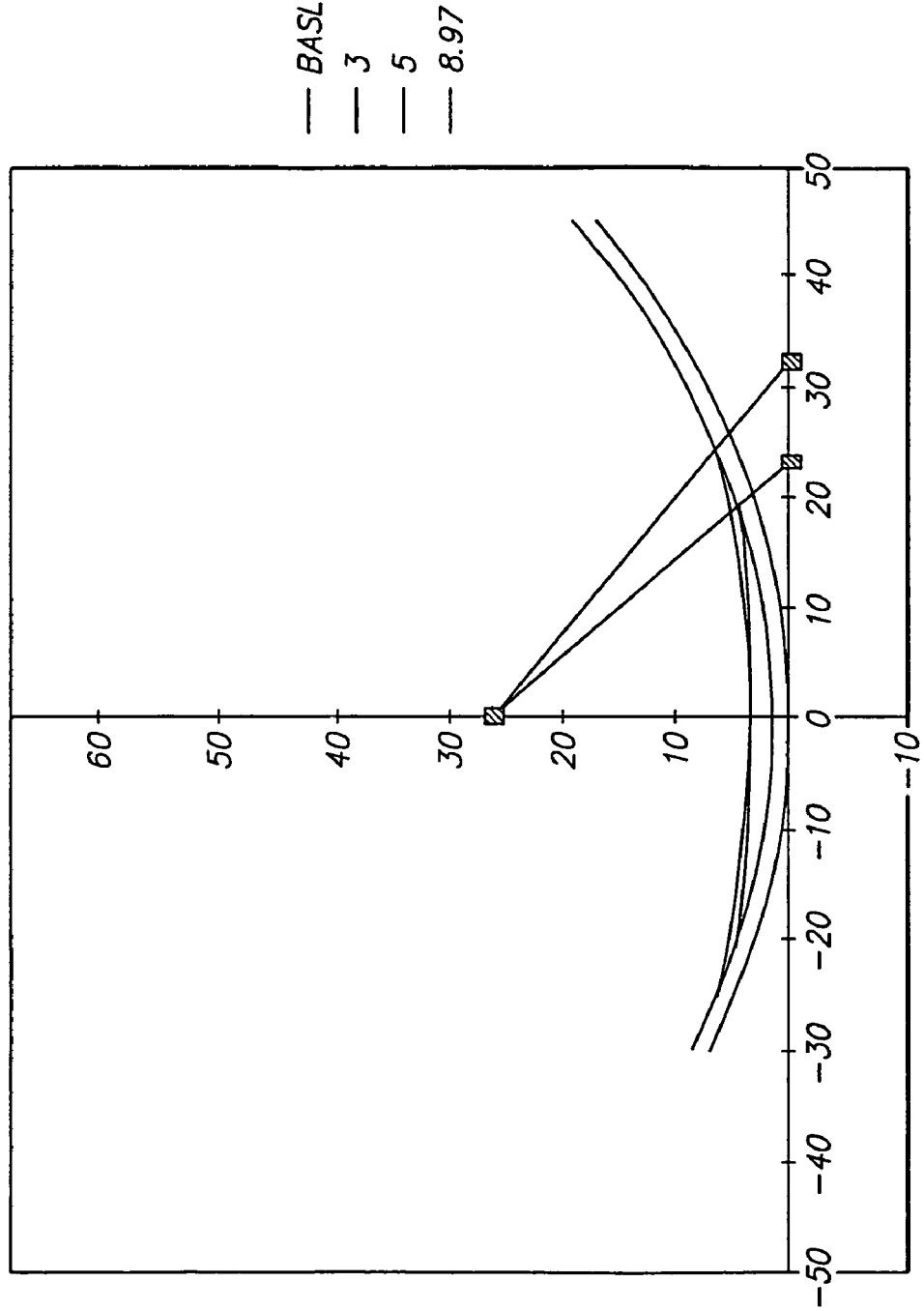

FIGS. 15 and 16 illustrate a series of laminate optical plus (+) lens elements.

Figure 17:
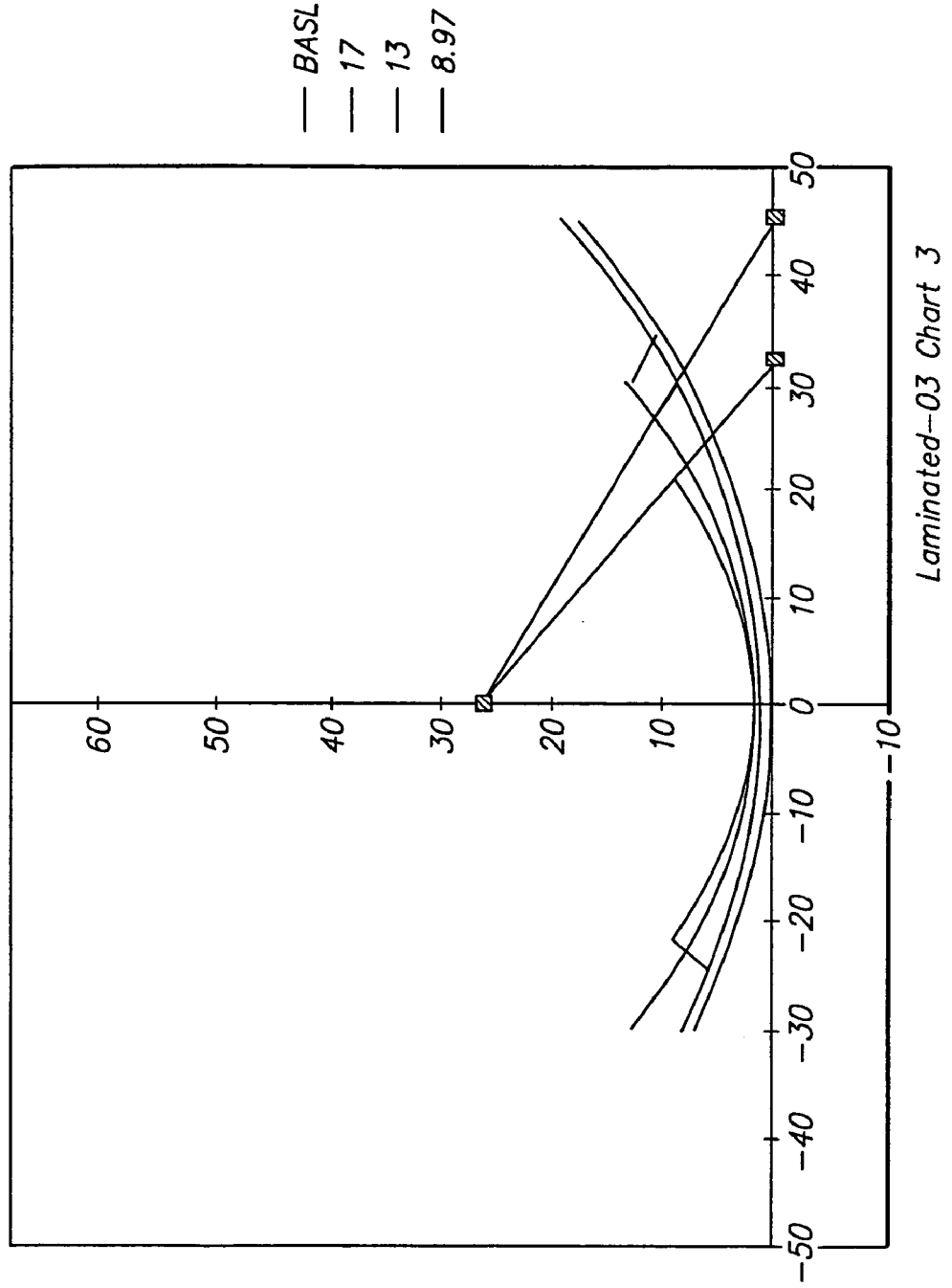

FIG. 17 illustrates a laminate optical minus (−) lens element.

Figure 18:
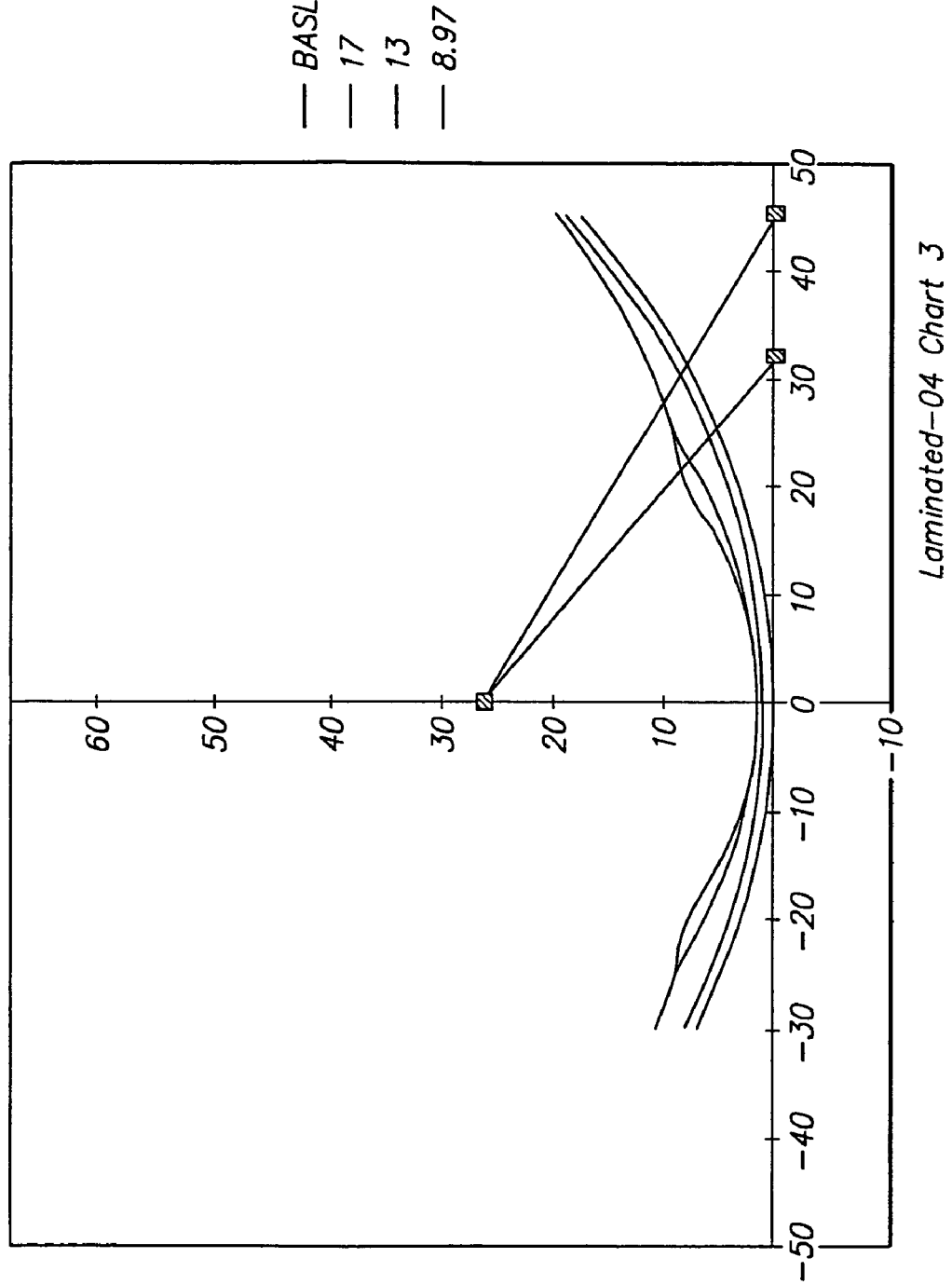

FIG. 18 illustrates a laminate or integral surfaced minus lens element wherein the thickness of the laminated assembly is adjusted by selecting back elements of different diameter, thus altering the size of the optical zone of the final lens.

Figure 19:
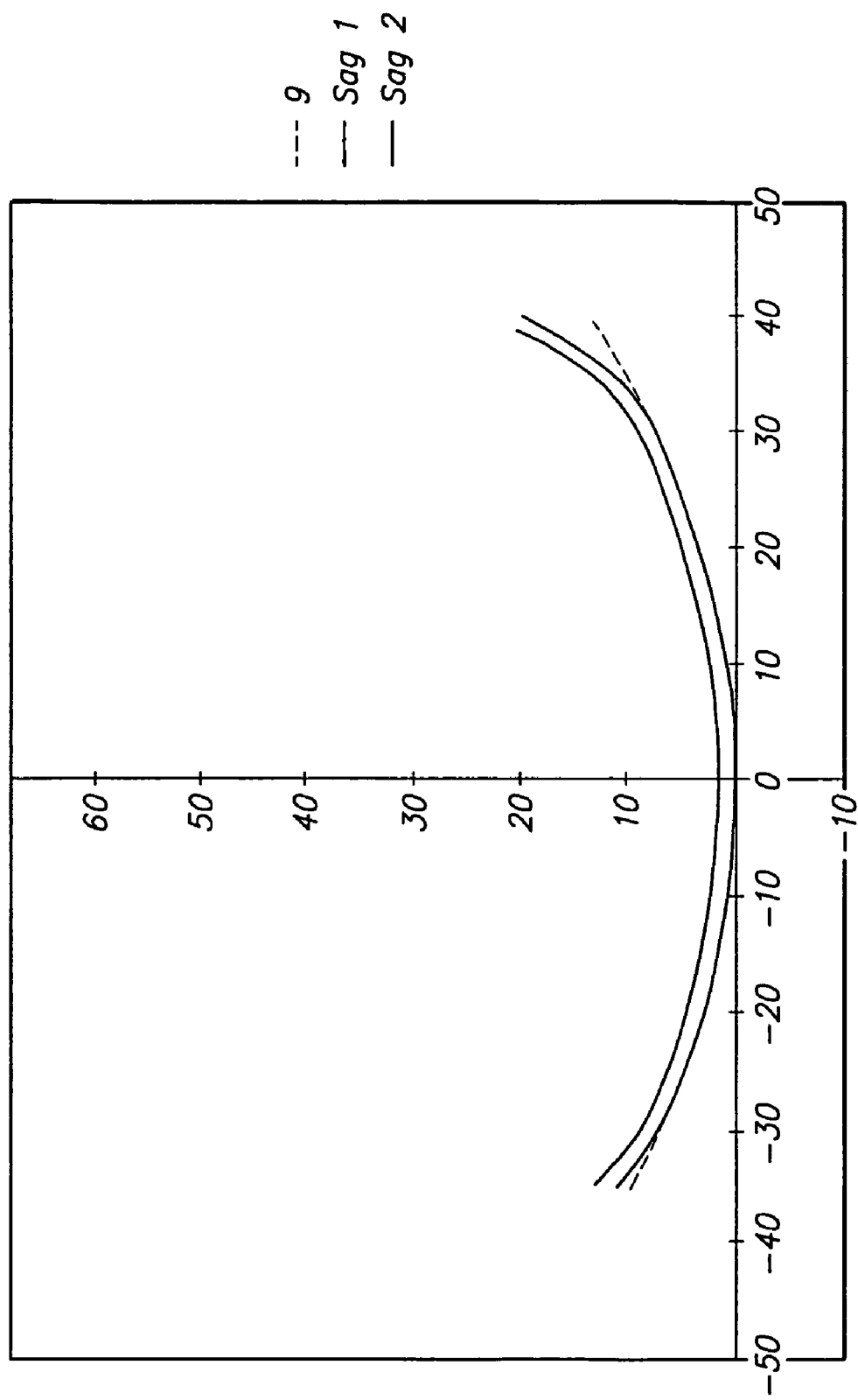

FIG. 19 illustrates optical lens elements including a temporal generally piano extension of modified curvature.

FIGS. 21 to 29 illustrate plus and minus optical lens elements whose front surfaces are described by the expression sag=SAG $R \leq R0$, sag=SAG+DSAG $R \geq R0$ and form both an optical zone giving the required Rx correction and a peripheral temporal zone with a simple spherical or toric back surface.

Figure 21:
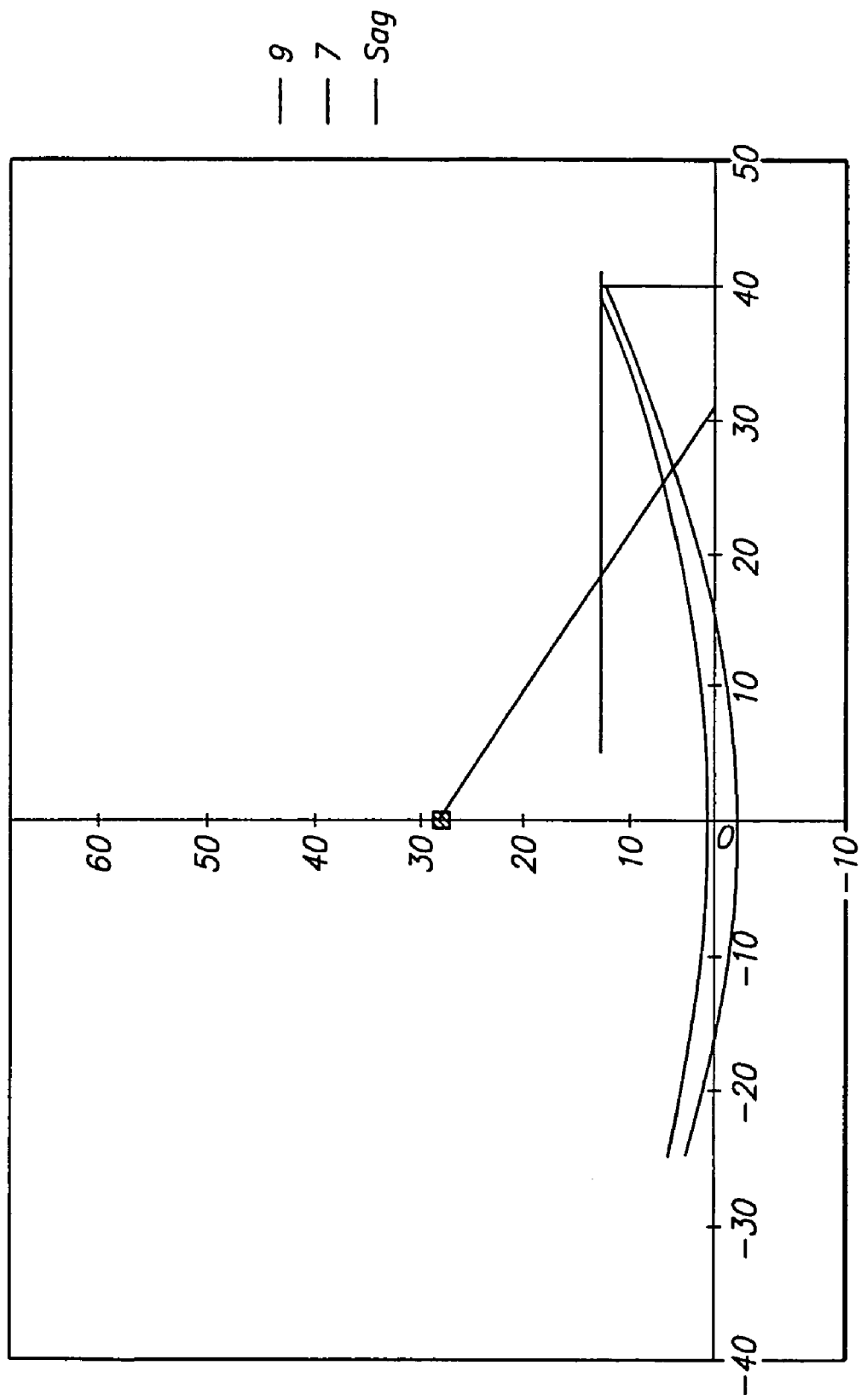

FIG. 21 shows a plus lens of power +2 Dioptres with a piano temporal extension.

Figure 22:
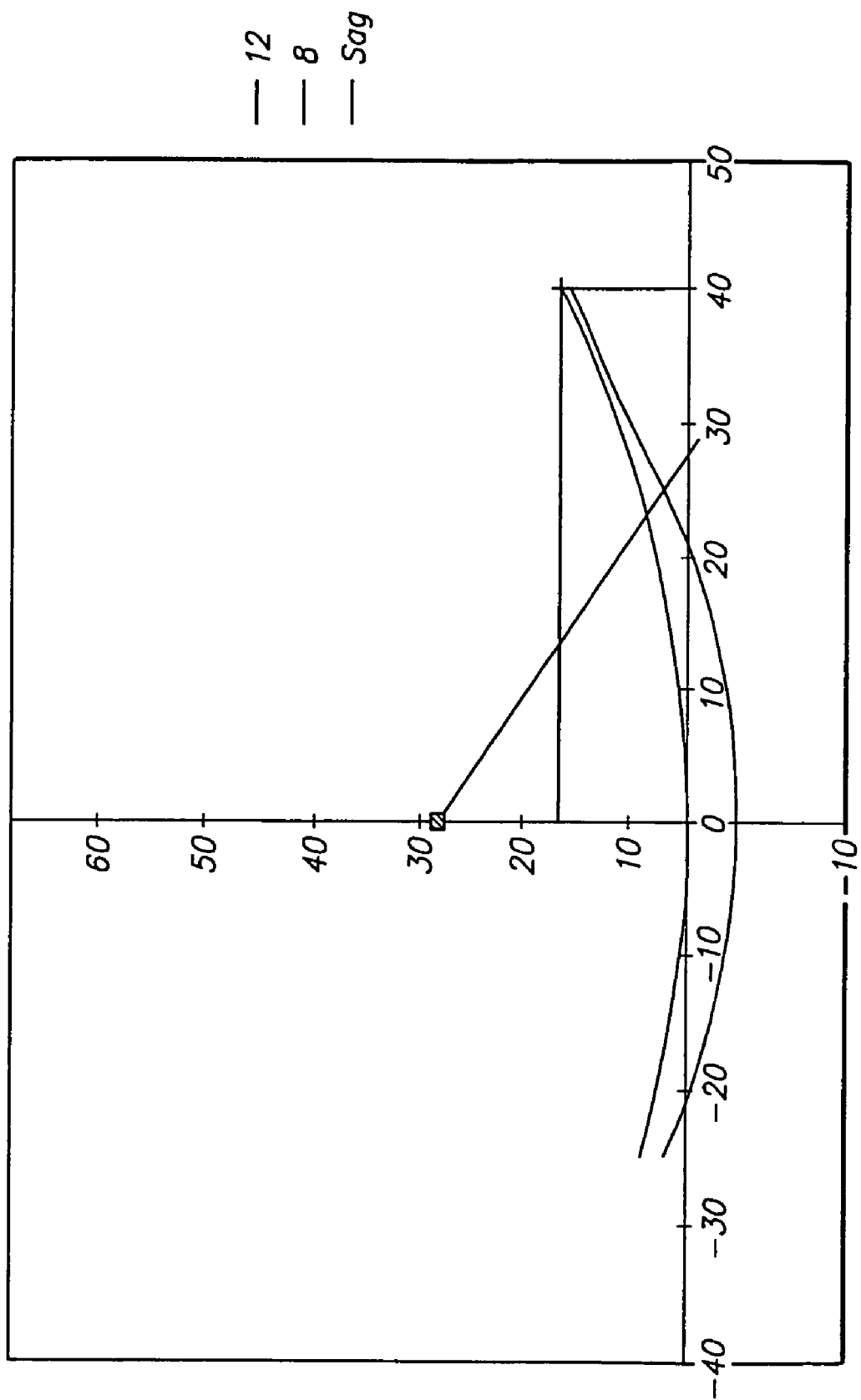
Figure 23:
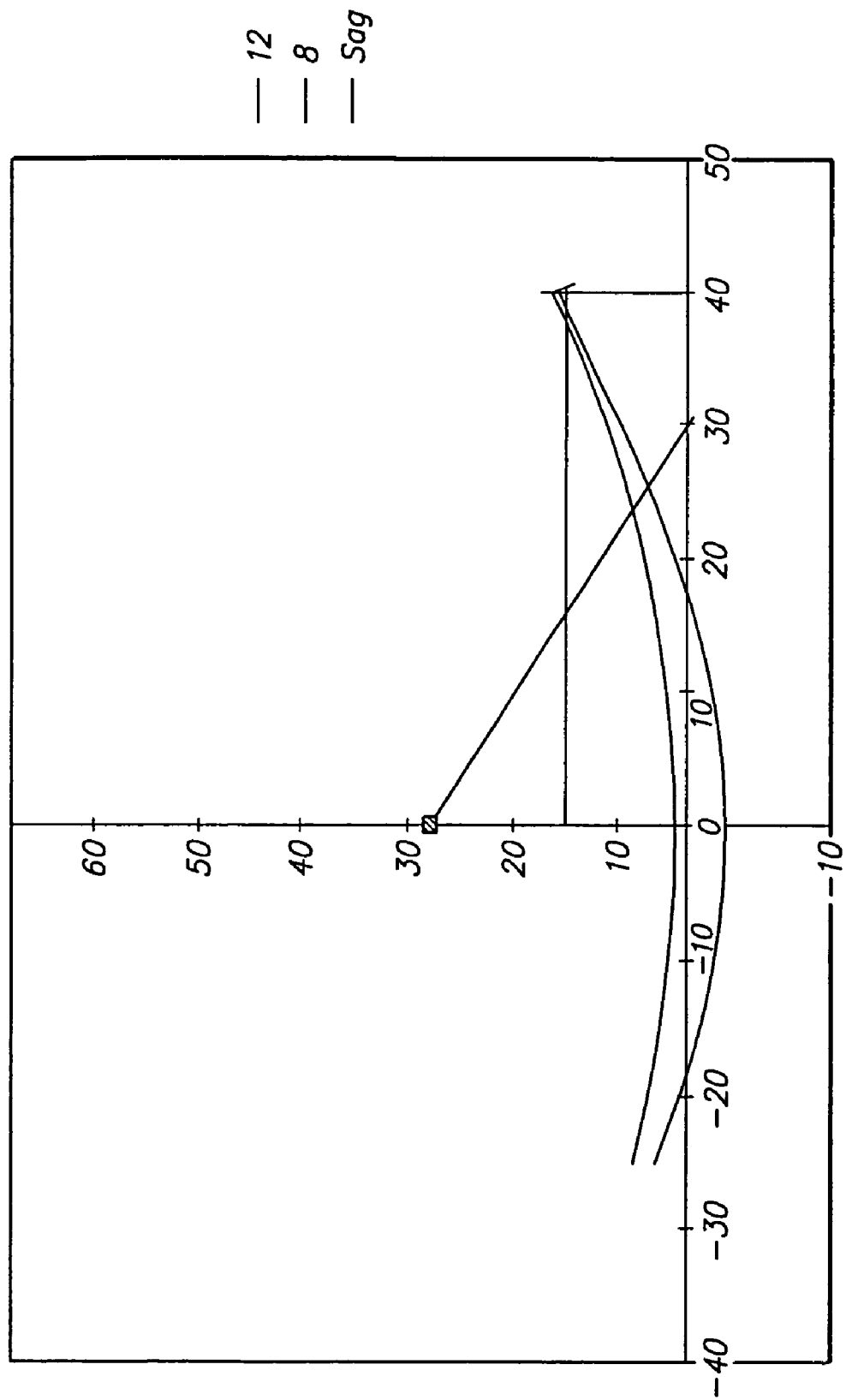

FIGS. 22 and 23 show plus lenses of power +4 Dioptres. That in FIG. 22 has a smooth transition of power to a piano temporal extension, being designed with the parameter N=2. The lens in FIG. 23 has a less desirable discontinuity in front surface power, being designed with the parameter N=1.

Figure 24:
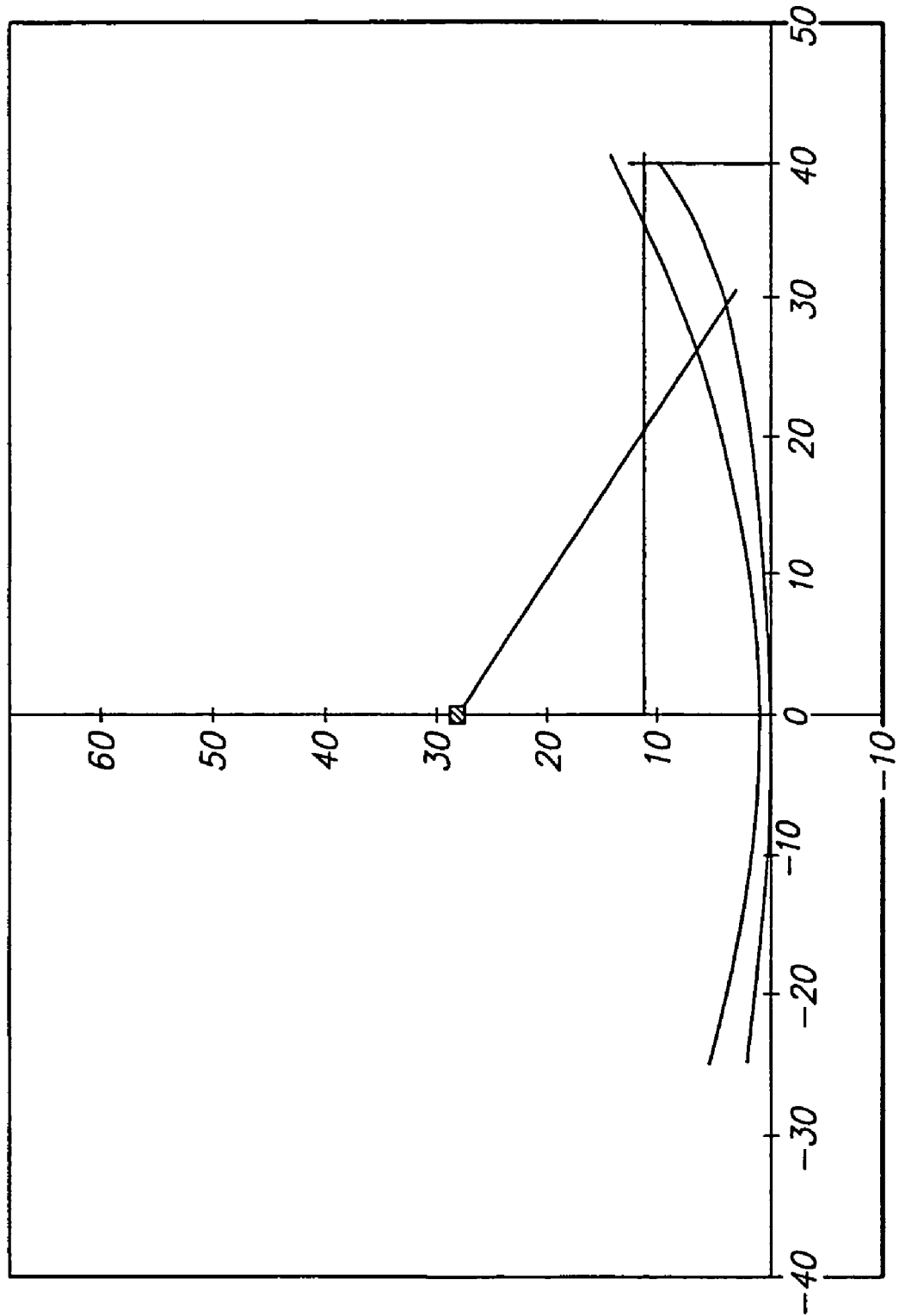
Figure 25:
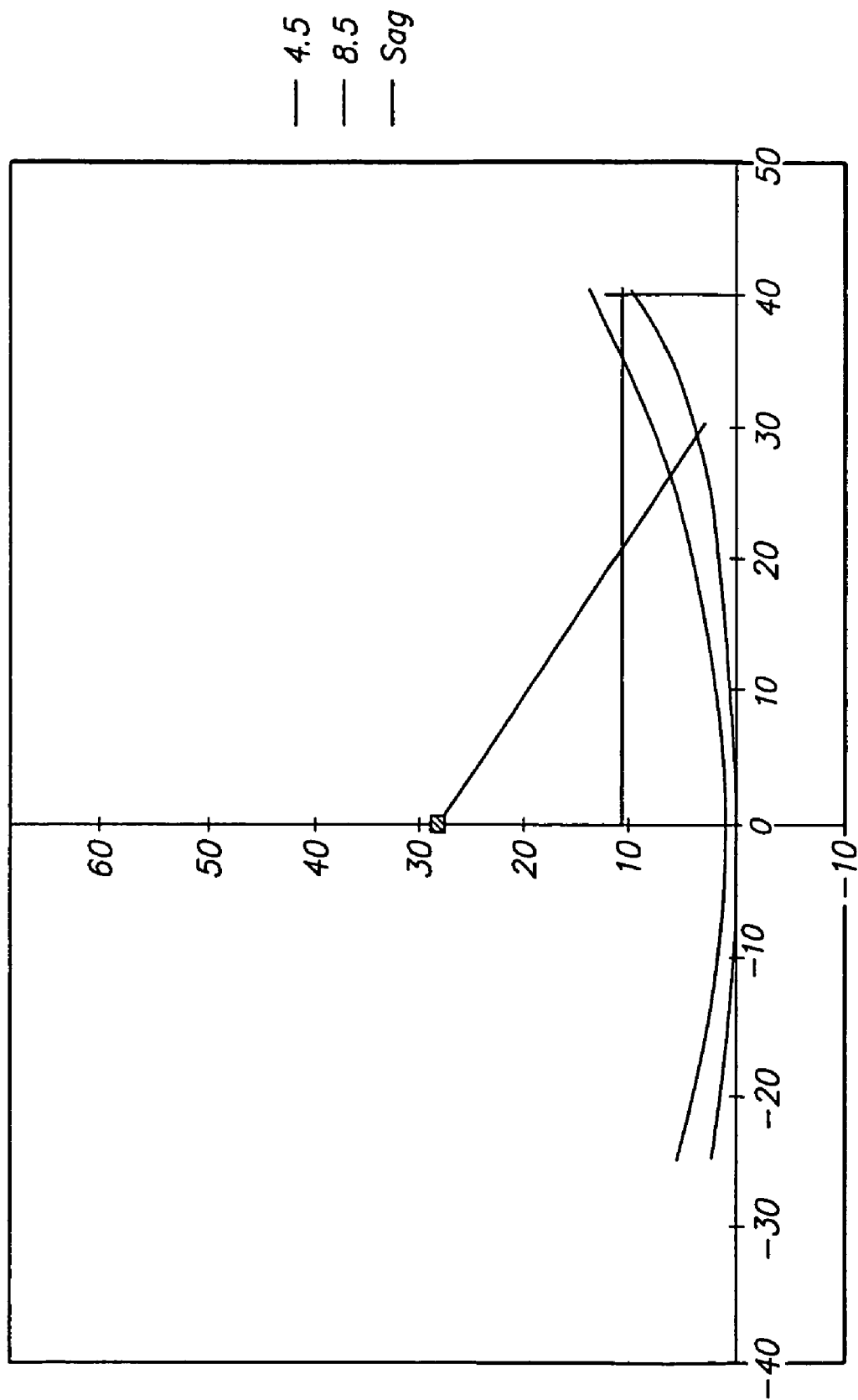

FIGS. 24 and 25 show lenses of power −4 Dioptres. That in FIG. 24 has a smooth transition of power to a piano temporal extension, being designed with the parameter N=2. The lens in FIG. 25 has a less desirable discontinuity in front surface power, being designed with the parameter N=1.

Figure 26:
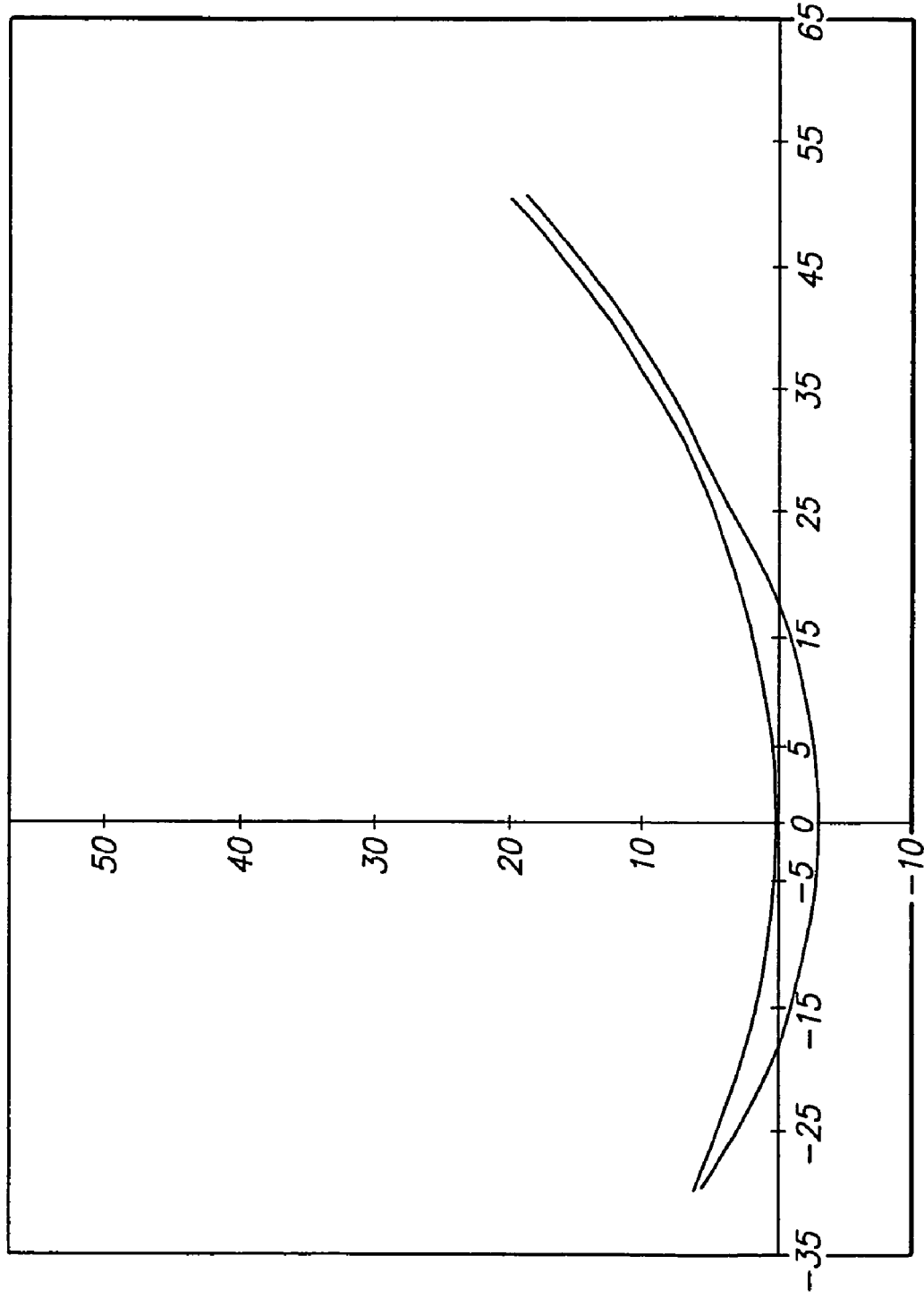
Figure 27:
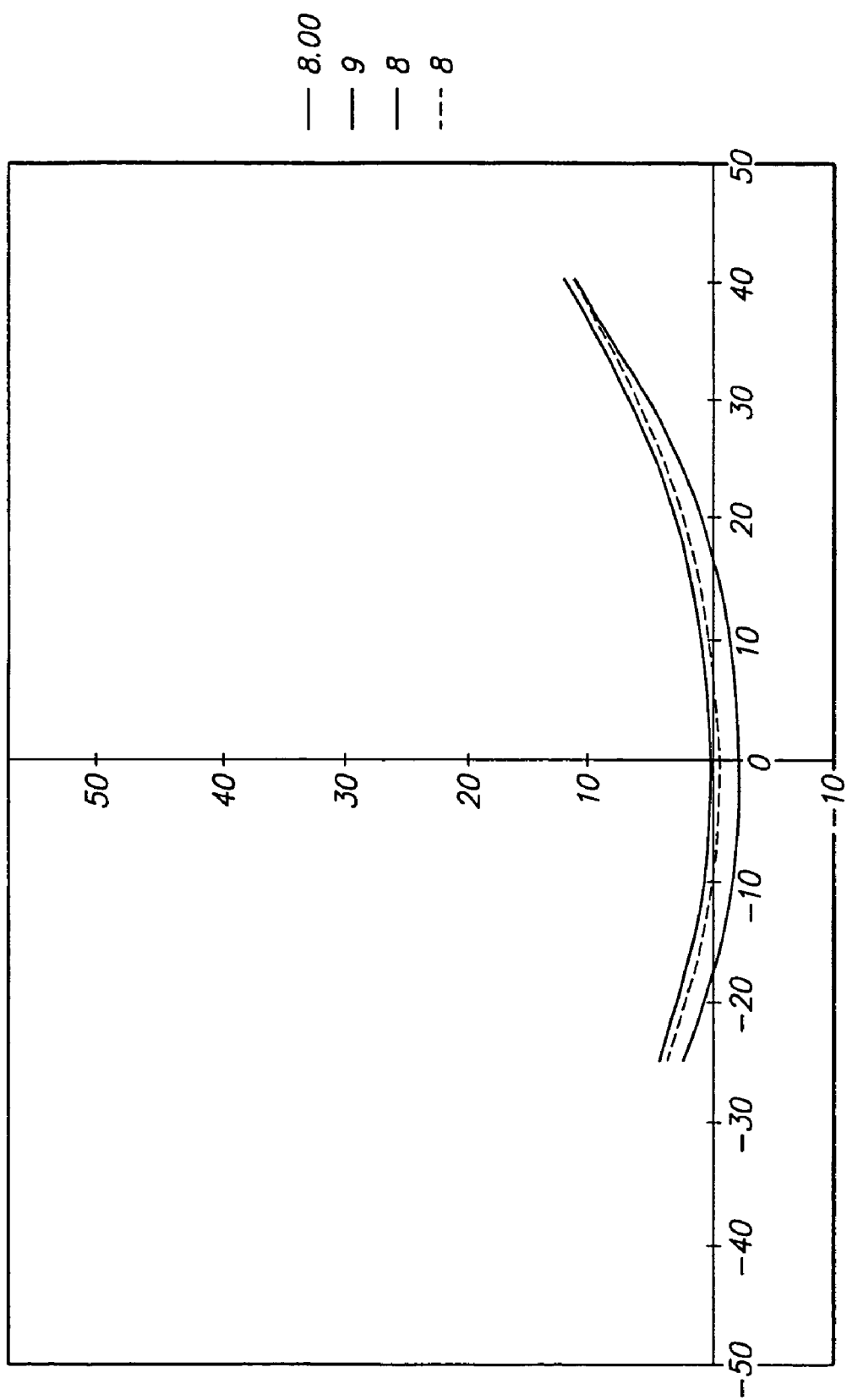
Figure 28:
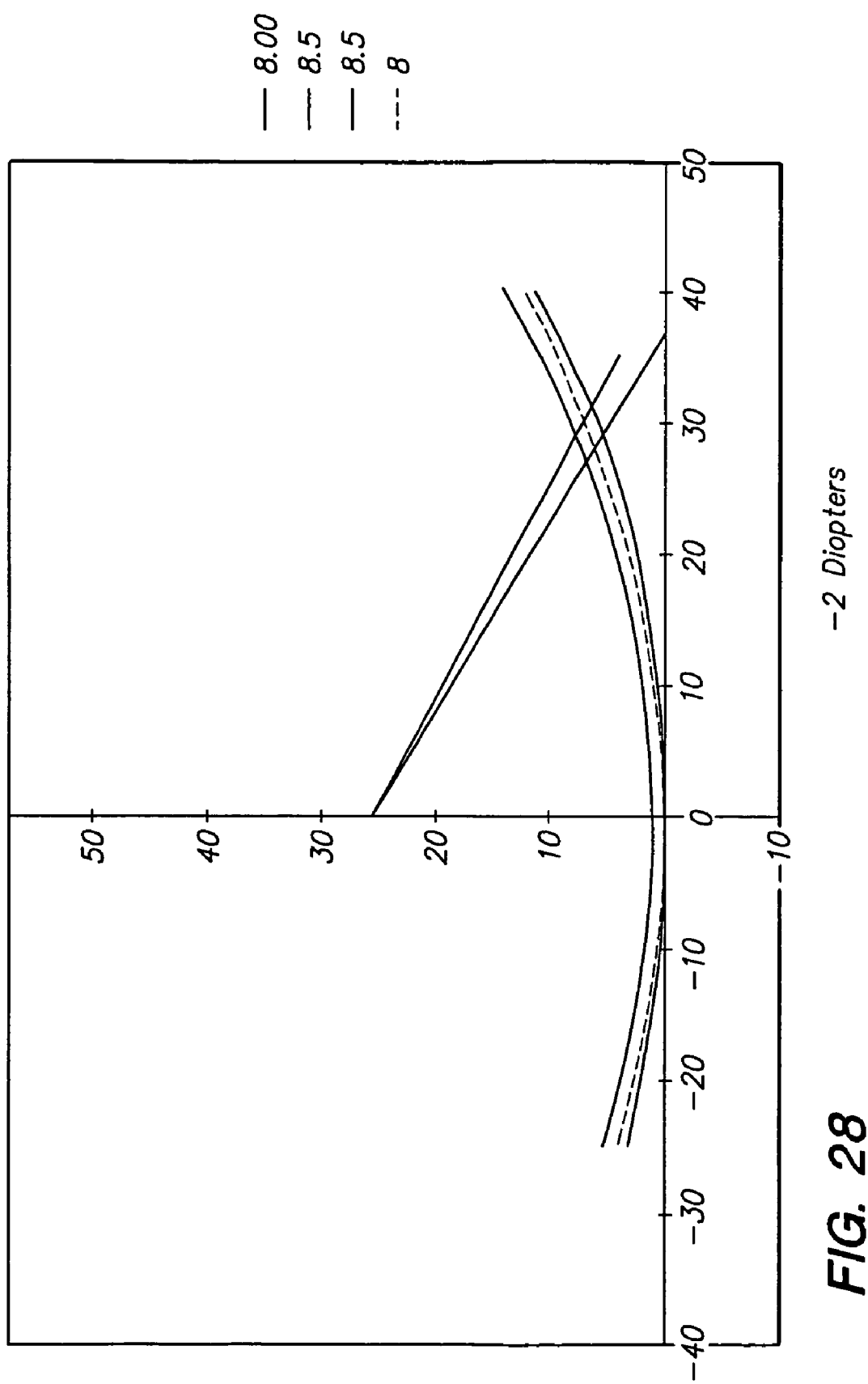

FIGS. 26 to 28 illustrate similar plus and minus optical lens elements created by blending two different surfaces of standard conic design but of different powers corresponding to the optic zone and the temporal extension. Like the lens shown in FIG. 23, these lenses exhibit discontinuity of either tangential or sagittal curvature at the transition between the two design regions. This requires, in turn, that the surface be optimised, so far as is possible, by standard ray tracing techniques in order to minimise the astigmatism and blur introduced by the transitional region between the optic zone and the temporal extension.

Figure 29:
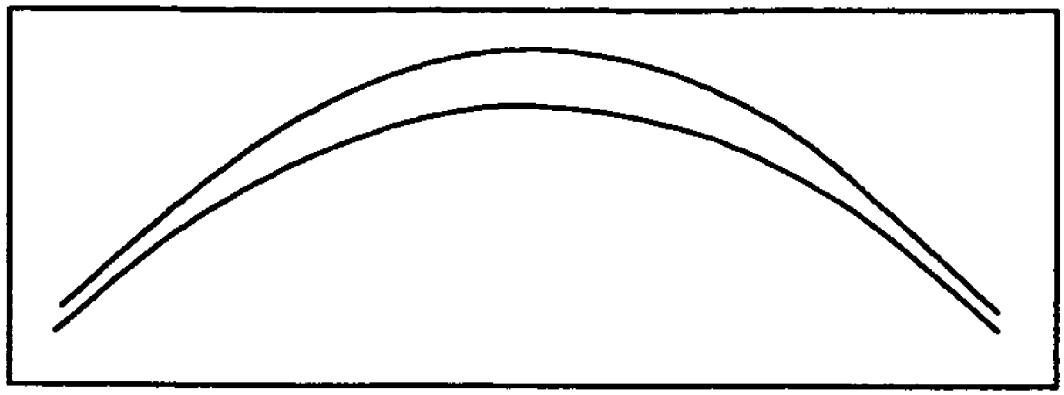
Figure 30:
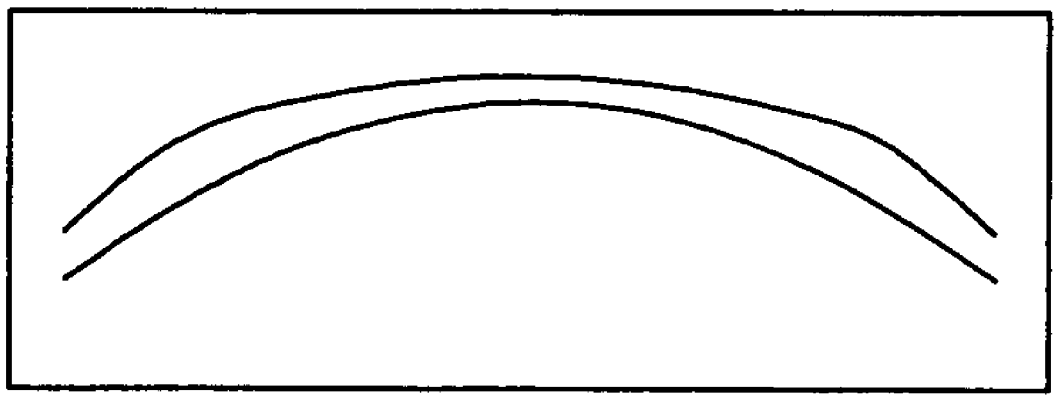

FIGS. 29 and 30 illustrate similar optical plus and minus lens elements including a generally piano temporal extension.

EXAMPLE 1

An ophthalmic lens bearing a minus Rx is produced as follows:

These lenses may be produced as stock lenses or provided via semi-finished blanks, as preferred. For a cast stock lens, the back mould will be unaltered from a conventional back mould for example of the Spectralite type. For a semi-finished blank, the rear ophthalmic surface is ground and polished per standard procedure. In both cases, the principal difference is that the front mould will have a periphery curved sharply to the torus design. A side-fill tube gasket would appear appropriate to both product forms.

A semi-finished (S/F) blank is used normally to supply a range of scripts from each base curve as well as accommodating different pupillary distances (PD's) and different frame shapes and sizes. For all of these lens styles, a specific frame style may be used, so cut lens shape will not vary in a major way. Nevertheless, the S/F blank has to provide for the defined Rx range, the individual PD and the essential temporal extension curve. This curve is steeper the higher the minus script produced and steeper the larger the radius from optical center to temporal edge (i.e. the smaller the PD, all other factors constant).

Figure 4:
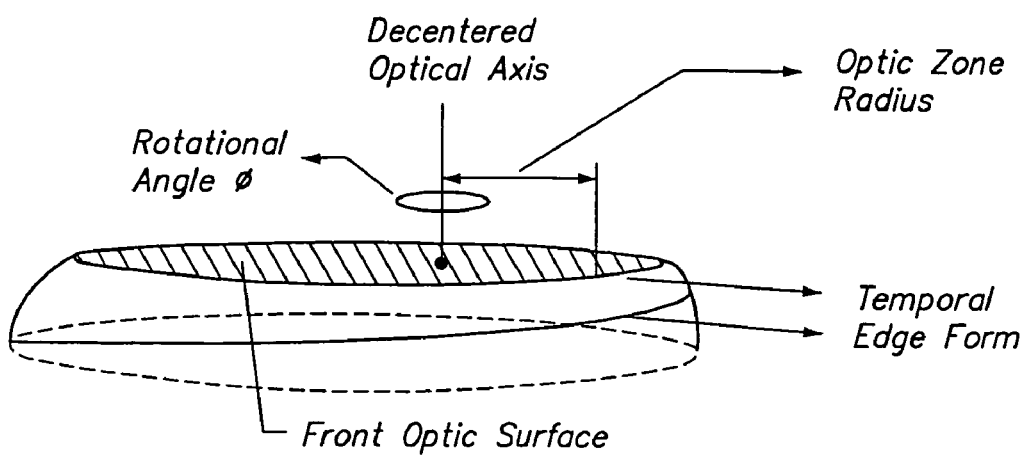
FIG. 4 is a stylised side view of an ophthalmic lens bearing a minus Rx surface according to the present invention.

The geometry of a S/F blank is generally as illustrated in FIG. 4. The front torus curve of the blank extends down the outer edge by at least the depth required for the highest recommended minus power for that nominal base curve (including cylinder). It is not constant at all orientations. Each SIF blank is decentred to allow for a normal spread of PD's. The selection of a particular radius on the blank to be the horizontal meridian of the finished lens will define both the operable PD and the true power of the horizontal meridian. Blanks may be provided with ink markings and alignment callipers to allow correct orientation for surface edging. However edging does not remove the desired temporal curvature.

The optical axis of the optical lens element may be decentered relative to the geometric axis of the lens element. The decentration may function to improve optical performance in the forward direction of vision, whilst maintaining the geometry reguired for mounting in wrap-around frames. Preferable, the optical axis is decentered horizontally relative to the geometric axis of the lens element. Alternatively, or in addition, the optical axis is decentered vertically relative to the geometric axis of the lens element to at least partially compensate for pantoscopic tilt. Where vertical decentration occurs, this may function to ensure that the line of forward sight remains substantially parallel to the plane defined by the design axes of the lens.

A finished spherical power lens series are the exact parallel of the S/F blank sketched above, except that the rear surface are also optically finished.

EXAMPLE 2

An ophthalmic lens similar to that in Example 1 is produced, except that the geometric and optical centers of the lenses are not offset. Such lenses are used with a frame system that allows the PD to be set via the attachment of the lens to the frame supports, rather than by offsetting the geometric and optical centers of the lenses.

EXAMPLE 3

Single point turning apparatus for generation of the required surfaces (both spheres and cyls). Alternatively flexible fining and polishing pads may be used to complete the optic zone surface to a good optical finish and a minimal buffing of the rear temporal "ledge" is sufficient. The torus segment of the resultant lens is translucent although free of generating marks. A gradient mirror coating over this area completes the Rx.

EXAMPLE 4

An ophthalmic lens according to the present invention is laminated from a front and back wafer pair via a conventional lamination system, e.g. the Matrix™ system, U.S. Pat. Nos. 5,187,505, 5,149,181 and 5,323,192 to applicants, the entire disclosure if which is incorporated herein by reference. The interface curve in a laminating system needs to have rotational symmetry about the optical axis in order for the cyl axis to be selected according to the script. Accordingly lens wafers are prepared in which the geometric and optical centres of the lenses are not offset.

Figure 5:
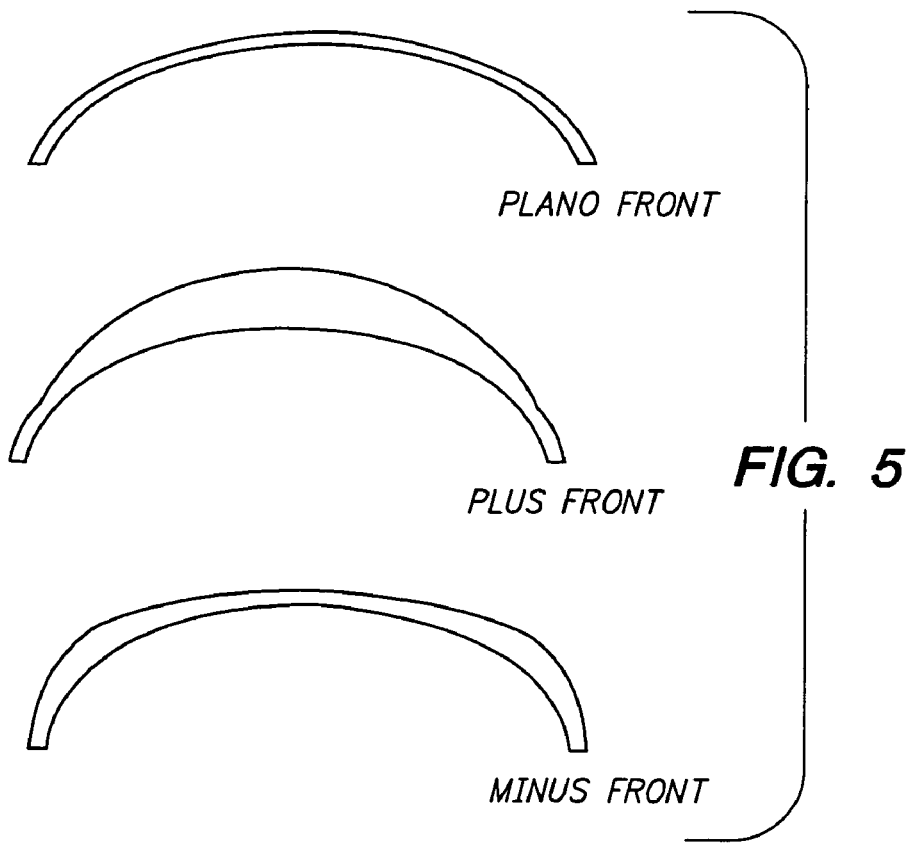
FIG. 5 is a series of cross-sectional views of front surface laminating wafers for piano, plus, and minus lenses according to the present invention. Each front surface is rotationally symmetric.
Figure 6:
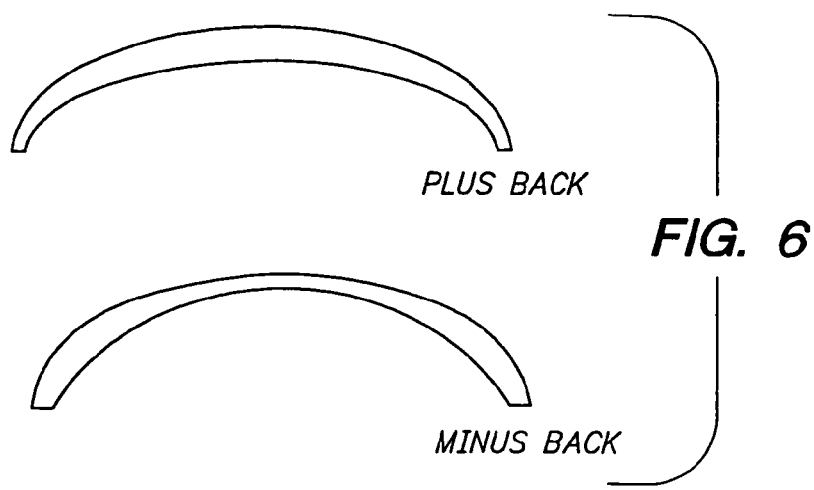
FIG. 6 is a stylised plus and minus back surface wafer for lamination to the front surface wafers illustrated in FIG. 5. Cylinder correction may be carried out on the back surfaces.

The wafers are approximately 80 mm diameter with conventional optics in central zones of about 55 mm diameter with temporal "torus" edges that are more steeply curved. This is illustrated in FIGS. 5 and 6. The temporal extension effect is an excess sag of at least 10 to 15 mm. This is the critical feature of the design concept; asymmetric edging of completed lenses creates the geometry aimed to conform to the brow. The nasal side of the edged lens is fully spherical while elsewhere, the excess sag reaches towards the brow around toward the temple.

EXAMPLE 5

A series of lenses of piano or negative refractive power according to the present invention is produced from a conventional spherical S/F blank of the form shown in FIG. 7(a) by first mounting the front (finished) optical surface of the blank on an eccentric tooling fixture so that the axis of revolution for generating and polishing the rear surface of the blank is offset from the nominal axis of the blank by an angle of (say) 20° or so. Next, an optical surface of exactly the same dioptric power as that of the front surface of the blank but centred on the offset axis is produced on the rear (concave) surface of the blank. This results in a true piano lens with separate optical and geometric axes. The form of the piano lens is reminiscent of a lens to which base-in prism has been applied, as the nasal side of the lens is thicker than the temporal side (FIGS. 8(a), 9(a) and 10(a)). There is strictly no prism applied, only that the piano lens is designed with the same optical precision of any other part of the Rx range. The production of a true piano with properly aligned optical axis is necessary for high base curves for example 9 Dioptres and above, but is generally neglected in lower quality sunglasses.

Next, the piano lens is mounted via its rear surface to rotate eccentrically around the defined axis. Then a desired secondary optical surface centred on this optical axis is generated and polished on the front surface. The power difference between this surface and the original surface is the spherical power of the final Rx, with this newly produced optical surface defining the actual optical zone of the powered lens (FIGS. 7(b) and (c)). The piano portion of the lens surrounding the optical zone provides the temporal extension required for lens according to the invention. This increases as the base curve is increased, shown in FIGS. 7 through 10 for a −4 Dioptre Rx lens. For the examples in the Figures, the temporal extension increases from 88° to 98° temporal with base curve increasing from 8 to 12 Dioptres. The corresponding optic zone widths range from ±35° to ±45° with increasing base curve.

Clearly, the order in which the two optical surfaces are created may be reversed if desired. This is generally the case when it is necessary to apply cylinder to the rear surface for correction of astigmatism.

For plus lenses according to the invention, the front optical surface of the S/F blank does not have a second optical surface imposed upon it. Rather, the rear surface has compound form shown in Figure (11) for +4 Dioptre Rx lenses.

The compound rear surfaces of these lenses, i.e. curves (15)+(16), (17)+(18) and (19)+(20), are generated about the optical axis using computer controlled equipment such as a Coburn IQ generator or one of the several precision optical lathes available to the industry and are polished to ophthalmic requirements by polishing with flexible or inflatable polishing pads, as used in the industry. The optic zone is defined by the central optic on the rear surface of the finished lens. Its breadth ranges from ±35° to ±48° as base curve increases from 8 to 12 Dioptres, whilst the temporal reach grows from 87° to 98°. Clearly, the same technology can be used to create minus power lenses maintaining a simple front curve and designing a compound rear surface to suit. It is also understood that all of the surfaces described here can be imparted a cylindrical component (desirably on the rear curves) to correct astigmatism.

In order to limit the total thickness of plus lenses, it is desirable to minimise the effect of the apparent base-in prism of the true piano lenses at these high base curves. The rear surface of the temporal extension of the plus lenses is therefore made slightly higher in spherical power than the front curve so that the temporal extension is of approximately constant thickness throughout. As a result, the temporal extension has slight negative power, in the order of 0.25 Dioptres for the highest base curves (about 12 Dioptres). Such refractive power is not noticeable to most wearers and we therefore refer to the temporal extension as "pseudo-plano".

All of the lenses described in this example may be produced by casting monomer within moulds shaped to impart the described surface forms after polymerization. In this case, the compound surfaces for both plus and minus Rx lenses are preferably placed at the back of the lens element. Those surfaces are then produced as convex surfaces on the corresponding back mould, facilitating the process of mould manufacture. In such a configuration, plus Rx lenses and minus Rx lenses will have the same front form so that the external appearance of the sunglass will be independent of the prescription of the wearer. Cylinder for the correction of astigmatism may be introduced similarly by appropriately shaped back moulds oriented according to the desired prescription. Alternatively, mild cylinder up to 1.50 Dioptres or so can be imparted by grinding and polishing a secondary curve on the front surface of a lens of the appropriate spherical power. This would suit approximately 95% of cylindrical corrections for most populations.

EXAMPLE 6A

A MINUS LENS

The following is an example that describes a lens element constructed according to the present invention.

A lens was constructed with 0° C. pantoscopic tilt to achieve a prescribed through power of −3.0 D and 0.00 D of cyl using the following curves (see FIG. 12(a)).
 Spherical front curve of 6.00 D (1.530)
 Spherical back curve of 9.18 D (1.530)
 This results in a lens with a distance vision correction such that
 Mean through power=−3.00 D
 Resultant on-axis optical cyl=0.00 D
 Rotate the lens in the temporal direction about the vertical optical axis by 20° (See FIG. 12(a))
 This gives the following optical results
 Mean through power=−3.33 D
 Resultant on-axis optical cyl=0.42 D @ 90°
 FIGS. 13(b) and (c) show the resulting mean surface power and astigmatism contours relative to lens surface coordinates.

EXAMPLE 6B

Full mean power correction.
The back surface curve was adjusted to achieve full correction of the required mean through power of −3.00 D. This results in the following optical results
 Back surface curvature=8.87 D (1.530)
 Mean through power=−3.00 D
 Resultant on-axis optical cyl=0.36 D @ 90°
 FIGS. 12(d) and (e) illustrate the resulting mean power and astigmatism contours relative to lens surface coordinates.

EXAMPLE 6C

Full mean power and full astigmatism toric back surface correction. The back surface curve was adjusted to achieve full correction of the required mean through power of −3.00 D and also a toric back surface correction was applied to result in a full astigmatism correction. This results in the following optical results:
 Mean back surface curvature=8.87 D (1.530)
 Equatorial back surface power=8.69 D (1.530)
 Meridional back surface power=9.05 D (1.530) Toric 0.36 D @ 0°
 Mean through power=−3.00 D
 Resultant on-axis optical cyl=0.00 D
 FIGS. 12(f) and (g) illustrate the resulting mean power and astigmatism contours relative to lens surface coordinates.

EXAMPLE 6D

Full mean power and partial toric back correction.

The back surface curve was adjusted to achieve full correction of the required mean through power of −3.00 D. A partial toric back surface correction was applied to balance the off-axis and on-axis astigmatic errors. This gives the following optical results.

Mean back surface curvature=8.87 D (1.530)
Equatorial back surface power=8.76 D (1.530)
Meridional back surface power=9.00 D (1.530) Toric 0.25 D @ 0°
Mean through power=−3.00 D
Resultant on-axis optical cyl=0.11 D @ 90°

FIGS. 12(h) and (i) illustrate the resulting astigmatism contours and mean power contours relative to lens surface coordinates.

EXAMPLE 6E

Partial mean power and partial toric back correction.

Adjust the central mean through power to partially correct the required through power and reduce the amount of un-accommodatable off-axis power error. A partial toric back surface correction is applied to balance the off-axis and on-axis astigmatic errors. This results in the following optical results:

Mean back surface curvature=9.12 D (1.530)
Equatorial back surface power=8.98 D (1.530)
Meridional back surface power=0.26 D (1.530) Toric 0.27 D @ 0°
Mean through power=−3.25 D
Resultant on-axis optical cyl=0.12 D @ 90°

FIGS. 12(j) and (k) illustrate the resulting astigmatism contours and mean power contours relative to lens surface coordinates.

EXAMPLE 7A

A Plus Lens

The following is an example that describes a lens constructed according to the present invention.

Construct a lens with 0° C. pantoscopic tilt to achieve a prescribed through power of +3.0 D and 0.00 D of cyl using the following curves (see FIG. 13(a)).

Spherical front curve of 6.00 D (1.530)
Spherical back curve of 2.92 D (1.530)

This results in a lens with a distance vision correction such that

Mean through power=+3.00 D
Resultant on axis optical cyl=0.00 D

Rotate the lens in the temporal direction about the vertical optical axis by 20° (see FIG. 13(a)).

This gives the following optical results
Mean through power=+3.36 D
Resultant on axis optical cyl=0.46 D @ 90°

FIGS. 13(b) and (c) show the resulting mean power and astigmatism contours relative to lens surface coordinates.

EXAMPLE 7B

Full mean power correction.

The back surface curve was adjusted to achieve full correction of the required mean through power of +3.00 D. This results in the following optical results Spherical front curvature=6.00 D (1.530)
Back surface curvature=3.23 D (1.530)
Mean through power=+3.00 D
Resultant on axis optical cyl=0.41 D @ 90°

FIGS. 13(d) and (e) illustrate the mean power and resulting astigmatism contours relative to lens surface coordinates.

EXAMPLE 7C

Full mean power and full astigmatism toric front surface correction. The back surface curve was adjusted to achieve full correction of the required mean through power of +3.00 D and also a toric front surface correction was applied to result in a full astigmatism correction. This results in the following optical results:

Mean back surface curvature=3.32 D (1.530)
Equatorial front surface power=5.82 D (1.530)
Meridional front surface power=6.18 D (1.530) Toric 0.36 D @ 0°
Mean through power=+3.00 D
Resultant on axis optical cyl=0.00 D FIGS. 13(f) and (g) illustrate the mean power and resulting astigmatism contours relative to lens surface coordinate.

EXAMPLE 7D

Full mean power and partial toric front correction.

The back surface curve was adjusted to achieve full correction of the required mean through power of +3.00 D. A partial toric front surface correction was applied to balance the off-axis and on-axis astigmatic errors. This gives the following optical results:

Mean back surface curvature=3.32 D (1.530)
Equatorial front surface power=5.91 D (1.530)
Meridional front surface power=6.09 D (1.530) Toric 0.18 D @ 0°
Mean through power=+3.00 D
Resultant on axis optical cyl=0.22 D @ 90°

FIGS. 13(h) and (i) illustrate the mean power and resulting astigmatism contours and mean power contours relative to lens surface coordinates.

EXAMPLE 8

Aspheric Minus Lens

Aspheric front surface and toric back surface corrected (see FIG. 14(a))

The back surface was adjusted to achieve full correction of the required mean through power of −3.00 D and also a toric back surface correction was applied to result in a full astigmatic correction in a manner similar to Example 6C above.

An aspheric front surface correction was applied to reduce off-axis astigmatic and power errors.

This results in the following optical results:
Mean back surface curvature=9.05 D (@ 1.530)
Equatorial front surface power=8.67 D (§ 1.530)
Meridional front surface power=9.05 D (@ 1.530)
Mean through power=−3.00 D
Resultant on axis optical cyl=0.00 D Aspheric Front Surface The height of the front surface at a radius, r, is given by the formula:

$$Z = a_0 r^0 + a_1 r^1 + a_2 r^2 + a_3 r^3 + a_4 r^4 + a_5 r^5 + a_6 r^6 + a_7 r^7 + a_8 r^8$$

where $a_0$ to $a_8$ are constant numerical coefficients.

Base curve=6.00 D $a_0=a_1=a_3=a_5=a_{7=0.0}$
$a_2=0.5660377\times10^{-2}$
$a_4=-0.19050\times10^{-6}$
$a_6=0.65054\times10^{-10}$
$a_8=-0.17067\times10^{-13}$ FIGS. 14(*b*) and (*c*) illustrate the resulting mean power and astigmatism contours relative to lens surface co-ordinates.

EXAMPLE 9

Aspheric Surface Lens Element

An optical lens element including a peripheral temporal zone was formed from a front 9 base aspheric piano element and a number of rear spherical plus lens elements laminated to the rear surface thereof.

The surfaces are defined utilising a standard mathematical approach. The surfaces have the characteristics specified in Table 1 below.

The resulting lens element is illustrated schematically in FIG. 15.

EXAMPLE 10

Example 9 was repeated utilising rear lens elements of the same refractive power (+4 and +6 Dioptres) but of reduced diameter. The optic zone of each is reduced in angular extent, while the overall laminated lenses are substantially thinner.

The surfaces are defined utilising a standard mathematical approach. The surfaces have the characteristics specified in Table 2 below.

The resulting lens element is illustrated schematically in FIG. 16.

EXAMPLE 11

Example 9 was repeated utilising rear lens elements of −4 and −8 Dioptre refractive power, wherein the edges of these elements were angled parallel to the line of sight at those edges, or more steeply, so that the wearer experiences a sudden change from the optic zone to the piano temple extension without any intermediate optical transition or distortion.

The surfaces are defined utilising a standard mathematical approach. The surfaces have the characteristics specified in Table 3 below.

The resulting lens element is illustrated schematically in FIG. 17.

EXAMPLE 12

An optical lens element including a peripheral temporal zone was formed from a front 9D base aspheric front surface together a rear −4D and −8D base spherical rear surface. The rear surface may be formed either by lamination as described in example 1 above or may be integrally formed by cutting on an NC mill or on standard optical processing equipment with an additional final polishing step to round off the sharp edge which would otherwise exist at the boundary of the optic zone and the integral temple extension.

The surfaces are defined utilising a standard mathematical approach. The surfaces have the characteristics specified in Table 4 below.

The resulting lens element is illustrated schematically in FIG. 18.

EXAMPLE 13

Torus Surface Lens Element

An optical lens element is formed utilising a circular front surface and conic rear surfaces with a modified piano temporal extension.

The front or rear surfaces may be formed from front and rear lens elements laminated together or may be integrally formed by cutting on an NC mill.

The surfaces are defined utilising the modified mathematical formulae described above.

The surfaces have the characteristics specified in Table 5 below.

The resulting lens element is illustrated schematically in FIG. 19.

A similar lens element to that in FIG. 19 has the characteristics specified in Table 6 below.

It is noteworthy that the front piano described in this example has an optic zone and a temporal region of high curvature which together define a piano lens with essentially constant thickness from the central region through and including the temporal extension. This is an alternative and different approach to achieving the piano sunglass or safety glass lens attributes described in U.S. Pat. No. 5,604,547 to Gentex.

A further aspheric front surface correction was applied to eliminate off-axis astigmatic and power errors within the piano element, similarly to Example 8 above. This gave the following:

Central Front Curve=9.0 D (@ 1.4999)

Mean Through power=$0\times10^{-2}$ D

Resultant on axis optical cyl=$0.1\times10^{-2}$ D

Maximum off-axis cyl=0.2 D

For which the constant numerical coefficients were $a_0=a_1=a_2=a_3=a_5=a_7=0.0$
$a_2=0.849057\times10^{-2}$
$a_4=0.610000\times10^{-6}$
$a_6=0.150000\times10^{-9}$

EXAMPLE 14

Example 13 was repeated utilising 9 D design for the front surface of the optic zone and a 7 D circular back surface to define an integral lens element of through power +2 D. The front generating curve for the temporal extension was 4.5 D and resulted in a temporal zone with slight positive refractive power.

The surfaces are defined utilising the modified mathematical approach described above with N=2 and a negative value for the parameter α (−1.2). The surfaces have the characteristics specified in Table 7 below.

The resulting lens element is illustrated schematically in FIG. 21

Obviously the lens element may be rotated or decentred to improve cosmetic relationship with a wearer's face without the need to introduce higher lens curvature.

EXAMPLE 15

Example 14 was repeated utilising a front surface of 12.00 D for the optic zone and a back surface of 8.00 D to define an integral lens element of +4.00 D through power. The front generating curve for the temporal extension was 4.25 D.

The resulting lens element is illustrated in FIG. 22 and its surface characteristics are specified in Table 8. In this case the temporal extension changes smoothly from the power of the optic zone (+4.00 D) to piano.

EXAMPLE 16

Example 15 was again repeated utilising a front generating curve for the temporal extension of 12.00 D and setting N=1, rather than N=2 in the previous example of FIG. 22.

The resulting lens element is illustrated in FIG. 23 and its surface characteristics are specified in Table 9. In this case, the temporal extension is piano, the diameter of the optic zone is reduced.

EXAMPLE 17

Example 14 was repeated utilising a front surface of 4.50 D for the optic zone and a back surface of 8.50 D to define an integral lens element of −4.00 D through power. The front generating curve for the temporal extension was 2.50 D.

The resulting lens element is illustrated in FIG. 24 and its surface characteristics are specified in Table 10. In this case the temporal extension changes smoothly from the power of the optic zone (−4.00 D) to piano.

EXAMPLE 18

Example 17 was again repeated utilising a front generating curve for the temporal extension of 11.00 D and setting N=1, rather than N=2 in the previous example of FIG. 24.

The resulting lens element is illustrated in FIG. 25 and its surface characteristics are specified in Table 11. In this case, the temporal extension is piano, the lens has a thinner centre and the diameter of the optic zone is reduced.

EXAMPLE 19

Plus Lens

Example 14 was repeated utilising a front generating curve for the temporal extension of 8.00 D. A conic back surface of 8.0 D and a front surface of 11.0 D was used to define a lens of through power of +3.0 D and a generally piano temporal extension with a narrow edge thickness.

The resulting lens is illustrated in FIG. 26. The lens exhibits a discontinuity at the transition between the two design zones. The surface of FIG. 26 has the characteristics specified in Table 12.

EXAMPLE 20

Example 19 was repeated to produce a +1.0 D lens with an 8.0 D base temporal extension.

The resulting lens is illustrated in FIG. 27. The surface of FIG. 27 has the characteristics specified in Table 13.

EXAMPLE 21

Example 19 was repeated to produce a −2.0 D lens with an 8.0 D base temporal extension.

The resulting lens is illustrated in FIG. 28. The surface of FIG. 28 has the characteristics specified in Table 14.

EXAMPLE 22

An optical lens element including a peripheral temporal zone was formed from a front +11 D base aspheric front surface and an +8 D base spherical back surface to provide a +3 D lens element.

The curvature in the temporal region of the front surface is modified such that it corresponds to the curvature of the back surface, thus defining a piano temporal extension.

The surfaces are designed utilising the modified mathematical formulae described above. Specifically, the lens element has a spherical or toric back surface whose curvature is chosen to conform with the wrap-around frame. The front surface of the lens element is an aspheric surface with three distinct zones. The central prescription region is developed to provide the desired through power and is optimised to minimise off-axis astigmatic and power errors. The front surface of the lens element at the periphery or temporal extension region is a sphere designed to give the lens in this region no through power (piano) as in a non-prescription sunlens. Between the inner and outer region the surface is developed from a polynomial spline whose purpose is to smoothly blend the central region with the periphery. Although the surface is designed as a full surface of rotation, only a portion of this surface is used in the actual frame. Accordingly the lens form may be manufactured in such a way that only part of the full surface of rotation is created prior to edging to fit the frame.

The surfaces have the characteristics specified in Table 15 below.

The resulting lens element is illustrated schematically in FIG. 29.

EXAMPLE 23

Example 22 was repeated utilising a 5.0 D base aspherical front surface and an 8.0 D base spherical back surface to define a −3 D base lens element.

The surfaces have the characteristics specified in Table 16 below.

The resulting lens element is illustrated in FIG. 30.

TABLE 1

| | | | Polycarbonate ASL | | | | |
|---|---|---|---|---|---|---|---|
| | B | A2 | A4 | A6 | A8 | r | D |
| ASPHERE | 8 | 7.60E−03 | 3.00E.07 | 7.00E−11 | 0.00E+00 | 65.75 | 8.97 |
| SPHERES | 3 | 2.54E−03 | 1.64E−08 | 2.12E−13 | 3.43E−18 | 196.67 | 3.00 |
| | 5 | 4.24E−03 | 7.61E−08 | 2.73E−12 | 1.23E−16 | 118.00 | 5.00 |
| | 8.97 | 7.60E−03 | 4.39E−07 | 5.08E−11 | 7.33E−15 | 65.77 | 8.97 |

| R | 8ASL | 3 | 5 | 8.97 |
|---|---|---|---|---|
| −50 | | | | |
| −45 | | | | |
| −40 | | | | |
| −35 | | | | |
| −30 | 7.138 | | 8.740 | 8.739 |
| −25 | 4.887 | 6.436 | 7.542 | 6.436 |
| −20 | 3.094 | 5.861 | 6.570 | 4.614 |
| −20 | 3.094 | 5.861 | 6.570 | 4.614 |
| −15 | 1.727 | 5.414 | 5.820 | 3.233 |
| −10 | 0.763 | 5.095 | 5.287 | 2.265 |
| −5 | 0.190 | 4.905 | 4.969 | 1.690 |
| 0 | 0.000 | 4.841 | 4.863 | 1.500 |
| 5 | 0.190 | 4.905 | 4.969 | 1.690 |
| 10 | 0.763 | 5.095 | 5.287 | 2.265 |
| 15 | 1.727 | 5.414 | 5.820 | 3.233 |
| 20 | 3.094 | 5.861 | 6.570 | 4.614 |
| 25 | 4.887 | 6.436 | 7.542 | 6.436 |
| 30 | 7.138 | | 8.740 | 8.739 |
| 35 | 9.894 | | | 11.581 |
| 40 | 13.221 | | | 15.043 |
| 45 | 17.210 | | | 19.240 |

TABLE 2

| | | | Polycarbonate ASL | | | | |
|---|---|---|---|---|---|---|---|
| | B | A2 | A4 | A6 | A8 | r | D |
| ASPHERE | 8 | 7.60E−03 | 3.00E.07 | 7.00E−11 | 0.00E+00 | 65.75 | 8.97 |
| SPHERES | 3 | 2.54E−03 | 1.64E−08 | 2.12E−13 | 3.43E−18 | 196.67 | 3.00 |
| | 5 | 4.24E−03 | 7.61E−08 | 2.73E−12 | 1.23E−16 | 118.00 | 5.00 |
| | 8.97 | 7.60E−03 | 4.39E−07 | 5.08E−11 | 7.33E−15 | 65.77 | 8.97 |

| R | 8ASL | 3 | 5 | 8.97 |
|---|---|---|---|---|
| −50 | | | | |
| −45 | | | | |
| −40 | | | | |
| −35 | | | | |
| −30 | 7.138 | | | 8.739 |
| −25 | 4.887 | | 6.179 | 6.436 |
| −20 | 3.094 | 4.520 | 5.207 | 4.614 |
| −20 | 3.094 | 4.520 | 5.207 | 4.614 |
| −15 | 1.727 | 4.073 | 4.457 | 3.233 |
| −10 | 0.763 | 3.754 | 3.924 | 2.265 |
| −5 | 0.190 | 3.564 | 3.606 | 1.690 |
| 0 | 0.000 | 3.500 | 3.500 | 1.500 |
| 5 | 0.190 | 3.564 | 3.606 | 1.690 |
| 10 | 0.763 | 3.754 | 3.924 | 2.265 |
| 15 | 1.727 | 4.073 | 4.457 | 3.233 |
| 20 | 3.094 | 4.520 | 5.207 | 4.614 |
| 25 | 4.887 | | 6.179 | 6.436 |
| 30 | 7.138 | | | 8.739 |
| 35 | 9.894 | | | 11.581 |
| 40 | 13.221 | | | 15.043 |
| 45 | 17.210 | | | 19.240 |

TABLE 3

Polycarbonate ASL

|  | B | A2 | A4 | A6 | A8 | r | D |
|---|---|---|---|---|---|---|---|
| ASPHERE | 8 | 7.60E-03 | 3.00E.07 | 7.00E-11 | 0.00E+00 | 65.75 | 8.97 |
| SPHERES | 17 | 1.44E-02 | 2.99E-06 | 1.24E-09 | 6.44E-13 | 34.71 | 17.00 |
|  | 13 | 1.10E-02 | 1.34E-06 | 3.25E-10 | 9.85E-14 | 45.38 | 13.00 |
|  | 8.97 | 7.60E-03 | 4.39E-07 | 5.08E-11 | 7.33E-15 | 65.77 | 8.97 |

| R | 8ASL | 17 | 13 | 8.97 |
|---|---|---|---|---|
| -50 |  |  |  |  |
| -45 |  |  |  |  |
| -40 |  |  |  |  |
| -35 |  |  |  |  |
| -30 | 7.138 |  | 12.800 | 8.239 |
| -25 | 4.887 |  | 9.002 | 5.936 |
| -20 | 3.094 | 7.758 | 6.144 | 4.114 |
| -20 | 3.094 | 7.837 | 6.144 | 4.114 |
| -15 | 1.727 | 4.909 | 4.050 | 2.733 |
| -10 | 0.763 | 2.972 | 2.615 | 1.765 |
| -5 | 0.190 | 1.862 | 1.776 | 1.190 |
| 0 | 0.000 | 1.500 | 1.500 | 1.000 |
| 5 | 0.190 | 1.862 | 1.776 | 1.190 |
| 10 | 0.763 | 2.972 | 2.615 | 1.765 |
| 15 | 1.727 | 4.909 | 4.050 | 2.733 |
| 20 | 3.094 | 7.837 | 6.144 | 4.114 |
| 25 | 4.887 |  | 9.002 | 5.936 |
| 30 | 7.138 |  | 12.800 | 8.239 |
| 35 | 9.894 |  |  | 11.081 |
| 40 | 13.221 |  |  | 14.543 |
| 45 | 17.210 |  |  | 18.740 |

TABLE 4

Polycarbonate ASL

|  | B | A2 | A4 | A6 | AB | r | D |
|---|---|---|---|---|---|---|---|
| ASPHERE | 8 | 7.60E-03 | 3.00E.07 | 7.00E-11 | 0.00E+00 | 65.75 | 8.97 |
| SPHERES | 17 | 1.44E-02 | 2.99E-06 | 1.24E-09 | 6.44E-13 | 34.71 | 17.00 |
|  | 13 | 1.10E-02 | 1.34E-06 | 3.25E-10 | 9.85E-14 | 45.38 | 13.00 |
|  | 8.97 | 7.60E-03 | 4.39E-07 | 5.08E-11 | 7.33E-15 | 65.77 | 8.97 |

| R | 8ASL | 17 | 13 | 8.97 |
|---|---|---|---|---|
| -50 |  |  |  |  |
| -45 |  |  |  |  |
| -40 |  |  |  |  |
| -35 |  |  |  |  |
| -30 | 7.138 | 10.733 | 10.794 | 8.329 |
| -25 | 4.887 | 9.038 | 9.002 | 5.936 |
| -20 | 3.094 | 7.758 | 6.144 | 4.114 |
| -15 | 1.727 | 4.909 | 4.050 | 2.733 |
| -10 | 0.763 | 2.972 | 2.615 | 1.765 |
| -5 | 0.190 | 1.862 | 1.776 | 1.190 |
| 0 | 0.000 | 1.500 | 1.500 | 1.000 |
| 5 | 0.190 | 1.862 | 1.776 | 1.190 |
| 10 | 0.763 | 2.972 | 2.615 | 1.765 |
| 15 | 1.727 | 4.101 | 4.050 | 2.733 |
| 20 | 3.094 | 7.837 | 6.144 | 4.114 |
| 25 | 4.887 | 9.038 | 9.002 | 5.936 |
| 30 | 7.138 | 10.733 | 10.794 | 8.239 |
| 35 | 9.894 | 12.872 | 12.997 | 11.081 |
| 40 | 13.221 | 16.117 | 15.821 | 14.543 |
| 45 | 17.210 | 19.360 | 19.378 | 18.740 |

TABLE 5

Highly Curved Wrap Around Plano Lens Element

|  | B | A2 | A4 | A6 | A8 | r | D |
|---|---|---|---|---|---|---|---|
| Front Asphere | 9 | 7.60E−03 | 3.00E−07 | 7.00E−11 | 0.00E+00 | 65.75 | 8.97 |
| Back | 9 | 7.63E−03 | 4.44E−07 | 5.16E−11 | 7.51E−15 | 65.56 | 9.00 |
| Temples | 20 | 0.00E+00 | 4.87E−07 | 2.80E−09 | 2.01E−12 |  | 0.00 |

$$\text{Sag} = \text{SAG} + \alpha\, \text{SAG}^N$$

| R0 | R | θ | Sag1 | Sag2 | α1 | N | α2 |
|---|---|---|---|---|---|---|---|
| −22.5 |  |  |  |  | 12 | 1 | 15 |
| −22.5 |  |  |  |  | 12 | 1 | 15 |
| −22.5 |  |  |  |  | 12 | 1 | 15 |
| −22.5 | −35 | 9.894 | 11.463 | 13.542 | 12 | 1 | 15 |
| −22.5 | −30 | 7.138 | 7.329 | 8.978 | 12 | 1 | 15 |
| −22.5 | −25 | 4.887 | 4.889 | 6.439 | 12 | 1 | 15 |
| −22.5 | −20 | 3.094 | 3.094 | 4.625 | 12 | 1 | 15 |
| −22.5 | −20 | 3.094 | 3.094 | 4.625 | 12 | 1 | 15 |
| −22.5 | −15 | 1.727 | 1.727 | 3.239 | 12 | 1 | 15 |
| −22.5 | −10 | 0.763 | 0.763 | 2.267 | 12 | 1 | 15 |
| −22.5 | −5 | 0.190 | 0.190 | 1.691 | 12 | 1 | 15 |
| −22.5 | 0 | 0.000 | 0.000 | 1.500 | 12 | 1 | 15 |
| 22.5 | 5 | 0.190 | 0.190 | 1.691 | 12 | 1 | 15 |
| 22.5 | 10 | 0.763 | 0.763 | 2.267 | 12 | 1 | 15 |
| 22.5 | 15 | 1.727 | 1.727 | 3.239 | 12 | 1 | 15 |
| 22.5 | 20 | 3.094 | 3.094 | 4.625 | 12 | 1 | 15 |
| 22.5 | 25 | 4.887 | 4.889 | 6.439 | 12 | 1 | 15 |
| 22.5 | 30 | 7.138 | 7.329 | 8.978 | 12 | 1 | 15 |
| 22.5 | 35 | 9.894 | 11.463 | 13.582 | 12 | 1 | 15 |
| 22.5 | 40 | 13.221 | 19.877 | 23.420 | 12 | 1 | 15 |

TABLE 6

Highly Curved Wrap Around Plano Lens Element

|  | B | A2 | A4 | A6 | A8 | r | D |
|---|---|---|---|---|---|---|---|
| Front Asphere | 9 | 7.60E−03 | 3.00E−07 | 7.00E−11 | 0.00E+00 | 65.75 | 8.97 |
| Back | 9 | 7.63E−03 | 4.44E−07 | 5.16E−11 | 7.51E−15 | 65.56 | 9.00 |
| Temples | 9 | 7.63E−03 | 4.44E−07 | 5.16E−11 | 7.51E−15 | 65.56 | 9.00 |

$$\text{Sag} = \text{SAG} + \alpha\, \text{SAG}^N$$

| R0 | R | θ | Sag1 | Sag2 | α1 | N | α2 |
|---|---|---|---|---|---|---|---|
| −25 |  |  |  |  | 2 | 2 | 2.5 |
| −25 |  |  |  |  | 2 | 2 | 2.5 |
| −25 |  |  |  |  | 2 | 2 | 2.5 |
| −25 | −35 | 9.894 | 11.071 | 13.053 | 2 | 2 | 2.5 |
| −25 | −30 | 7.138 | 7.211 | 8.830 | 2 | 2 | 2.5 |
| −25 | −25 | 4.887 | 4.887 | 6.436 | 2 | 2 | 2.5 |
| −25 | −20 | 3.094 | 3.094 | 4.625 | 2 | 2 | 2.5 |
| −25 | −20 | 3.094 | 3.094 | 4.625 | 2 | 2 | 2.5 |
| −25 | −15 | 1.727 | 1.727 | 3.239 | 2 | 2 | 2.5 |
| −25 | −10 | 0.763 | 0.763 | 2.267 | 2 | 2 | 2.5 |
| −25 | −5 | 0.190 | 0.190 | 1.691 | 2 | 2 | 2.5 |
| −25 | 0 | 0.000 | 0.000 | 1.500 | 2 | 2 | 2.5 |
| 25 | 5 | 0.190 | 0.190 | 1.691 | 2 | 2 | 2.5 |
| 25 | 10 | 0.763 | 0.763 | 2.267 |  | 2 | 2.5 |
| 25 | 15 | 1.727 | 1.727 | 3.239 | 2 | 2 | 2.5 |
| 25 | 20 | 3.094 | 3.094 | 4.625 | 2 | 2 | 2.5 |
| 25 | 25 | 4.887 | 4.887 | 6.436 | 2 | 2 | 2.5 |
| 25 | 30 | 7.138 | 7.211 | 8.830 | 2 | 2 | 2.5 |
| 25 | 35 | 9.894 | 11.071 | 13.092 | 2 | 2 | 2.5 |
| 25 | 40 | 13.221 | 19.271 | 22.662 | 2 | 2 | 2.5 |

TABLE 7

|  | B | A2 | A4 | A6 | A8 | r | D |
|---|---|---|---|---|---|---|---|
| Front Surface | 9 | 7.63E−03 | 4.44E−07 | 5.16E−11 | 7.51E−15 | 65.56 | 9.00 |
|  | 9 | 7.63E−03 | 4.44E−07 | 5.16E−11 | 7.51E−15 | 65.56 | 9.00 |
| Back Surface | 7 | 5.93E−03 | 2.09E−07 | 1.47E−11 | 1.29E−15 | 84.29 | 7.00 |
| Front temples | 5.75 | 4.87E−03 | 1.16E−07 | 5.49E−12 | 3.26E−16 | 102.61 | 5.75 |

TABLE 7-continued

| | |
|---|---|
| Center Thickness (mm) | 2.61 |
| Edge Thickness (40 mm) | 1.00 |

| RO | R | 9 | 9 | 7 | DSAG | sag | α | N |
|---|---|---|---|---|---|---|---|---|
| −23.25 | −50 | | 22.94 | | 3.55 | | −1 | 2 |
| −23.25 | −45 | | 17.82 | | 2.33 | | −1 | 2 |
| −23.25 | −40 | | 13.60 | | 1.38 | | −1 | 2 |
| −23.25 | −35 | | 10.12 | | 0.67 | | −1 | 2 |
| −23.25 | −30 | | 7.27 | | 0.22 | | −1 | 2 |
| −23.25 | −25 | 4.95 | 4.95 | 6.40 | 0.01 | | −1 | 2 |
| −23.25 | −20 | 3.13 | 3.13 | 5.02 | 0.05 | | −1 | 2 |
| −23.25 | −20 | 3.13 | 3.13 | 5.02 | 0.05 | | −1 | 2 |
| −23.25 | −15 | 1.74 | 1.74 | 3.96 | 0.33 | | −1 | 2 |
| −23.25 | −10 | 0.77 | 0.77 | 3.21 | 0.86 | | −1 | 2 |
| −23.25 | −5 | 0.19 | 0.19 | 2.76 | 1.64 | | −1 | 2 |
| −23.25 | 0 | 0.00 | 0.00 | 2.61 | 2.67 | | −1 | 2 |
| −23.25 | 5 | 0.19 | 0.19 | 2.76 | 3.97 | | −1 | 2 |
| −23.25 | 10 | 0.77 | 0.77 | 3.21 | 5.54 | | −1 | 2 |
| −23.25 | 15 | 1.74 | 1.74 | 3.96 | 7.40 | | −1 | 2 |
| −23.25 | 20 | 3.13 | 3.13 | 5.02 | 9.56 | | −1 | 2 |
| −23.25 | 25 | 4.95 | 4.95 | 6.40 | 0.01 | 4.95 | −1 | 2 |
| −23.25 | 30 | 7.27 | 7.27 | 8.13 | 0.22 | 7.22 | −1 | 2 |
| −23.25 | 35 | | 10.12 | 10.22 | 0.89 | 9.33 | −1 | 2 |
| −23.25 | 40 | | 13.60 | 12.70 | 1.38 | 11.71 | −1 | 2 |

TABLE 8

| | B | A2 | A4 | A6 | A8 | r | D |
|---|---|---|---|---|---|---|---|
| Front Surface | 12 | 1.02E−02 | 1.05E−06 | 2.18E−10 | 5.62E−14 | 49.17 | 12.00 |
| | 12 | 1.02E−02 | 1.05E−06 | 2.18E−10 | 5.62E−14 | 49.17 | 12.00 |
| Back Surface | 8 | 6.78E−03 | 3.12E−07 | 2.86E−11 | 3.29E−15 | 73.74 | 8.00 |
| Front temples | 4.25 | 3.60E−03 | 4.67E−08 | 1.21E−12 | 3.93E−17 | 138.82 | 4.25 |
| Center Thickness (mm) | | 4.55 | | | | | |
| Edge Thickness (40 mm) | | 0.91 | | | | | |

| RO | R | 12 | 12 | 8 | DSAG | sag | α | N |
|---|---|---|---|---|---|---|---|---|
| −17.5 | −50 | | 37.59 | | 3.86 | | −1.425 | 2 |
| −17.5 | −45 | | 27.66 | | 2.75 | | −1.425 | 2 |
| −17.5 | −40 | | 20.22 | | 1.84 | | −1.425 | 2 |
| −17.5 | −35 | | 14.56 | | 1.11 | | −1.425 | 2 |
| −17.5 | −30 | | 10.20 | | 0.56 | | −1.425 | 2 |
| −17.5 | −25 | 6.83 | 6.83 | 8.92 | 0.20 | | −1.425 | 2 |
| −17.5 | −20 | 4.25 | 4.25 | 7.31 | 0.02 | | −1.425 | 2 |
| −17.5 | −20 | 4.25 | 4.25 | 7.31 | | | −1.425 | 2 |
| −17.5 | −15 | 2.34 | 2.34 | 6.09 | | | −1.425 | 2 |
| −17.5 | −10 | 1.03 | 1.03 | 5.23 | | | −1.425 | 2 |
| −17.5 | −5 | 0.25 | 0.25 | 4.72 | | | −1.425 | 2 |
| −17.5 | 0 | 0.00 | 0.00 | 4.55 | | | −1.425 | 2 |
| −17.5 | 5 | 0.25 | 0.25 | 4.72 | | | −1.425 | 2 |
| −17.5 | 10 | 1.03 | 1.03 | 5.23 | | | −1.425 | 2 |
| −17.5 | 15 | 2.34 | 2.34 | 6.09 | | | −1.425 | 2 |
| −17.5 | 20 | 4.25 | 4.25 | 7.31 | 10.02 | | −1.425 | 2 |
| −17.5 | 25 | 6.83 | 6.83 | 8.92 | 0.20 | 6.77 | −1.425 | 2 |
| −17.5 | 30 | | 10.20 | 10.93 | 0.56 | 9.75 | −1.425 | 2 |
| −17.5 | 35 | | 14.56 | 13.38 | 1.13 | 12.73 | −1.425 | 2 |
| −17.5 | 40 | | 20.22 | 16.33 | 1.84 | 15.42 | −1.425 | 2 |

TABLE 9

| | B | A2 | A4 | A6 | A8 | r | D |
|---|---|---|---|---|---|---|---|
| Front Surface | 12 | 1.02E−02 | 1.05E−06 | 2.18E−10 | 5.62E−14 | 49.17 | 12.00 |
| | 12 | 1.02E−02 | 1.05E−06 | 2.18E−10 | 5.62E−14 | 49.17 | 12.00 |
| Back Surface | 8 | 6.78E−03 | 3.12E−07 | 2.86E−11 | 3.29E−15 | 73.75 | 8.00 |
| Front Temples | 12 | 0.00E+00 | 1.05E−06 | 2.18E−10 | 5.62E−14 | | 0.00 |
| Center Thickness (mm) | | 4.55 | | | | | |

TABLE 9-continued

|  | B | A2 | A4 | A6 | A8 | r | D |
|---|---|---|---|---|---|---|---|
| Edge Thickness (40 mm) |  | 0.84 |  |  |  |  |  |

| R0 | R | 12 | 12 | 8 | DSAG | sag | α | N |
|---|---|---|---|---|---|---|---|---|
| −15 | −50 |  | 37.59 |  | 2.10 |  | −10 | 1 |
| −15 | −45 |  | 27.66 |  | 1.05 |  | −10 | 1 |
| −15 | −40 |  | 20.22 |  | 0.47 |  | −10 | 1 |
| −15 | −35 |  | 14.56 |  | 0.18 |  | −10 | 1 |
| −15 | −30 |  | 10.20 |  | 0.06 |  | −10 | 1 |
| −15 | −25 | 6.83 | 6.83 | 8.92 | 0.01 |  | −10 | 1 |
| −15 | −20 | 4.25 | 4.25 | 7.31 |  |  | −10 | 1 |
| −15 | −20 | 4.25 | 4.25 | 7.31 |  |  | −10 | 1 |
| −15 | −15 | 2.34 | 2.34 | 6.09 |  |  | −10 | 1 |
| −15 | −10 | 1.03 | 1.03 | 5.23 |  |  | −10 | 1 |
| −15 | −5 | 0.25 | 0.25 | 4.72 |  |  | −10 | 1 |
| −15 | 0 | 0.00 | 0.00 | 4.55 |  |  | −10 | 1 |
| −15 | 5 | 0.25 | 0.25 | 4.72 |  |  | −10 | 1 |
| −15 | 10 | 1.03 | 1.03 | 5.23 |  |  | −10 | 1 |
| −15 | 15 | 2.34 | 2.34 | 6.09 |  |  | −10 | 1 |
| −15 | 20 | 4.25 | 4.25 | 7.31 |  |  | −10 | 1 |
| −15 | 25 | 6.83 | 6.83 | 8.92 | 0.01 | 6.72 | −10 | 1 |
| −15 | 30 |  | 10.20 | 10.93 | 0.06 | 9.64 | −10 | 1 |
| −15 | 35 |  | 14.56 | 13.38 | 0.18 | 12.73 | −10 | 1 |
| −15 | 40 |  | 20.22 | 16.33 | 0.47 | 15.50 | −10 | 1 |

TABLE 10

|  | B | A2 | A4 | A6 | A8 | r | D |
|---|---|---|---|---|---|---|---|
| Front Surface | 4.5 | 3.81E−03 | 5.55E−08 | 1.61E−12 | 5.87E−17 | 131.11 | 4.50 |
|  | 4.5 | 3.81E−03 | 5.55E−08 | 1.61E−12 | 5.87E−17 | 131.11 | 4.50 |
| Back Surface | 8.5 | 7.20E−03 | 3.74E−07 | 3.88E−11 | 5.03E−15 | 69.41 | 8.50 |
| Front Temples | 2.5 | 2.12E−03 | 9.51E−09 | 8.54E−14 | 9.58E−19 | 236.00 | 2.50 |
| Center Thickness (mm) |  | 1 |  |  |  |  |  |
| Edge Thickness (40 mm) |  | 4.51 |  |  |  |  |  |

| R0 | R | 4.5 | 4.5 | 8.5 | DSAG | sag | α | N |
|---|---|---|---|---|---|---|---|---|
| −15 | −50 |  | 9.91 |  | 2.61 |  | 1.65 | 2 |
| −15 | −45 |  | 7.96 |  | 1.91 |  | 1.65 | 2 |
| −15 | −40 |  | 6.25 |  | 1.33 |  | 1.65 | 2 |
| −15 | −35 |  | 4.76 |  | 0.85 |  | 1.65 | 2 |
| −15 | −30 |  | 3.48 |  | 0.48 |  | 1.65 | 2 |
| −15 | −25 | 2.41 | 2.41 | 5.66 | 0.21 |  | 1.65 | 2 |
| −15 | −20 | 1.53 | 1.53 | 3.94 | 0.05 |  | 1.65 | 2 |
| −15 | −20 | 1.53 | 1.53 | 3.94 | 0.05 |  | 1.65 | 2 |
| −15 | −15 | 0.86 | 0.86 | 2.64 | 0.00 |  | 1.65 | 2 |
| −15 | −10 | 0.38 | 0.38 | 1.72 | 0.05 |  | 1.65 | 2 |
| −15 | −5 | 0.10 | 0.10 | 1.18 | 0.21 |  | 1.65 | 2 |
| −15 | 0 | 0.00 | 0.00 | 1.00 | 0.48 |  | 1.65 | 2 |
| −15 | 5 | 0.10 | 0.10 | 1.18 | 0.85 |  | 1.65 | 2 |
| −15 | 10 | 0.38 | 0.38 | 1.72 | 1.33 |  | 1.65 | 2 |
| −15 | 15 | 0.86 | 0.86 | 2.64 | 1.91 |  | 1.65 | 2 |
| −15 | 20 | 1.53 | 1.53 | 3.94 | 2.61 |  | 1.65 | 2 |
| −15 | 25 | 2.41 | 2.41 | 5.66 | 0.21 | 2.48 | 1.65 | 2 |
| −15 | 30 |  | 3.48 | 7.82 | 0.48 | 3.85 | 1.65 | 2 |
| −15 | 35 |  | 4.76 | 10.47 | 0.85 | 5.95 | 1.65 | 2 |
| −15 | 40 |  | 6.25 | 13.67 | 1.33 | 9.16 | 1.65 | 2 |

TABLE 11

|  | B | A2 | A4 | A6 | A8 | r | D |
|---|---|---|---|---|---|---|---|
| Front Surface | 4.5 | 3.81E−03 | 5.55E−08 | 1.61E−12 | 5.87E−17 | 131.11 | 4.50 |
|  | 4.5 | 3.81E−03 | 5.55E−08 | 1.61E−12 | 5.87E−17 | 131.11 | 4.50 |
| Back Surface | 8.5 | 7.20E−03 | 3.74E−07 | 3.88E−11 | 5.03E−15 | 69.41 | 8.50 |
| Front Temples | 11 | 0.00E+00 | 8.10E−07 | 1.41E−10 | 3.06E−14 |  | 0.00 |
| CenterThickness(mm) |  | 1 |  |  |  |  |  |
| EdgeThickness |  | 3.95 |  |  |  |  |  |

TABLE 11-continued (40mm)

| R0 | R | 4.5 | 4.5 | 8.5 | DSAG | sag | α | N |
|---|---|---|---|---|---|---|---|---|
| −15 | −50 | | 9.91 | | 1.54 | | 10 | 1 |
| −15 | −45 | | 7.96 | | 0.78 | | 10 | 1 |
| −15 | −40 | | 6.25 | | 0.36 | | 10 | 1 |
| −15 | −35 | | 4.76 | | 0.14 | | 10 | 1 |
| −15 | −30 | | 3.48 | | 0.04 | | 10 | 1 |
| −15 | −25 | 2.41 | 2.41 | 5.66 | 0.01 | | 10 | 1 |
| −15 | −20 | 1.53 | 1.53 | 3.94 | 0.00 | | 10 | 1 |
| −15 | −20 | 1.53 | 1.53 | 3.94 | 0.00 | | 10 | 1 |
| −15 | −15 | 0.86 | 0.86 | 2.64 | 0.00 | | 10 | 1 |
| −15 | −10 | 0.38 | 0.38 | 1.72 | 0.00 | | 10 | 1 |
| −15 | −5 | 0.10 | 0.10 | 1.18 | 0.01 | | 10 | 1 |
| −15 | 0 | 0.00 | 0.00 | 1.00 | 0.04 | | 10 | 1 |
| −15 | 5 | 0.10 | 0.10 | 1.18 | 0.14 | | 10 | 1 |
| −15 | 10 | 0.38 | 0.38 | 1.72 | 0.36 | | 10 | 1 |
| −15 | 15 | 0.86 | 0.86 | 2.64 | 0.78 | | 10 | 1 |
| −15 | 20 | 1.53 | 1.53 | 3.94 | 1.54 | | 10 | 1 |
| −15 | 25 | 2.41 | 2.41 | 5.66 | 0.01 | 2.41 | 10 | 1 |
| −15 | 30 | | 3.48 | 7.82 | 0.04 | 3.83 | 10 | 1 |
| −15 | 35 | | 4.76 | 10.47 | 0.14 | 6.07 | 10 | 1 |
| −15 | 40 | | 6.25 | 13.67 | 0.36 | 9.73 | 10 | 1 |

TABLE 12

| Lens Rx | 3.00 | Index | 1.59 |
|---|---|---|---|
| Center Depth | 2.10 | Extension Power | 0 |
| Edge Thickness | 1.00 | Optic Diameter | 0 |
| Center Thickness | 3.10 | | |

| | B | A0 | A2 | A4 | A6 | A8 | r | D |
|---|---|---|---|---|---|---|---|---|
| Center | 11.00 | −3.00 | 9.32E−03 | 8.19E−07 | 1.41E−10 | 3.06E−14 | 53.64 | 11.00 |
| Optic | 10.75 | −2.83 | 9.11E−03 | 7.56E−07 | 1.26E−10 | 2.60E−14 | 54.88 | 10.75 |
| | 10.50 | −2.55 | 8.00E−03 | 7.05E−07 | 1.12E−10 | 2.21E−14 | 56.19 | 10.50 |
| | 10.25 | −2.48 | 8.69E−03 | 6.55E−07 | 9.89E−11 | 1.87E−14 | 57.56 | 10.25 |
| | 10.00 | −2.30 | 8.47E−03 | 6.09E−07 | 8.74E−11 | 1.57E−14 | 59.00 | 10.00 |
| | 9.75 | −2.13 | 8.26E−03 | 5.64E−07 | 7.70E−11 | 1.31E−14 | 60.51 | 9.75 |
| | 9.50 | −1.95 | 8.05E−03 | 5.22E−07 | 6.76E−11 | 1.10E−14 | 62.11 | 9.50 |
| | 9.25 | −1.78 | 7.84E−03 | 4.82E−07 | 5.92E−11 | 9.09E−15 | 63.78 | 9.25 |
| | 9.00 | −1.60 | 7.63E−03 | 4.44E−07 | 5.16E−11 | 7.51E−15 | 65.56 | 9.00 |
| | 8.75 | −1.43 | 7.42E−03 | 4.08E−07 | 4.48E−11 | 6.16E−15 | 67.43 | 8.75 |
| | 8.50 | −1.25 | 7.20E−03 | 3.74E−07 | 3.88E−11 | 5.03E−15 | 69.41 | 8.50 |
| | 8.25 | −1.08 | 6.99E−03 | 3.42E−07 | 3.34E−11 | 4.08E−15 | 71.52 | 8.25 |
| Extension | 8.00 | −0.90 | 6.78E−03 | 3.12E−07 | 2.86E−11 | 2.29E−15 | 73.75 | 8.00 |
| Frame | 8.00 | 0.10 | 8.78E−03 | 3.12E−07 | 2.86E−11 | 3.29E−15 | 73.75 | 8.00 |
| Back Optic | 8.00 | 0.10 | 6.78E−03 | 3.12E−07 | 2.86E−11 | 3.29E−15 | 73.75 | 8.00 |

| Sag | | Front | Frame | Back | |
|---|---|---|---|---|---|
| R | Xtn | 11.0 | 8 | 8 | |
| −30.00 | | 6.169 | 6.477 | 6.477 | |
| −25.00 | | 3.182 | 4.467 | 4.467 | |
| −20.00 | | 0.868 | 2.864 | 2.864 | |
| −15.00 | | −0.860 | 1.642 | 1.642 | |
| −10.00 | | −2.060 | 0.781 | 0.781 | |
| −5.00 | | −2.766 | 0.270 | 0.270 | |
| 0.00 | | −3.000 | 0.100 | 0.100 | |
| 5.00 | | −2.766 | 0.270 | 0.270 | |
| 10.00 | | −2.060 | 0.781 | 0.781 | |
| 15.00 | | −0.860 | 1.642 | 1.642 | |
| 20.00 | 0.868 | 0.868 | 2.864 | 2.864 | Thickness |
| 25.00 | 3.182 | 3.199 | 4.467 | 4.467 | 1.268 |
| 25.07 | 3.218 | 3.252 | 4.492 | 4.492 | 1.240 |
| 25.28 | 3.329 | 3.372 | 4.567 | 4.567 | 1.195 |
| 25.63 | 3.516 | 3.555 | 4.695 | 4.695 | 1.140 |
| 26.11 | 3.783 | 3.798 | 4.877 | 4.877 | 1.079 |
| 26.74 | 4.137 | 4.099 | 5.117 | 5.117 | 1.018 |
| 27.50 | 4.584 | 4.457 | 5.419 | 5.419 | 0.962 |
| 28.40 | 5.134 | 4.872 | 5.789 | 5.789 | 0.917 |
| 29.44 | 5.80 | 5.343 | 6.233 | 6.233 | 0.890 |
| 30.63 | 6.595 | 5.871 | 6.759 | 6.759 | 0.888 |
| 31.94 | 7.539 | 6.455 | 7.377 | 7.377 | 0.922 |

TABLE 12-continued

| 33.40 | 8.652 | 7.097 | 8.097 | 8.097 | 1.000 |
| 35.00 | 9.963 | 7.933 | 8.933 | 8.933 | 1.000 |
| 40.00 | 14.766 | 10.884 | 11.884 | 11.884 | 1.000 |
| 45.00 | 20.882 | 14.400 | 15.400 | 15.400 | 1.000 |
| 50.00 |  | 18.573 | 19.573 | 19.573 |  |

TABLE 13

| Lens Rx | 1.0 | Extension Power | 0.00 |
| Center Thickness | 2.43 | Optic Diameter | 60 |
| Edge Thickness | 1.000 | Spectacle Aperture | 85 |
|  |  | Material: Polycarbonate |  |

|  | B | A2 | A4 | A6 | A8 | r | D |
| --- | --- | --- | --- | --- | --- | --- | --- |
| Front Optic | 9.0 | 7.63E−03 | 4.44E−07 | 5.16E−11 | 7.51E−15 | 65.56 | 9.00 |
| Extension | 8 | 6.78E−03 | 3.13E−07 | 2.86E−11 | 3.29E−15 | 73.75 | 8.00 |
| Frame | 8 | 6.78E−03 | 3.12E−07 | 2.86E−11 | 3.29E−15 | 73.75 | 8.00 |
| Back Optic | 8 | 6.78E−03 | 3.12E−07 | 2.86E−11 | 3.29E−15 | 73.75 | 8.00 |

| Sag | Back | Front | Extn | Frame |
| --- | --- | --- | --- | --- |
| R | 8.00 | 9.0 | 8 | 8 |
| −50 |  |  |  |  |
| −45 |  |  |  |  |
| −40 |  |  |  |  |
| −35 |  |  |  |  |
| −30 |  |  |  |  |
| −25 | 4.4965103 | 2.6540148 |  | 3.8665103 |
| −20 | 2.8936411 | 0.8220304 |  | 2.2636411 |
| −20 | 2.8936411 | 0.8253341 |  | 2.2636411 |
| −15 | 1.6715342 | −0.560829 |  | 1.0415342 |
| −10 | 0.8111113 | −1.532799 |  | 0.1811113 |
| −5 | 0.2996867 | −2.109044 |  | −0.330313 |
| 0 | 0.13 | −2.3 |  | −0.5 |
| 5 | 0.2996867 | −2.109044 |  | −0.330313 |
| 10 | 0.8111113 | −1.532799 |  | 0.1811113 |
| 15 | 1.6715342 | −0.560829 |  | 1.0415342 |
| 20 | 2.8936411 | 0.8253341 |  | 2.2636411 |
| 25 | 4.4965103 | 2.6540148 |  | 3.8665103 |
| 30 | 6.5071492 | 4.9663551 | 6.5071492 | 5.8771492 |
| 35 | 8.9627803 | 7.9627803 | 8.9627803 | 8.3327803 |
| 40 | 11.914111 | 10.914111 | 11.914111 | 11.284111 |

TABLE 14

| Lens Rx | −2.0 | Extension Power |  |
| Center Thickness | 1 | Optic Diameter | 55 |
| Edge Thickness | 2.75 | Spectacle Aperture | 70 |
| Base Curve | 6.5 | Material: Polycarbonate |  |

|  | B | A2 | A4 | A6 | A8 | r | D |
| --- | --- | --- | --- | --- | --- | --- | --- |
| Front Optic | 6.5 | 5.51E−03 | 1.67E−07 | 1.01E−11 | 7.69E−16 | 90.77 | 6.50 |
| Extension | 8.5 | 7.20E−03 | 3.74E−07 | 3.88E−11 | 5.03E−15 | 69.41 | 8.50 |
| Frame | 8 | 6.78E−03 | 3.12E−07 | 2.86E−11 | 3.29E−15 | 73.75 | 8.00 |
| Back Optic | 8 | 6.78E−03 | 3.12E−07 | 2.86E−11 | 3.29E−15 | 73.75 | 8.00 |

| Sag | Extension | Front | Back | Frame |
| --- | --- | --- | --- | --- |
| R | 8.00 | 6.5 | 8.5 | 8 |
| −50 |  |  |  |  |
| −45 |  |  |  |  |
| −40 |  |  |  |  |
| −35 |  |  |  |  |
| −30 |  |  |  |  |
| −25 |  | 3.5106816 | 5.6583626 | 4.3665103 |
| −20 |  | 2.2301528 | 3.9437713 | 2.7636411 |
| −20 |  | 2.230802 | 3.9437713 | 2.7636411 |
| −15 |  | 1.247986 | 3.9437713 | 2.7636411 |
| −10 |  | 0.5525291 | 1.724116 | 1.5415342 |
| −5 |  | 0.1378165 | 1.180319 | 0.1696867 |
| 0 |  | 0 | 1 | 0 |
| 5 |  | 0.1378165 | 1.180319 | 0.1696867 |

TABLE 14-continued

| | | | | |
|---|---|---|---|---|
| 10 | | 0.5525291 | 1.724116 | 0.6811113 |
| 15 | | 1.247986 | 2.6401398 | 1.5415342 |
| 20 | | 2.230802 | 3.9437713 | 2.7636411 |
| 25 | 3.5105103 | 3.5103816 | 3.6583626 | 4.3665103 |
| 30 | 5.5211492 | 5.4609142 | 7.8173879 | 6.3771492 |
| 35 | 7.9767803 | 7.9767803 | 10.467686 | 8.8327803 |
| 40 | 10.928111 | 10.928111 | 13.674148 | 11.784111 |

TABLE 15

Lens radius
40.0
Front surface
number of polynomial pieces
Degree of Polynomial 3
Front surface (piece 1)
Degree of polynomial 8
Coefficients of optically optimised central surface asphere applies from r = 0 to r = 20
+0.00000D+00 0
+0.00000D+00 1
+1.03280D−02 2
+0.00000D+00 3
+1.26810D−06 4
+0.00000D+00 5
+3.00100D−10 6
+0.00000D+00 7
+1.82900D−13 8
Blend radius (1–2)
20
Front surface (piece 2)
Degree of polynomial 3
Spline polynomial blending inner aspheric to outer sphere applies from r = 20 to r = 35
−7.53462D+00 0
+8.36819D−01 1
−1.75540D−02 2
+2.72230D−4 3
Blend radius (2–3)
35
Front surface (piece 3)
Degree of Polynomial 8
Coefficients of outer sphere applies outside r = 35
+2.10000D+00 0
+0.00000D+00 1
+7.43494D−03 2
+0.00000D+00 3
+4.10992D−07 4
+0.00000D+00 5
+4.54379D−11 6
+0.0000D+00 7
+6.27934D−15 8
Centre thickness
3.1
Back surface
number of polynomial pieces 1
Back surface (piece 1)
Degree of Polynomial 8
Coefficients of back surface sphere
+3.10000D+00
+0.00000D+00
+7.54717D−03
+0.00000D+00
+4.29885D−07
+0.00000D+00
+4.89723D−11
+0.00000D+00
+6.97363D−15

| Radius | Thickness | sag (front) | sag (back) | zFront | zBack | TCrv |
|---|---|---|---|---|---|---|
| 0.00 | 3.10 | 0.00 | 0.00 | 0.00 | 3.10 | 10.95 |
| 1.00 | 3.10 | 0.01 | 0.01 | 0.01 | 3.11 | 10.95 |
| 2.00 | 3.09 | 0.04 | 0.03 | 0.04 | 3.13 | 10.95 |
| 3.00 | 3.07 | 0.09 | 0.07 | 0.09 | 3.17 | 10.96 |
| 4.00 | 3.06 | 0.17 | 0.12 | 0.17 | 3.22 | 10.96 |
| 5.00 | 3.03 | 0.26 | 0.19 | 0.26 | 3.29 | 10.97 |
| 6.00 | 3.00 | 0.37 | 0.27 | 0.37 | 3.37 | 10.99 |
| 7.00 | 2.96 | 0.51 | 0.37 | 0.51 | 3.47 | 11.00 |
| 8.00 | 2.92 | 0.67 | 0.48 | 0.67 | 3.58 | 11.02 |
| 9.00 | 2.87 | 0.85 | 0.61 | 0.85 | 3.71 | 11.03 |
| 10.00 | 2.81 | 1.05 | 0.76 | 1.05 | 3.86 | 11.05 |
| 11.00 | 2.75 | 1.27 | 0.92 | 1.27 | 4.02 | 11.08 |
| 12.00 | 2.68 | 1.51 | 1.10 | 1.51 | 4.20 | 11.10 |
| 13.00 | 2.60 | 1.78 | 1.29 | 1.78 | 4.39 | 11.13 |
| 14.00 | 2.52 | 2.08 | 1.50 | 2.08 | 4.60 | 11.17 |
| 15.00 | 2.43 | 2.39 | 1.72 | 2.39 | 4.82 | 11.20 |
| 16.00 | 2.33 | 2.73 | 1.96 | 2.73 | 5.06 | 11.24 |
| 17.00 | 2.22 | 3.10 | 2.22 | 3.10 | 5.32 | 11.29 |
| 18.00 | 2.10 | 3.49 | 2.49 | 3.49 | 5.59 | 11.34 |
| 19.00 | 1.97 | 3.91 | 2.78 | 3.91 | 5.88 | 11.39 |
| 20.00 | 1.83 | 4.36 | 3.09 | 4.36 | 6.19 | −0.97 |
| 21.00 | 1.70 | 4.82 | 3.42 | 4.82 | 6.52 | −0.32 |
| 22.00 | 1.58 | 5.28 | 3.76 | 5.28 | 6.86 | 0.33 |
| 23.00 | 1.48 | 5.74 | 4.12 | 5.74 | 7.22 | 0.98 |
| 24.00 | 1.40 | 6.20 | 4.50 | 6.20 | 7.60 | 1.62 |
| 25.00 | 1.33 | 6.67 | 4.90 | 6.67 | 8.00 | 2.25 |
| 26.00 | 1.27 | 7.14 | 5.31 | 7.14 | 8.41 | 2.87 |
| 27.00 | 1.23 | 7.62 | 5.75 | 7.62 | 8.85 | 3.47 |
| 28.00 | 1.20 | 8.11 | 6.21 | 8.11 | 9.31 | 4.06 |
| 29.00 | 1.17 | 8.61 | 6.68 | 8.61 | 9.78 | 4.62 |
| 30.00 | 1.16 | 9.12 | 7.18 | 9.12 | 10.28 | 5.15 |
| 31.00 | 1.15 | 9.65 | 7.70 | 9.65 | 10.80 | 5.65 |
| 32.00 | 1.15 | 10.19 | 8.24 | 10.19 | 11.34 | 6.12 |
| 33.00 | 1.15 | 10.75 | 8.80 | 10.75 | 11.90 | 6.55 |
| 34.00 | 1.16 | 11.32 | 9.39 | 11.32 | 12.49 | 6.94 |
| 35.00 | 1.17 | 11.92 | 10.00 | 11.92 | 13.10 | 7.29 |
| 36.00 | 1.19 | 12.54 | 10.63 | 12.54 | 13.73 | 7.78 |
| 37.00 | 1.20 | 13.19 | 11.29 | 13.19 | 14.39 | 7.76 |
| 38.00 | 1.22 | 13.86 | 11.97 | 13.86 | 14.07 | 7.73 |
| 39.00 | 1.23 | 14.55 | 12.68 | 14.55 | 15.78 | 7.70 |
| 40.00 | 1.25 | 15.28 | 13.42 | 15.28 | 16.52 | 7.67 |

TABLE 16

Lens radius
40.0
Front surface
number of polynomial pieces
Degree of Polynomial 3
Front surface (piece 1)
Degree of Polynomial 8
Coefficients of optically optimised central surface asphere applies from r = 0 to r = 20
+0.00000D+00
+0.00000D+00
+4.52750D−03
+0.00000D+00
+1.17470D−07
+0.00000D+00
−7.92780D−11
+0.00000D+00
+1.86270D−14
Blend radius (1–2)
20
Front surface (piece 2)
Degree of Polynomial 3
+1.44473D+01

TABLE 16-continued

−1.66106D+00
+6.22643D−02
−5.38318D−04
Blend radius (2–3)
40
Front surface (piece 3)
Degree of Polynomial 8
Coefficients of optically optimised central surface asphere applies from
r = 0 to 4 = 20
+0.00000D+00
+0.00000D+00
+7.43494D−03
+0.00000D+00
+4.10992D−07
+0.00000D.00
+4.54379D−11
+0.00000D+00
+6.27934D−15
Centre thickness 1
Back surface
number of polynomial pieces 1
Back surface (piece 1)
Degree of Polynomial 8
+1.00000D+00
+0.00000D+00
+7.54717D−03
+0.00000D+00
+4.29885D−07
+0.00000D+00
+4.89723D−11
+0.00000D+00
+6.97363D−15

| Radius | Thickness | sag (front) | sag (back) | zFront | zBack | TCrv |
|---|---|---|---|---|---|---|
| 0.00 | 1.00 | 0.00 | 0.00 | 0.00 | 1.00 | 4.80 |
| 1.00 | 1.00 | 0.00 | 0.01 | 0.00 | 1.01 | 4.80 |
| 2.00 | 1.01 | 0.02 | 0.03 | 0.02 | 1.03 | 4.80 |
| 3.00 | 1.03 | 0.04 | 0.07 | 0.04 | 1.07 | 4.80 |
| 4.00 | 1.05 | 0.07 | 0.12 | 0.07 | 1.12 | 4.80 |
| 5.00 | 1.08 | 0.11 | 0.19 | 0.11 | 1.19 | 4.80 |
| 6.00 | 1.11 | 0.16 | 0.27 | 0.16 | 1.27 | 4.80 |
| 7.00 | 1.15 | 0.22 | 0.37 | 0.22 | 1.37 | 4.80 |
| 8.00 | 1.19 | 0.29 | 0.48 | 0.29 | 1.48 | 4.80 |
| 9.00 | 1.25 | 0.37 | 0.61 | 0.37 | 1.61 | 4.80 |
| 10.00 | 1.31 | 0.45 | 0.76 | 0.45 | 1.76 | 4.80 |
| 11.00 | 1.37 | 0.55 | 0.92 | 0.55 | 1.92 | 4.80 |
| 12.00 | 1.44 | 0.65 | 1.10 | 0.65 | 2.10 | 4.80 |
| 13.00 | 1.52 | 0.77 | 1.29 | 0.77 | 2.29 | 4.79 |
| 14.00 | 1.60 | 0.89 | 1.50 | 0.89 | 2.50 | 4.78 |
| 15.00 | 1.70 | 1.02 | 1.72 | 1.02 | 2.72 | 4.77 |
| 16.00 | 1.80 | 1.17 | 1.96 | 1.17 | 2.96 | 4.76 |
| 17.00 | 1.90 | 1.32 | 2.22 | 1.32 | 3.22 | 4.75 |
| 18.00 | 2.02 | 1.48 | 2.49 | 1.48 | 3.49 | 4.73 |
| 19.00 | 2.14 | 1.65 | 2.78 | 1.65 | 3.78 | 4.71 |
| 20.00 | 2.27 | 1.83 | 3.09 | 1.83 | 4.09 | 30.22 |
| 21.00 | 2.38 | 2.04 | 3.42 | 2.04 | 4.42 | 27.60 |
| 22.00 | 2.45 | 2.31 | 3.76 | 2.31 | 4.76 | 24.97 |
| 23.00 | 2.49 | 2.63 | 4.12 | 2.63 | 5.12 | 22.42 |
| 24.00 | 2.50 | 3.00 | 4.50 | 3.00 | 5.50 | 20.00 |
| 25.00 | 2.47 | 3.42 | 4.90 | 3.42 | 5.90 | 17.74 |
| 26.00 | 2.43 | 3.89 | 5.31 | 3.89 | 6.31 | 15.66 |
| 27.00 | 2.36 | 4.39 | 5.75 | 4.39 | 6.75 | 13.75 |
| 28.00 | 2.27 | 4.94 | 6.21 | 4.94 | 7.21 | 12.01 |
| 29.00 | 2.17 | 5.51 | 6.68 | 5.51 | 7.68 | 10.42 |
| 30.00 | 2.06 | 6.12 | 7.18 | 6.12 | 8.18 | 8.97 |
| 31.00 | 1.95 | 6.75 | 7.70 | 6.75 | 8.70 | 7.65 |
| 32.00 | 1.83 | 7.41 | 8.24 | 7.41 | 9.24 | 6.43 |
| 33.00 | 1.71 | 8.09 | 8.80 | 8.09 | 9.80 | 5.30 |
| 34.00 | 1.60 | 8.79 | 9.39 | 8.79 | 10.39 | 4.25 |
| 35.00 | 1.49 | 9.50 | 10.00 | 9.50 | 11.00 | 3.26 |
| 36.00 | 1.40 | 10.23 | 10.63 | 10.23 | 11.63 | 2.31 |
| 37.00 | 1.33 | 10.96 | 11.29 | 10.96 | 12.29 | 1.39 |
| 38.00 | 1.27 | 11.70 | 11.97 | 11.70 | 12.97 | 0.49 |
| 39.00 | 1.25 | 12.44 | 12.68 | 12.44 | 13.68 | −0.40 |
| 40.00 | 1.25 | 13.18 | 13.42 | 13.18 | 14.42 | −1.29 |

Finally, it is to be understood that various other modifications and/or alterations may be made without departing from the spirit of the present invention as outlined herein.

The invention claimed is:

1. A method of manufacturing an optical lens element adapted for mounting in a form of the wrap-around or shield type, which method includes providing mathematical or numerical representation of a front or back surface of an optical lens element including a section designed to provide the desired prescription (Rx) in the prescription zone; and optionally adding thereto a mathematical or numerical representation of a peripheral temporal zone to define a complete lens surface;

rotating and/or decentering the representation of the lens surface to permit mounting in a suitable frame; and modifying the representation of the lens surface to at least partially correct for errors including astigmatic and mean power errors.

2. A method according to claim 1, including providing a mathematical or numerical representation of an aspheric front surface of an optical lens element including a section designed to provide the desired prescription (Rx) in the prescription zone and having appropriate aspheric coefficients to define a peripheral temporal zone;

rotating and/or decentering the representation of the lens surface to permit mounting in a suitable frame;

subsequently providing a mathematical or numerical representation of a prescription (Rx) back surface; and modifying the representation of the back surface of the lens element to at least partially adjust for errors including astigmatic and mean power errors.

3. A method according to claim 2, including providing a mathematical or numerical representation of a surface of an optical lens element including a section designed to provide the desired prescription (Rx) in the prescription zone; and adding thereto a first mathematical or numerical representation of a peripheral temporal zone thereto; and a second mathematical or numerical representation of a transition section designed to smoothly blend the prescription zone and peripheral temporal zone to define a complete lens surface;

rotating and/or decentering the representation of the lens surface to permit mounting in a suitable frame; and modifying the representation of the lens surface to at lease partially adjust for errors including astigmatic and mean power errors.

4. A method according to claim 3, wherein a surface of the optical lens element is represented by the following formulas sag–SAG $R \leq R_0$, wherein R is the radius measured from the optical axis and $A_2$, $A_4$, $A_6$, and $A_8$ are coefficients that define power and asphericity;

sag–SAG+DSAG $R \geq R_0$, wherein $R_0$ defines the periphery of the temporal region; and $$DSAG=B_2(R-R_0)^2+B_4(R-R_0)^4+B_6(R-R_0)^6+B_8(R-Ro)^8$$

wherein $B_2$, $B_4$, $B_6$, and $B_8$ are coefficients that define power and asphericity.

5. A method according to claim 4, wherein the surface is represented by the formula $$sag=SAG+\alpha(DSAG)N \text{ for } R \geq R_0,$$

where $\alpha$ and $N \geq 1$ are numerical parameters.

* * * * *